United States Patent [19]
Kaji

[11] Patent Number: 5,702,407
[45] Date of Patent: Dec. 30, 1997

[54] LIGATING APPARATUS

[75] Inventor: Kunihide Kaji, Koganei, Japan

[73] Assignee: Olympus Optical Co., Ltd., Tokyo, Japan

[21] Appl. No.: 563,049

[22] Filed: Nov. 27, 1995

[30] Foreign Application Priority Data

| Nov. 29, 1994 | [JP] | Japan | 6-294989 |
| Apr. 10, 1995 | [JP] | Japan | 7-084221 |
| May 19, 1995 | [JP] | Japan | 7-121856 |

[51] Int. Cl.$^6$ ................................................ A61B 17/10
[52] U.S. Cl. ..................................... 606/139; 606/148
[58] Field of Search ........................ 606/139, 148; 289/2, 17

[56] References Cited

U.S. PATENT DOCUMENTS

| 4,683,885 | 8/1987 | Hutterer et al. |
| 5,281,236 | 1/1994 | Bagnato et al. |

FOREIGN PATENT DOCUMENTS

| 3413744 A1 | 11/1985 | Germany . |
| 92 04 296 U | 5/1992 | Germany . |
| 4114204 A1 | 11/1992 | Germany . |
| 93 11 552 U | 10/1993 | Germany . |
| 484461 | 5/1938 | United Kingdom . |

*Primary Examiner*—Michael Buiz
*Assistant Examiner*—Tina T. D. Pham
*Attorney, Agent, or Firm*—Frishauf, Holtz, Goodman, Langer & Chick

[57] ABSTRACT

A ligating apparatus includes a first ligating member having an insertion portion to be inserted into a living body, and a holding member with a substantially C-shaped, unclosed loop portion having a gap section therein. The loop portion is capable of holding at least one of a litigation thread for forming a knot and a needle. A second ligating member has a manipulating device capable of holding at least one of the needle and an end portion of the ligation thread, and capable of being passed through the loop portion. When the loop portion holds the ligation thread and the manipulating device holds the end portion of the ligation thread, the second ligating member is cooperable with the first ligating member to form a knot in the ligation thread by passing the manipulating device through a knot forming loop defined by the ligation thread and the loop portion.

24 Claims, 32 Drawing Sheets

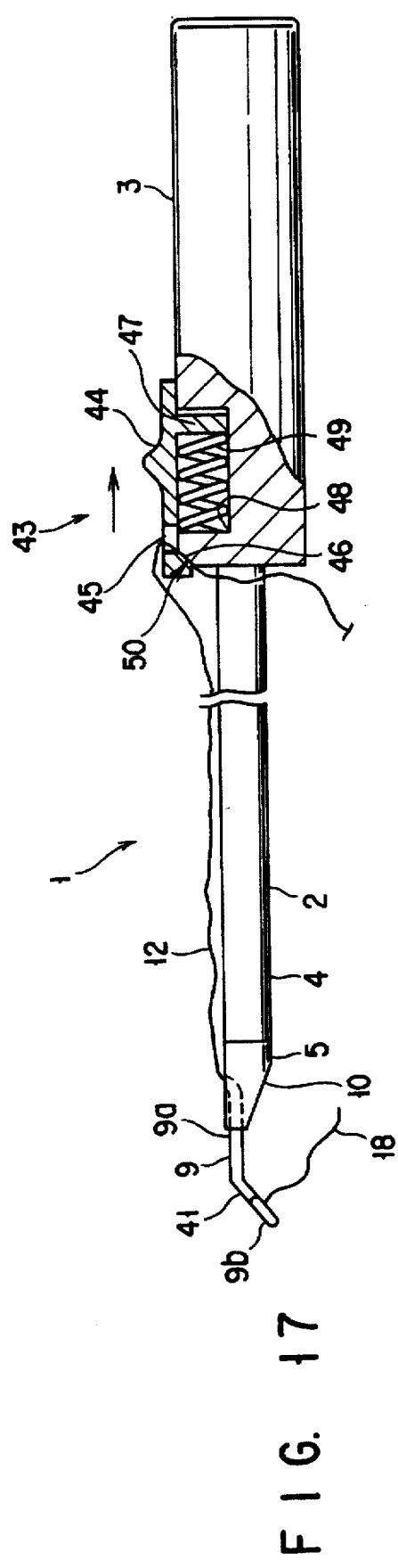
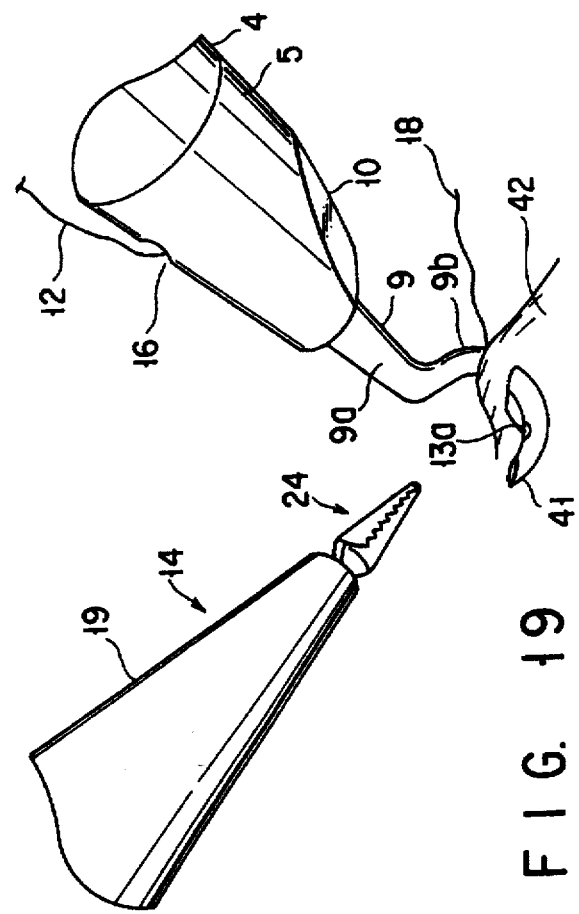
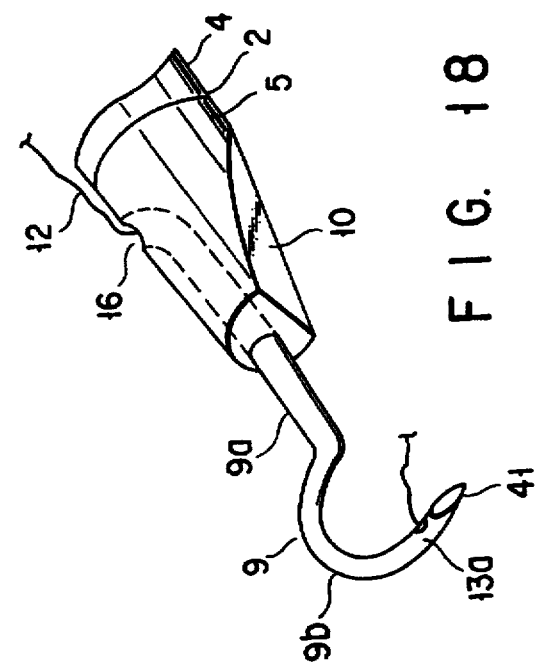
FIG. 17
FIG. 18
FIG. 19

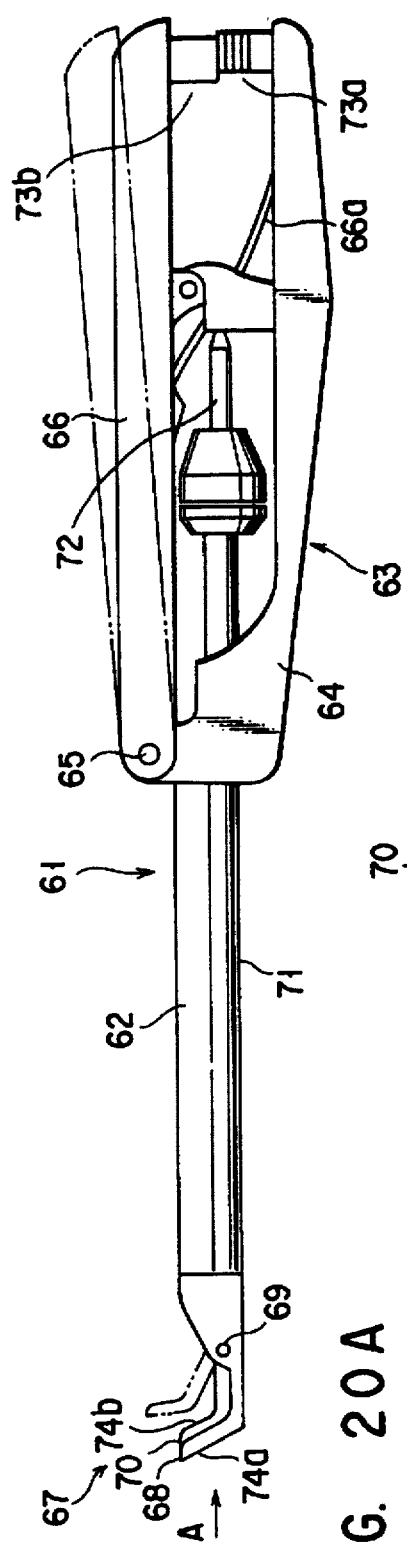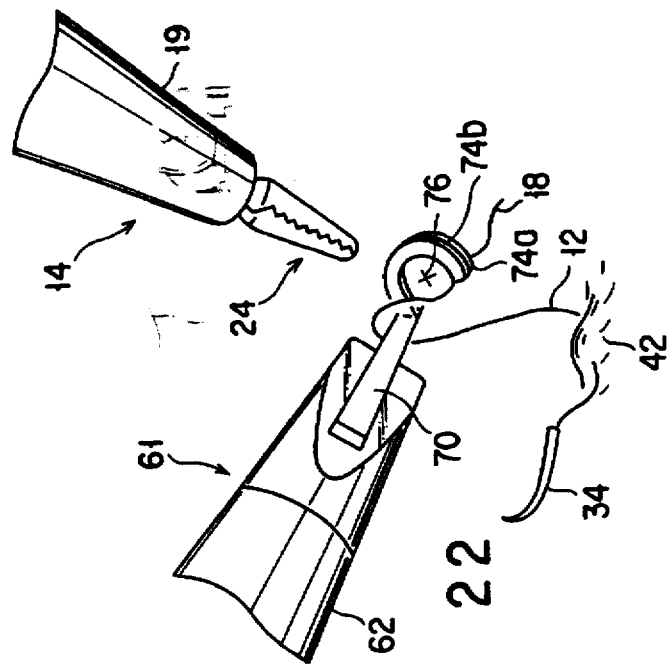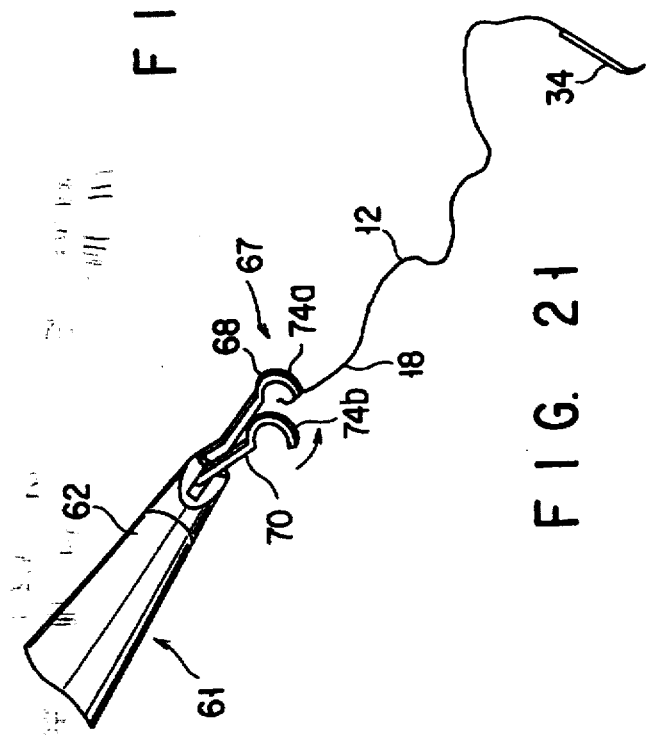

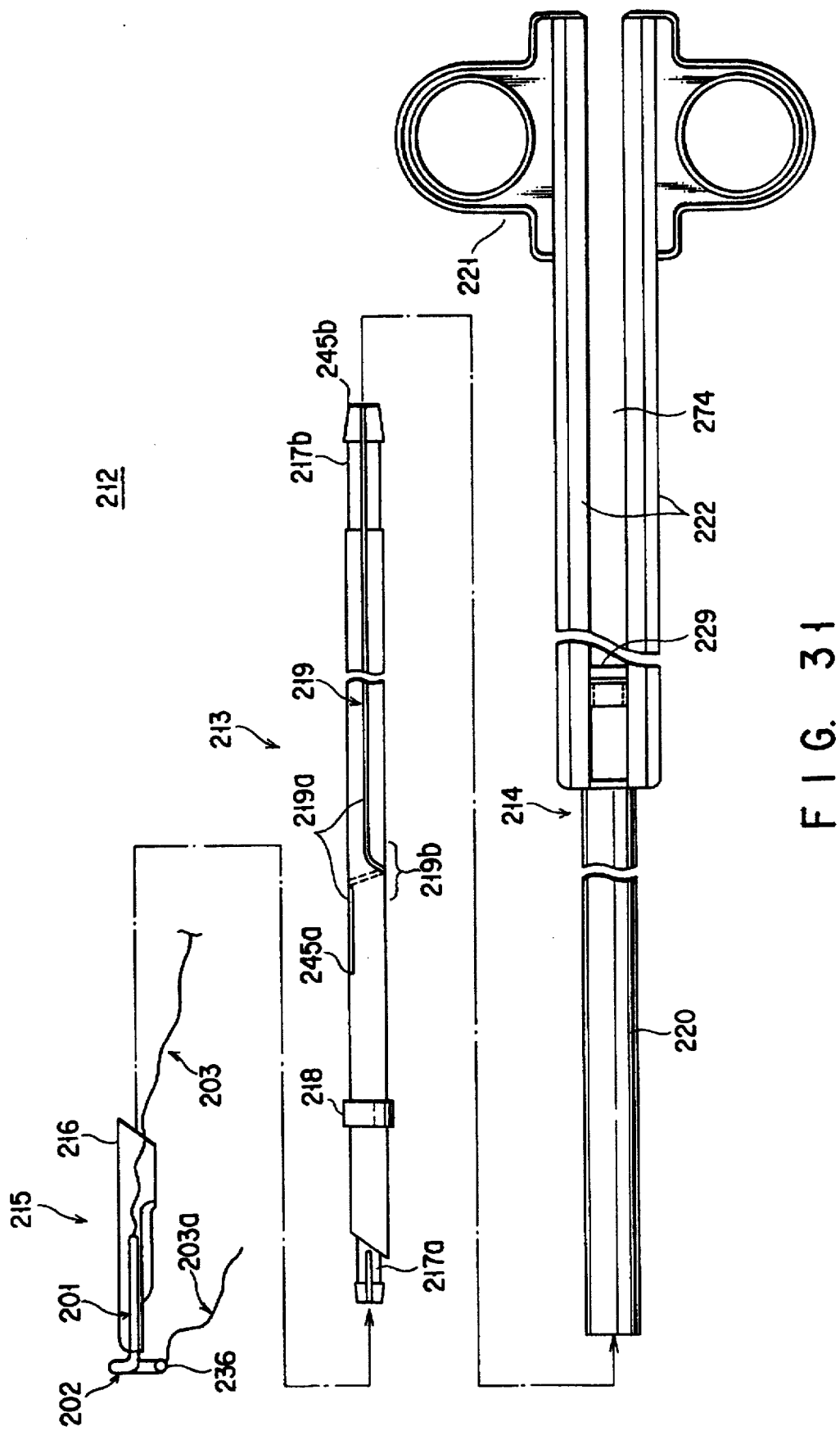
F I G. 31

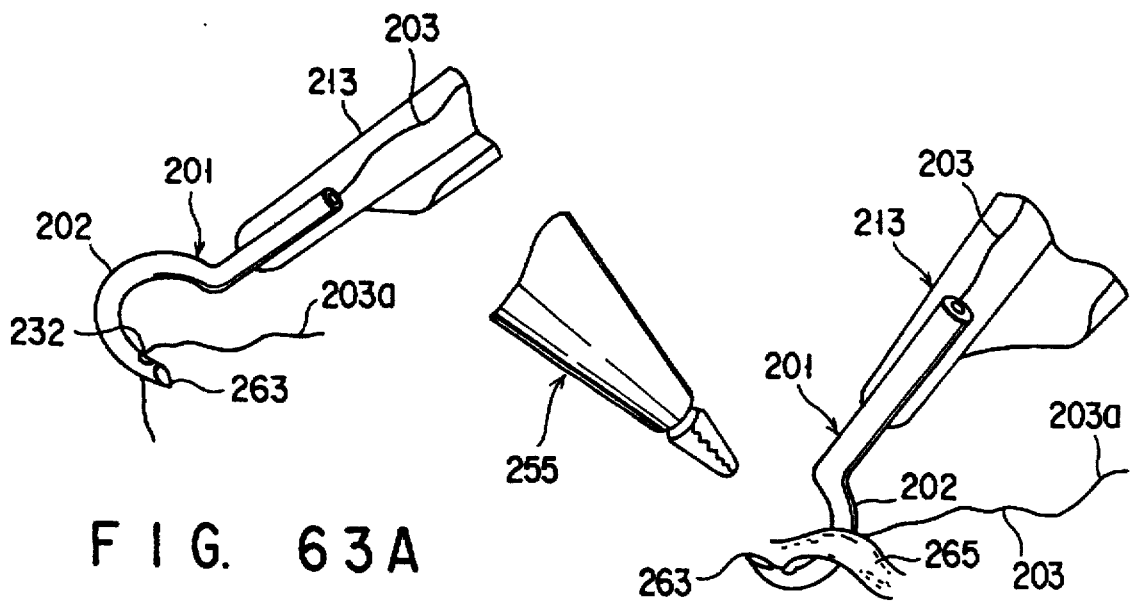
FIG. 63A
FIG. 63B
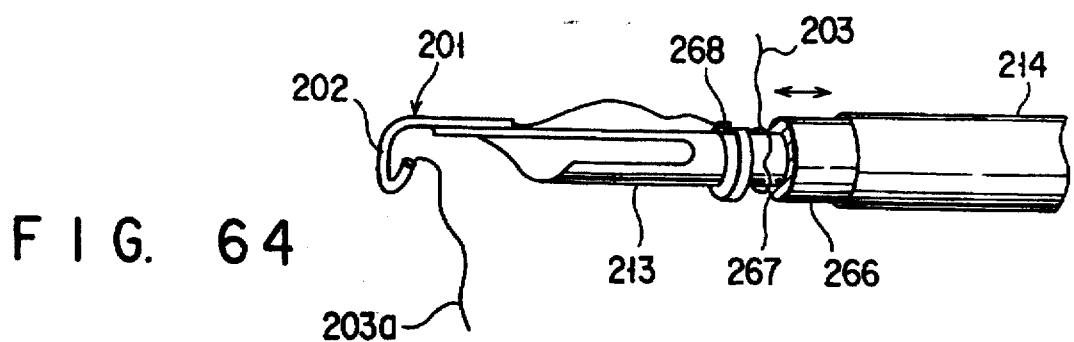
FIG. 64
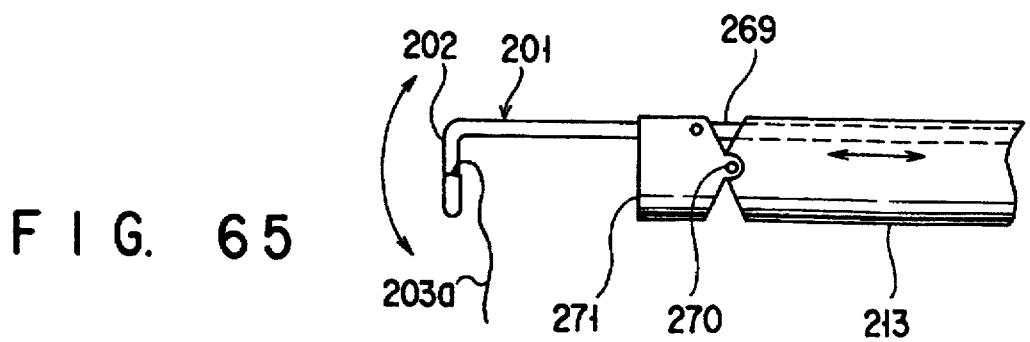
FIG. 65

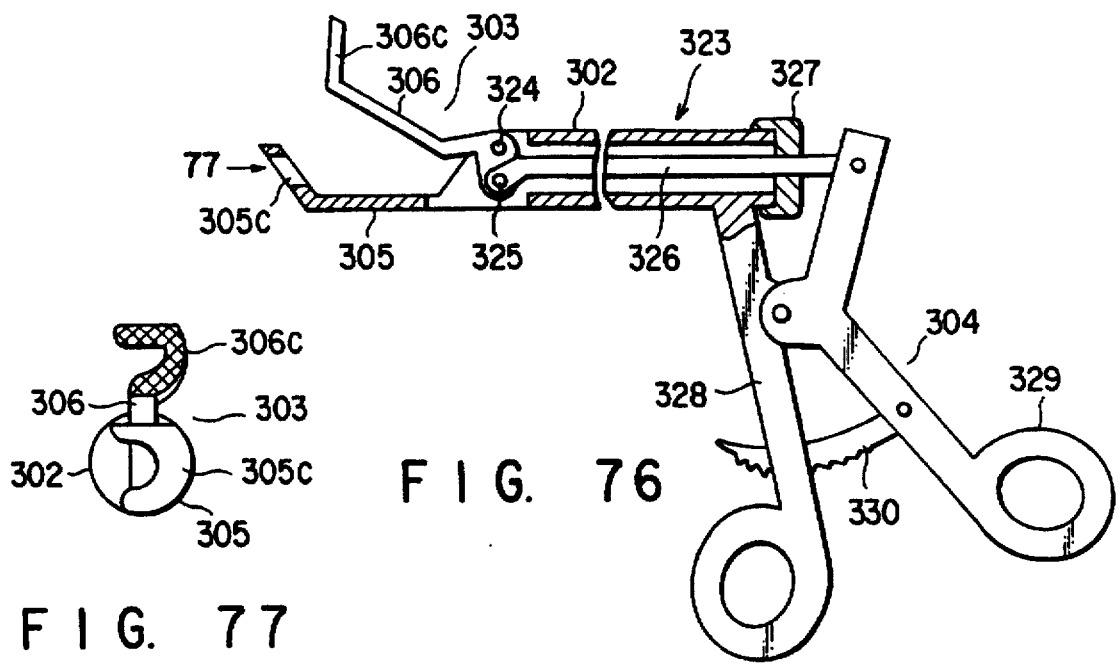
FIG. 76
FIG. 77
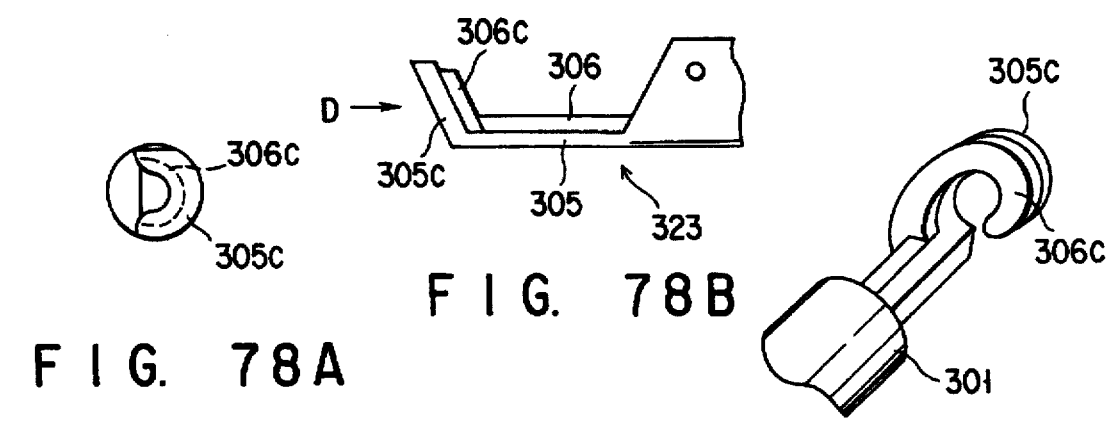
FIG. 78A
FIG. 78B
FIG. 79
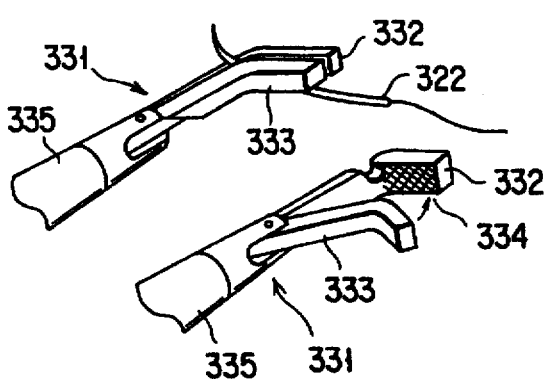
FIG. 80
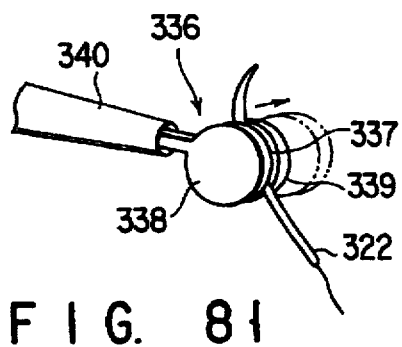
FIG. 81

LIGATING APPARATUS

BACKGROUND OF THE INVENTION

1. Field of the Invention

The present invention relates to a ligating apparatus for use in suture or ligation in surgical operations, and other medical procedures.

2. Description of the Related Art

In general, in surgical operations, procedures for ligating blood vessels and suturing body tissues are frequently performed. In particular, the operational work of required to form a knot is time-consuming.

Recently, surgical operations are performed with use of an endoscope ("endoscopic surgical operation"). In an endoscopic surgical operation, the operator ligates blood vessels or sutures body tissues, while viewing an endoscopic image displayed on a monitor. It is very difficult, however, to perform suture or ligation in a body cavity in which the space for movement is limited. In order to perform such operational works in a body cavity, various ligating devices have been developed.

Suture/litigation/procedures in endoscopic surgical operations are generally classified into:

(1) extracorporeal ligation,
(2) intracorporeal ligation, and
(3) suture/ligation with the use of a clip or a stapler.

The extracorporeal ligation is performed in the following manner. A thread is passed under a tissue of interest (i.e. a tissue for which the operational work is done), both ends of the thread are drawn out of the body, and a knot is formed outside the body. The knot is put into the body by means of a thread feed instrument called "knot pusher (knot driver)" and tightened. Normally this process is repeated several times. In this case, a "square knot" which is not easily loosened is formed by alternately changing the direction of crossing the thread.

In the intracorporeal ligation, a knot is formed by two forceps inserted into the body cavity. Of course, in the case of the intracorporeal ligation, the square knot which is not easily loosened should desirably be formed.

The suture/ligation technique with the use of the slip or stapler is advantageous in that the time-consuming works required for extracorporeal ligation and intracorporeal ligation can be omitted.

In the meantime, the extracorporeal ligation is troublesome since it requires frequent replacement and insertion/withdrawal of instruments. Furthermore, when the thread is pulled out of the body, the tissue located along the passage of the thread is grazed by the thread.

Although the suture/ligation technique with the use of the clip or stapler is less time-consuming, the apparatus for performing the suture/ligation is expensive. In addition, foreign matter such as a clip may be left in the body. Thus, the range of applications is limited. Depending on the kind and part of the body tissue, the suture/ligation technique with the use of the clip or stapler cannot be applied.

On the other hand, the intracorporeal ligation is free from the problems of the suture/ligation technique with the use of the clip/stapler and, unlike the extracorporeal ligation, the frequent insertion/withdrawal of instruments is not required. However, forceps must be handled in the body cavity or other limited space, while viewing a monitor which lacks in three-dimensional visual sensation. Thus, the intracorporeal ligation must be performed in an environment greatly different from that of an ordinary abdominal operation. The intracorporeal ligation thus requires a great deal of skill.

Under the situation, U.S. Pat. No. 5,281,236 and German Patent DE 3413744C2 propose ligating apparatuses for facilitating intracorporeal ligation.

Specifically, in the ligating apparatus of U.S. Pat. No. 5,281,236, a tubular catheter is movably passed through a long sheath. A curved portion forming a closed loop is provided at a distal end portion of the catheter projecting from a distal end portion of the sheath. One end portion of a thread or a suture thread passed through the catheter is projected from a distal end portion of the curved portion. In this structure, a knot is formed by passing a free-end portion of the suture thread projecting from the distal end portion of the curved portion through the loop of the curved portion. In addition, the curved portion is pulled into the sheath, thereby forcibly straightening the curved portion and making the knot fall from the distal end of the curved portion. After the knot is fallen, the free-end portion of the thread is pulled and the knot is tightened.

In the ligating apparatus of German Patent DE 3413744C2, a spiral coil portion is provided at a distal end portion of an elongated member. A suture thread is passed through the coil portion to form a knot. In addition, the elongated member is rotated, thereby rotating the coil portion and making the knot fall from a distal end of the coil portion. After the knot is fallen, a free-end portion of the thread is pulled to tighten the knot.

In both U.S. Pat. No. 5,281,236 or German Patent DE 3413744C2, however, the direction of forming the knot (i.e. the direction of the thread) is inevitably limited to one direction as determined by the direction of the curved closed loop or the direction of winding of the coil portion. As a result, the direction of the first knot is equal to that of the second knot. These of two half-knots are generally called "granny knot". The granny knot is loosened more easily than the above-mentioned square knot and is used less frequently.

Accordingly, when the ligating apparatus of U.S. Pat. No. 5,281,236 or German Patent DE 3413744C2, which can form the granny knot alone, is used, additional works are required to tighten the granny knot, for example, by increasing the number of knots.

In the case of the ligating apparatus of German Patent DE 3413744C2, moreover, it is difficult to pass the thread with a needle into the coil portion. In addition, in order to make the knot fall from the coil portion, it is necessary to rotate the elongated member by the number of times corresponding to the number of winding of the coil portion through which the thread is passed. These procedures are very time-consuming.

SUMMARY OF THE INVENTION

The object of the present invention is to provide a general-purpose ligating apparatus suitable for ligation and suture and capable of forming a tight knot by a simple procedure.

The object of the invention can be achieved by a ligating apparatus comprising:

a first ligating member having an insertion portion to be inserted into a living body, and a holding member with a loop portion of a shape of a partially missing closed loop, said loop portion being capable of holding at least one of a ligation thread for forming a knot and a needle; and a second ligating member having holding means capable of holding at least one of the ligation thread and the needle and capable of being passed through said loop portion, said second ligating member cooperating with said first ligating member to form a knot of the ligation thread by passing the holding means holding one end portion of the ligation thread through a knot forming loop defined by the ligation thread held by said loop portion and the loop portion.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 17 is a partially cross-sectional side view schematically showing the entire structure of a ligating apparatus according to a second embodiment of the invention;

FIG. 18 is a perspective view of the thread guide member;

FIG. 19 is a perspective view showing the state in which a distal-end needle portion of the thread guide member is directly stabbed into a tissue to be ligated;

FIG. 20A is a side view schematically showing the entire structure of a ligating apparatus according to a third embodiment of the invention;

FIG. 20B shows the ligating apparatus of FIG. 20A, as viewed in the direction of arrow A;

FIG. 21 is a perspective view showing the state in which a free-end portion of the ligation thread with a needle is held at a distal end portion of the holder within the body cavity;

FIG. 22 is a perspective view showing a quasi-loop formed of the thread holder and ligation thread;

FIG. 31 is an exploded view of the thread hooking device shown in FIG. 30;

FIG. 63A shows a distal end portion of a ligating apparatus according to a 14th embodiment of the present invention;

FIG. 63B shows the state in which a distal end portion of a knot forming member is stabbed into the body tissue by using the ligating apparatus shown in FIG. 63A;

FIG. 64 shows a distal end portion of a ligating apparatus according to a 15th embodiment of the present invention;

FIG. 65 shows a distal end portion of a ligating apparatus according to a 16th embodiment of the present invention;

FIG. 76 is a vertical cross-sectional view of a forceps apparatus according to a 18th embodiment of the invention;

FIG. 77 shows the forceps apparatus of FIG. 76, as viewed in the direction of arrow 77 in FIG. 76;

FIG. 78A is a view taken in the direction of arrow D in FIG. 78B;

FIG. 78B is a side view of first and second distal end members;

FIG. 79 is a perspective view of a distal end portion of a forceps apparatus according to a 19th embodiment of the invention;

FIG. 80 is a perspective view of a forceps apparatus with first and second rectangular-parallelepipedic distal end members;

FIG. 81 is a perspective view of a forceps apparatus with first and second disk-like distal end members;

DETAILED DESCRIPTION OF THE PREFERRED EMBODIMENTS

Figure 1:
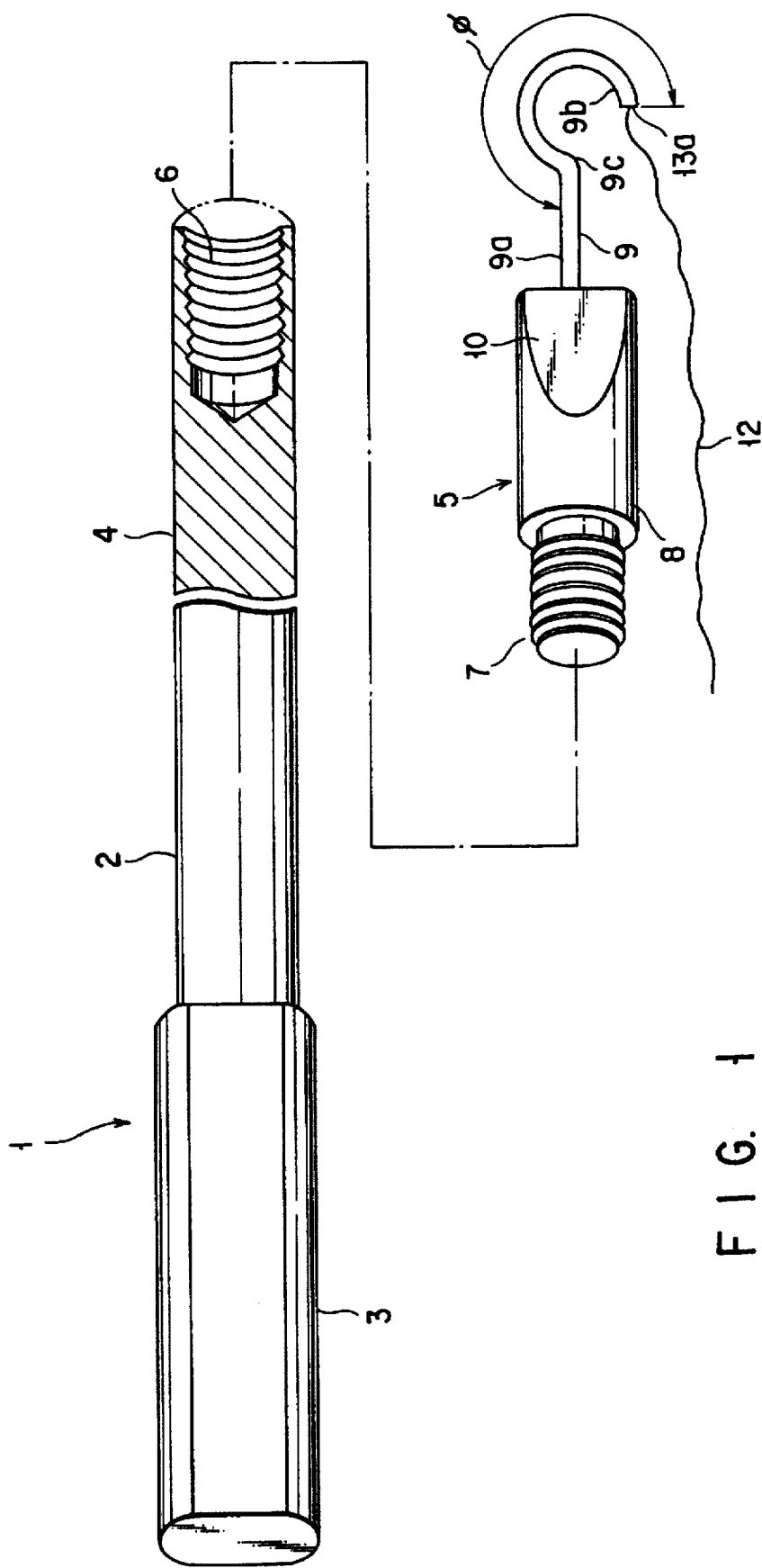
FIG. 1 is a partially cross-sectional perspective view schematically showing the entire structure of a thread holder of a ligating apparatus according to a first embodiment of the present invention.

Preferred embodiments of the present invention will now be described with reference to the accompanying drawings. FIG. 1 through FIGS. 16A and 16B show a first embodiment of the invention. As is shown in FIG. 1, a thread holder (first ligating member) 1 comprises an insertion portion 2 to be inserted into a body cavity, and a handle portion 3 coupled to a proximal end portion of the insertion portion 2. The insertion portion 2 comprises an elongated rod-like shaft portion 4, and a distal end member 5 coupled to a distal end portion of the shaft portion 4. A threaded hole 6 is formed in the distal end portion of the shaft portion 4. A male thread portion 7 is provided on a proximal end portion of the distal end member 5. The male thread portion 7 is engaged with the threaded hole 6. Thus, the distal end member 5 can be detachably attached to the shaft portion 4.

Figure 2:
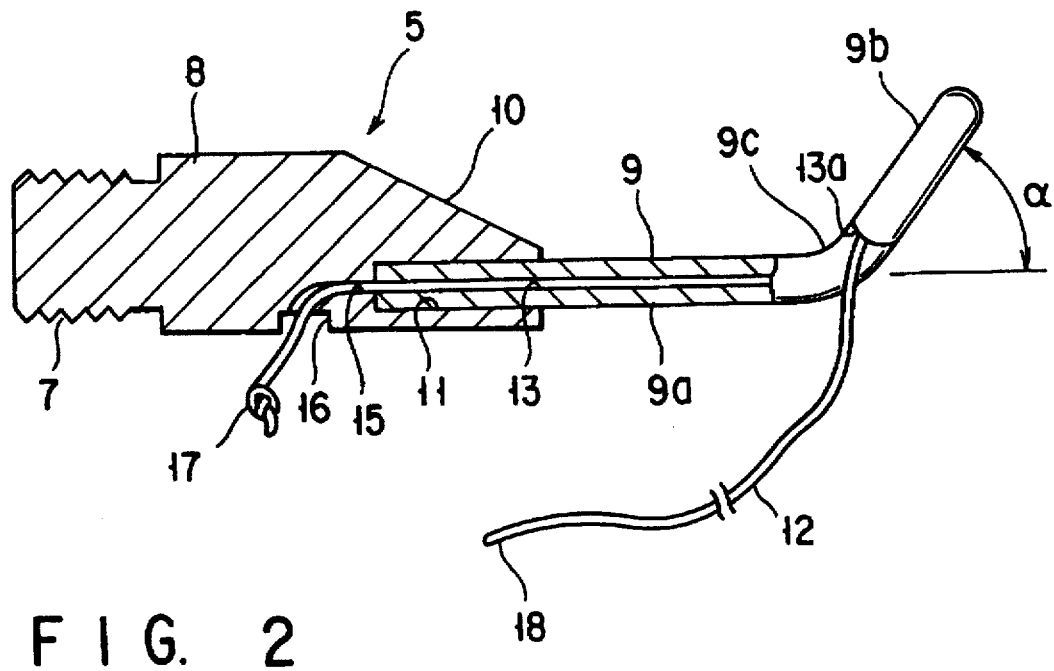
FIG. 2 is a vertical cross-sectional view showing an internal structure of a thread guide member.

The distal end member 5 comprises a substantially cylindrical distal end member body 8 and a thread guide member 9 projecting from a distal end portion of the distal end member body 8. The outer peripheral surface of the distal end portion of the distal end member body 8 is beveled, thereby forming an inclined surface 10 for preventing the visual field from being obstructed. As is shown in FIG. 2, an axially extending fixing hole 11 for fixing the thread guide member 9 is formed in the distal end portion of the distal end member body 8.

The thread guide member 9 is formed of a hollow tubular member of hard material. As is shown in FIG. 2, a first suture thread passage 13 for passing a suture thread 12 is formed in the thread guide member 9. The inside diameter of the first suture thread passage 13 is greater than the outside diameter of the suture thread 12 inserted in the first suture thread passage 13, so that the suture thread 12 can be inserted through the passage 13. The thread guide member 9 comprises a straight portion 9a extending in parallel to the axis of the insertion portion 2, and a substantially C-shaped arcuated portion 9b disposed at a distal end portion of the straight portion 9a. Specifically, the arcuated portion 9b has a partially missing or imperfect loop shape. A proximal end portion of the straight portion 9a of the thread guide member 9 is inserted and fixed in the fixing hole 11 in the distal end member body 8. A thread release port 13a for releasing the suture thread 12 to the outside is formed at the end portion of the imperfect loop of the thread guide member 9, that is, a distal end portion 9b of the arcuated portion 9b. The inside diameter and central angle φ of the arcuated portion 9b of the thread guide member 9 are determined so that a forceps 14 (described later) can be passed through the arcuated portion 9b. In the present embodiment, as shown in FIG. 1, the central angle φ of the arcuated portion 9b is set at about 270°.

A second suture thread passage 15 is formed in the distal end member body 8. One end portion of the second suture thread passage 15 communicates with the first suture thread passage 13 of the thread guide member 9, and the other end portion of the passage 15 communicates with a counterbore 16 opening to the outer peripheral surface of the distal end member body 8. The second suture thread passage 15 has the same inside diameter as the first suture thread passage 13 of the thread guide member 9.

The suture thread 12 used in the present embodiment is inserted into the first suture thread passage of the thread guide member 9 from the thread release port 13a, is passed through the second thread passage 15, and is drawn out of the counterbore 16 by a suitable length. A knot 17 is formed at the end portion of the suture thread 12 drawn out of the counterbore 16. The knot 17 is sunk and set in the counterbore 16. The counterbore 16 is slightly greater in size than the knot 17 of the suture thread 12. The diameter of the second suture thread passage 15 is set so as to prevent passage of the knot 17. Accordingly, even if a free-end portion 18 of the suture thread 12, located opposite to the knot 17, is pulled, the suture thread 12 is not removed from the distal end member body 8.

Figure 4:
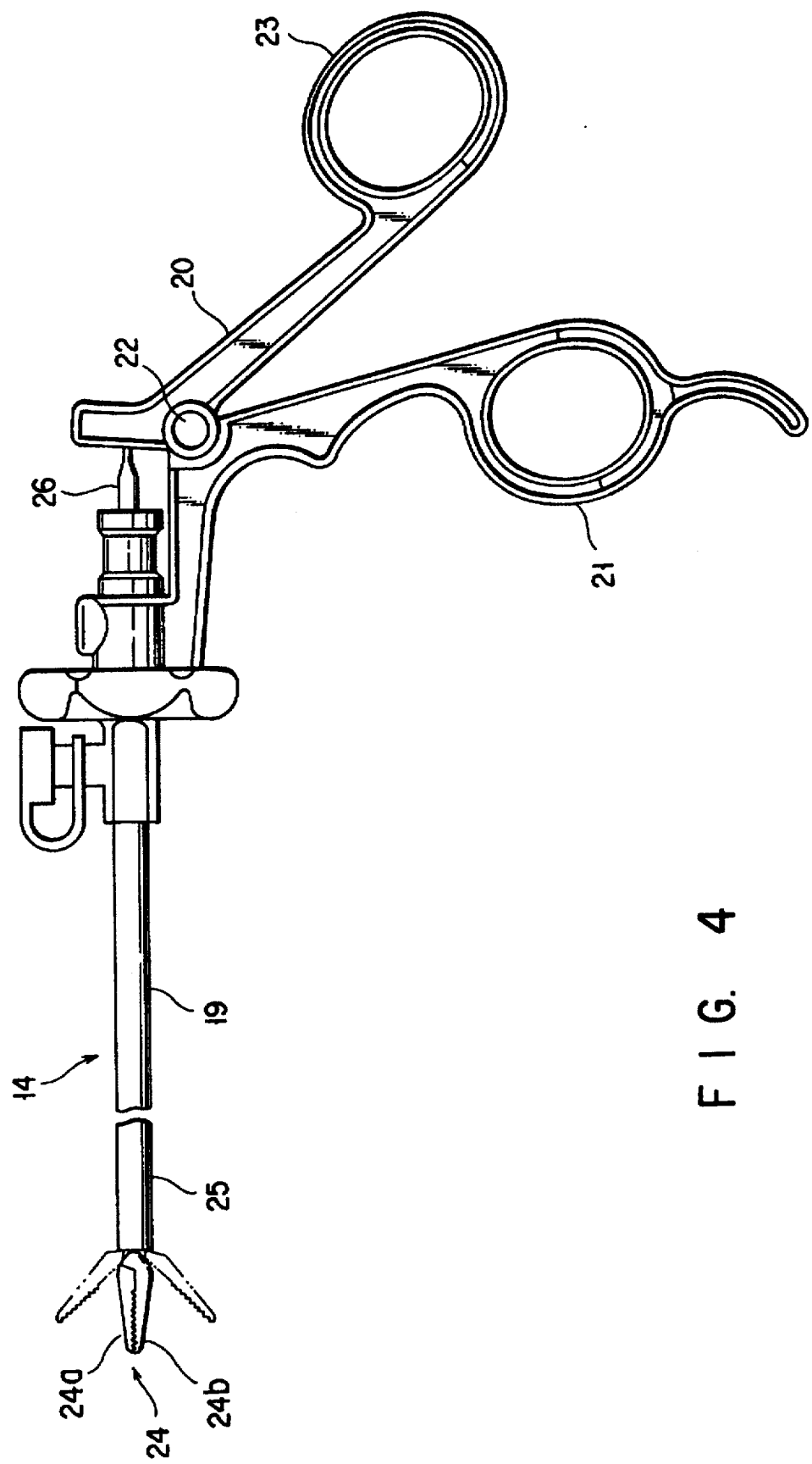
FIG. 4 is a side view showing the entire structure of a forceps.

FIG. 4 shows the forceps (second ligating member) 14 to be used in combination with the thread holder 1. The forceps 14 has the same structure as the one generally used in endoscopic surgical operations. Specifically, the forceps 14 comprises an insertion portion 19 to be inserted into the body cavity, and a handle unit 20 connected to a proximal end portion of the insertion portion 19. The handle unit 20 comprises a fixed handle 21 and a movable handle 23 rotatably coupled to the fixed handle 21 by means of a coupling pin 22. A treatment unit (holding or manipulating device) 24 is provided at a distal end portion of the insertion portion 19. The treatment unit 24 comprises a pair of holding portions 24a and 24b. The insertion portion 19 comprises a sheath 25 and an operating shaft 26 provided inside the sheath 25. A proximal end portion of the operating shaft 26 is coupled to the movable handle 23, and a distal end portion of the operating shaft 26 is coupled to the holding portions 24a and 24b by means of a opening/closing mechanism constituted by, e.g. a link mechanism. Accordingly, if the handle unit 20 is operated, the operating shaft 26 is moved forward and backward along the axis thereof, thereby opening/closing the holding portions 24a and 24b.

Figure 5:
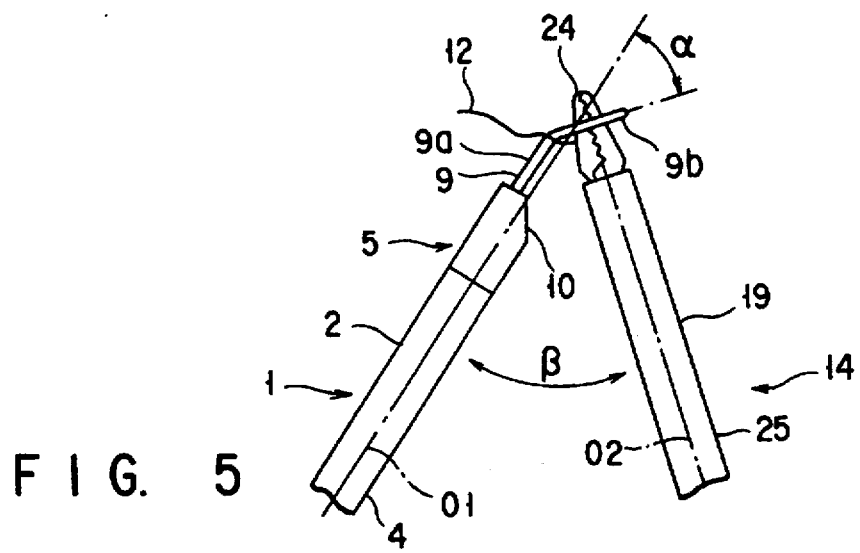
FIG. 5 is a side view of a main structure in which the forceps is inserted through a quasi-loop of the thread guide member.

As is shown in FIG. 2, the arcuated portion 9b of the thread guide member 9 is inclined at an angle α with respect to the straight portion 9a. As is shown in FIG. 5, in the state in which the treatment unit 24 of the forceps 14 is inserted through the arc of the arcuated portion 9b, the angle β between a center axis $O_1$ of the thread holder 1 and a center axis $O_2$ of the insertion portion 19 of the forceps 14 and the inclination angle α a should desirably have the following relationship:

α=90°−β

In the state of normal use, the inclination angle α of the arcuated portion 9b should desirably be between 30° and 60°.

Figure 14A:
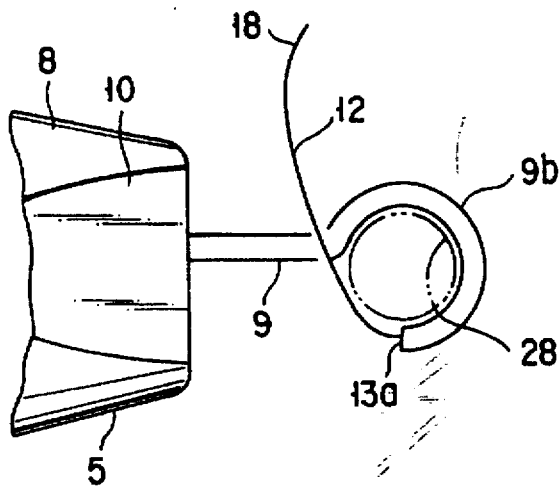
FIG. 14A is a plan view showing the state in which a quasi-loop is formed by the ligation thread which is guided through the thread guide member and pulled out of the cut-end of the thread guide member.
Figure 14B:
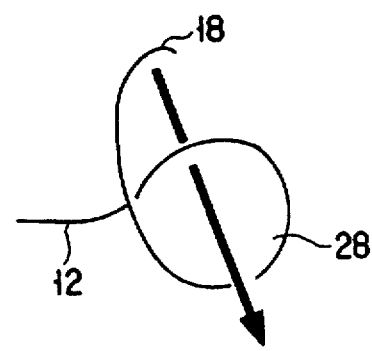
FIG. 14B is a view illustrating only the motion of the ligation thread in FIG. 14A.
Figure 16A:
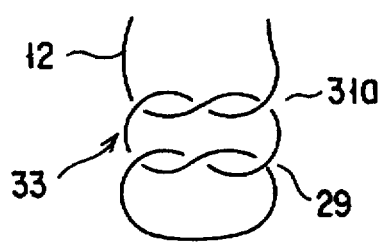
FIG. 16A illustrates a granny knot.
Figure 16B:
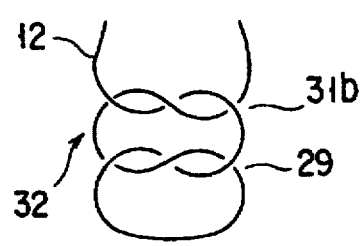
FIG. 16B illustrates a square knot.

The operation of the ligating apparatus comprising the thread holder 1 and forceps 14 will now be described. At first, a method of forming a knot of the suture thread 12 by using the thread holder 1 will be described. As is shown in FIG. 14A, the free end portion 18 of the suture thread 12 projecting from the thread release port 13a of the arcuated portion 9b of the thread guide member 9 is pulled to the cut-end side of the loop of the arcuated portion 9b, while being held, for example, between the holding portions 24a and 24b of the treatment unit 24 of the forceps 14. Thus, a quasi-loop 28 is formed by the suture thread 12 and arcuated portion 9b. From this state, the treatment unit 24 holding the free end portion 18 of the suture thread 12 is passed through the quasi-loop 28, as indicated by the arrow in FIG. 14B, thereby provisionally forming a first half-knot of the suture thread 12. Then, the provisionally formed first half-knot is fallen from the "cut-out portion" of the arcuated portion 9b (i.e. the gap between the proximal end and distal end of the arcuated portion 9b) of the thread guide member 9 and tightened, thereby forming the first half-knot 29, as shown in FIGS. 16A and 16B.

Figure 15A:
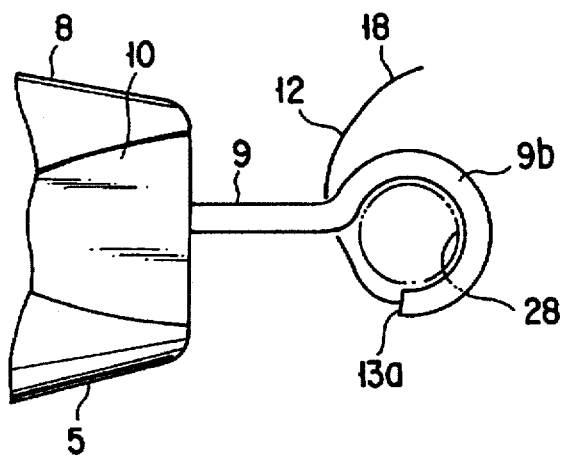
FIG. 15A is a plan view showing the state in which the free-end portion of the ligation thread is passed through the quasi-loop formed by the ligation thread guided through the thread guide member and pulled out of the cut-end of the thread guide member, in a direction opposite to that illustrated in FIG. 14A.
Figure 15B:
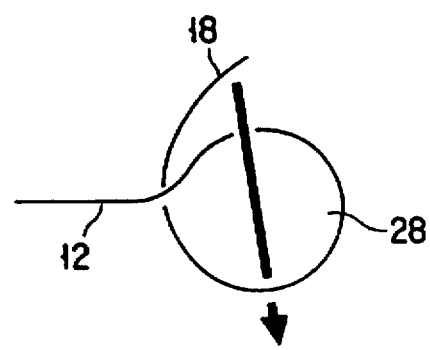
FIG. 15B is a view illustrating only the motion of the ligation thread in FIG. 15A.

Subsequently, a second half-knot is formed by passing the thread in a direction opposite to that in forming the first half-knot 29. Thus, a secure square knot 32 (see FIG. 16B) is formed. In order to form the square knot, the free end portion 18 of the suture thread 12 must be passed through the quasi-loop 28 in the opposite direction, as shown in FIGS. 15A and 15B. Specifically, the suture thread 12 is looped on the rear side of the thread guide member 9 and the free end portion 18 of the suture thread 12 is passed through the quasi-loop 28 formed by the arcuated portion 9b and arcuately extended suture thread 12 towards the rear side of the thread guide member 9. Thereby, the second half-knot 31b is formed and the square knot 32 is formed.

If the thread guide member 9 has a loop shape of more than a single winding, the direction of winding is inevitably determined. Thus, only a granny knot (see FIG. 16A) having the second half-knot 31a and first half-knot 29 formed in the same direction is obtained. In order to obtain the square knot 32, it is necessary to form the thread guide member 9 in the arcuated shape (.i.e. a part of a loop is missing) and to make the direction of winding of the suture thread 12 selectable at the time of use. If this condition is met, the half-knot formed at the arcuated portion 9b of the thread guide member 9 can be fallen from the missing portion of the loop.

A description will now be given of the case where a tubular tissue (blood vessel, etc.) is ligated ("intracorporeal ligation") by the suture thread 12 by using the ligating apparatus comprising the thread holder 1 and forceps 14.

Figure 6:
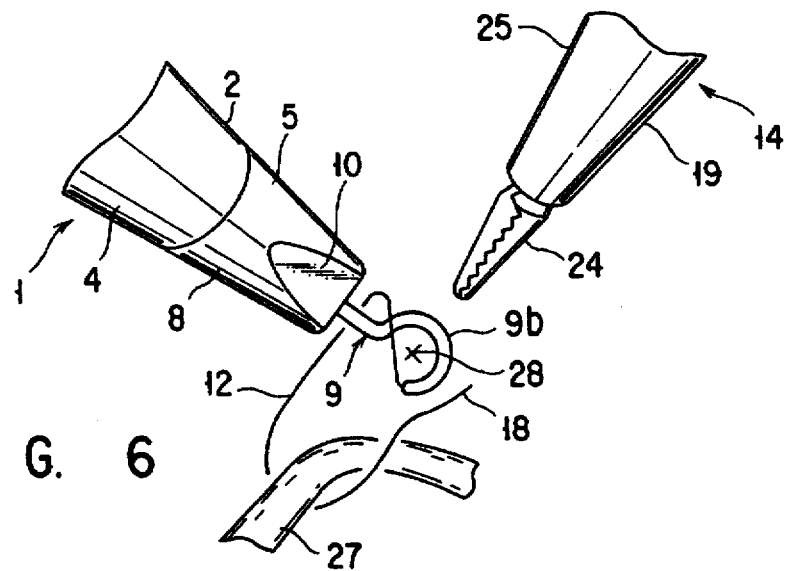
FIG. 6 is a perspective view showing the state in which the thread holder is rotated clockwise with a free-end portion of the ligation thread passed behind a tubular tissue, thereby forming a quasi-loop of the ligation thread.

The insertion portion 2 of the thread holder 1 is inserted into the patient's body under observation by an endoscope (not shown). The distal end member 5 of the insertion portion 2 is approached to the tubular tissue of interest. As is shown in FIG. 6, after tubular tissue 27 is exfoliated, the free end portion 18 of the suture thread 12 is passed behind the tubular tissue 27. In this state, the insertion portion 2 of the thread holder 1 is rotated clockwise. Thereby, the suture thread 12 is extended from the thread release port 13a of the arcuated portion 9b of thread guide member 9 towards the missing portion of the loop. In this state, as shown in FIG. 6, a quasi-loop 28 is formed by the suture thread 12 and arcuated portion 9b. At this time, the suture thread 12 is brought to the front side of the thread guide member 9.

Figure 7:
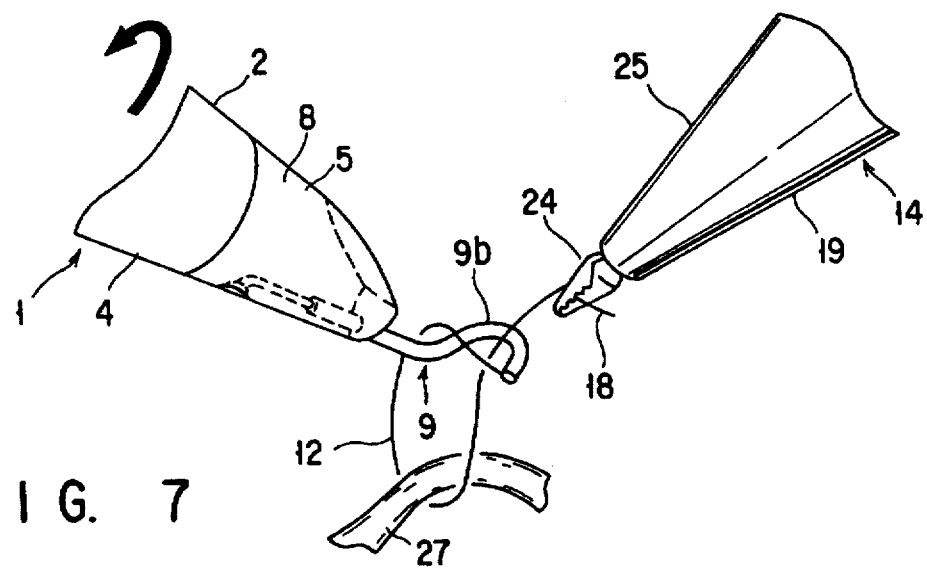
FIG. 7 is a perspective view showing the state in which a first half-knot of a knot is formed by pulling the free-end portion of the ligation thread with the forceps passed through the quasi-loop.
Figure 8:
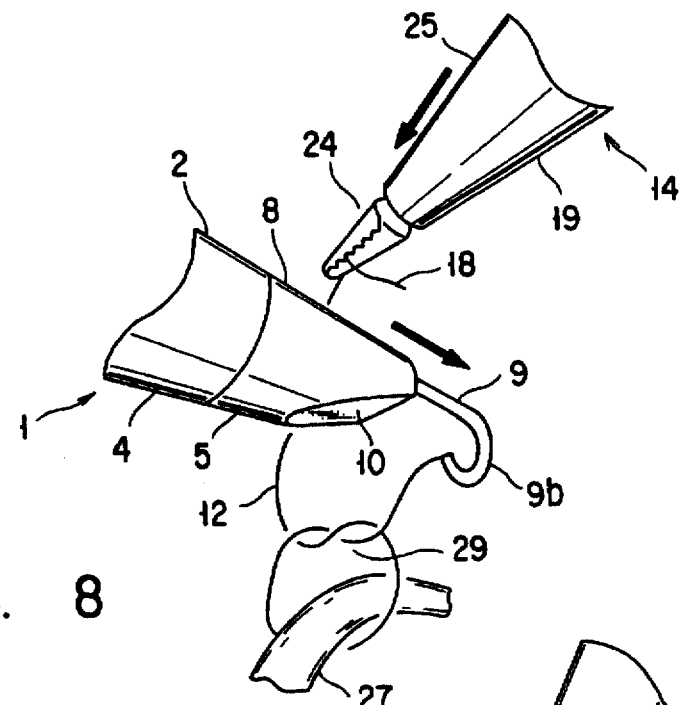
FIG. 8 is a perspective view showing the state in which the first half-knot is fallen by the thread guide member and fully tightened by crossing the thread holder and forceps, thereby completing the formation of a first half-knot of the knot.

Then, the treatment unit 24 of the forceps 14 is passed through the quasi-loop 28, and the free end portion 18 of the suture thread 12 is held by the holding portions 24a and 24b of the treatment unit 24. Subsequently, the treatment unit 24 of the forceps 14, which holds the suture thread 12, is pulled out of the quasi-loop 28. Thus, as shown in FIG. 7, the free end portion of the suture thread 12 is pulled out of the quasi-loop 28 and a first half-knot is provisionally formed. In this state, the thread holder 1 is rotated counterclockwise, as indicated by the arrow in FIG. 7, thereby falling the provisionally formed first half-knot from the thread guide member 9. Then, as shown in FIG. 8, the thread holder 1 and forceps 14 are pushed forward in mutually crossing directions. Thus, the suture thread 12 is fully tightened and the first half-knot 29 is formed.

Figure 9:
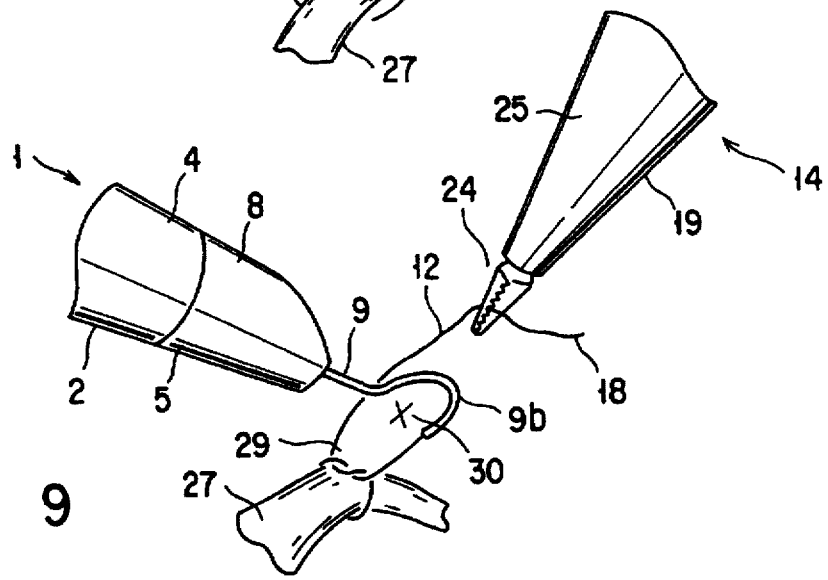
FIG. 9 is a perspective view showing the beginning state of a work of forming a second half-knot of the knot.
Figure 10:
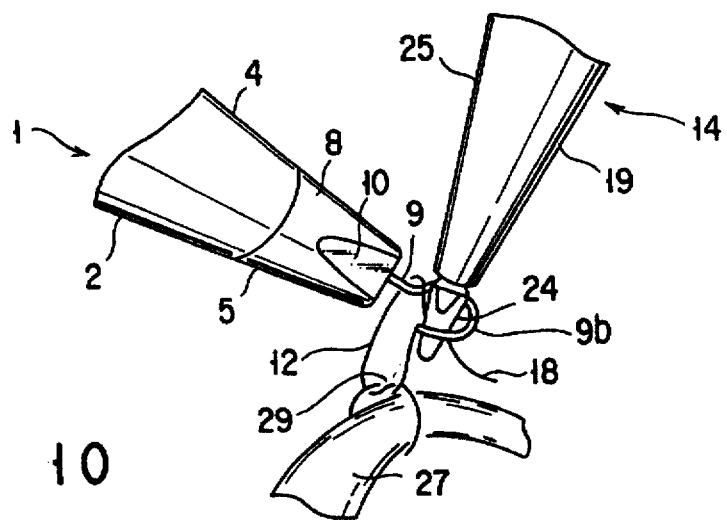
FIG. 10 is a perspective view showing the state in which the forceps is passed through a second quasi-loop, with the free-end portion of the ligation thread being held.
Figure 11:
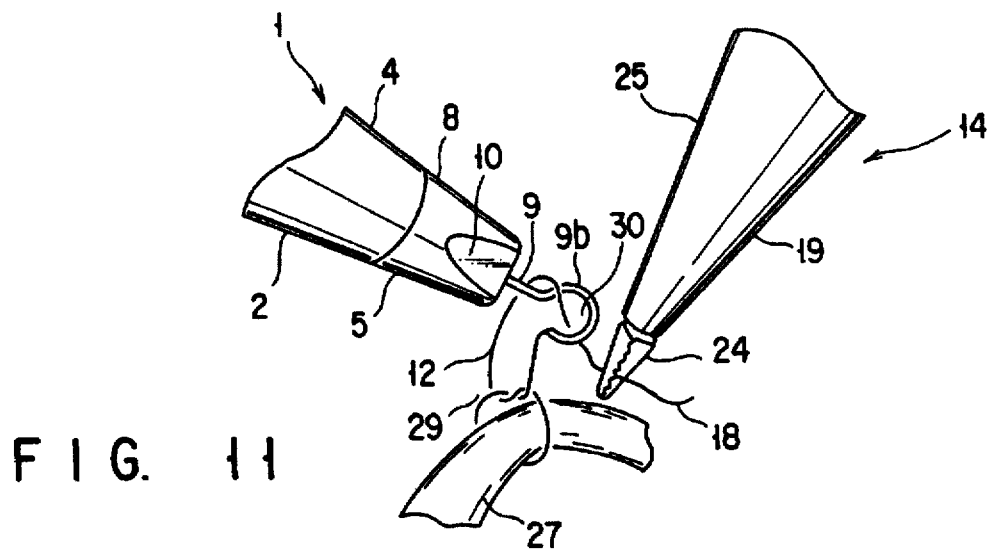
FIG. 11 is a perspective view showing the state in which the free-end portion of the ligation thread is re-held by the forceps on the rear side of the second quasi-loop.
Figure 12:
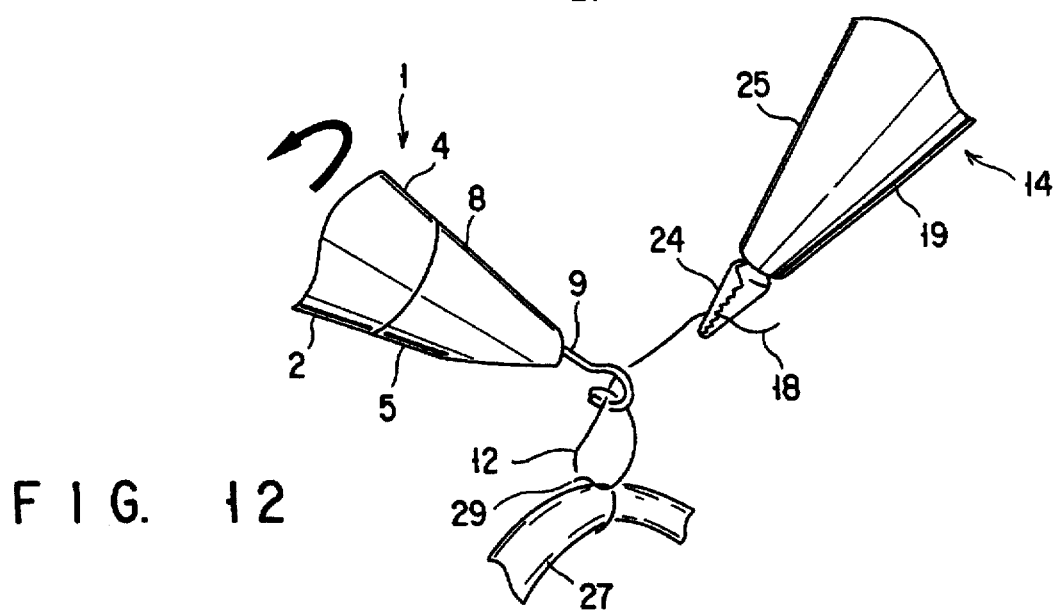
FIG. 12 is a perspective view showing the state in which the second half-knot is fallen from the thread guide member, while the thread holder is rotated counterclockwise in a similar manner with the formation of the first half-knot.
Figure 13:
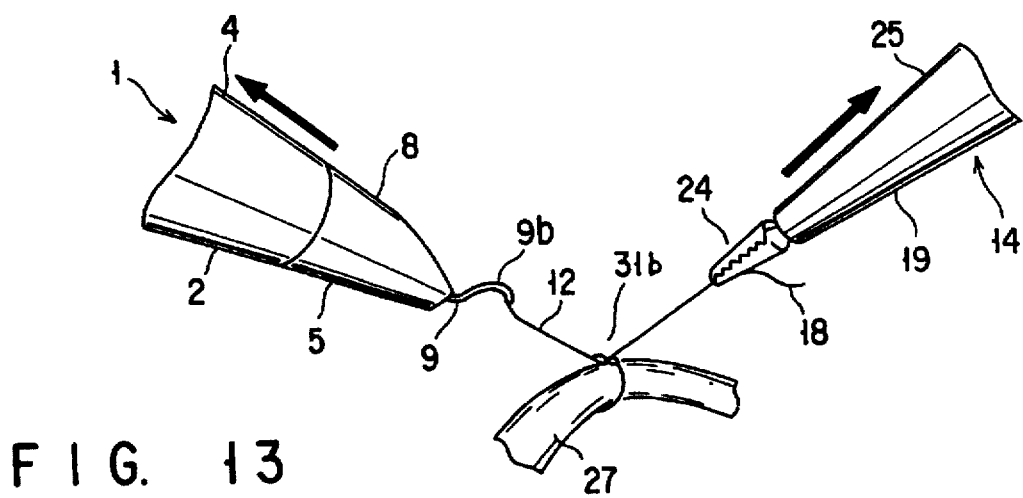
FIG. 13 is a perspective view showing the state in which the second half-knot is fully tightened and formed.

After the first half-knot 29 is formed, the free end portion 18 of the suture thread 12 is held by means of the treatment unit 24 and a second quasi-loop 30 is formed of the suture thread 12 and the arcuated portion 9b of the thread guide member 9, as shown in FIG. 9. At this time, attention should be paid so that the suture thread 12 is located behind the thread guide member 9. Then, as shown in FIG. 10, the treatment unit 24 holding the suture thread 12 is passed through the second quasi-loop 30 and the holding portions 24a and 24b of the treatment unit 24 are opened to release the free end portion 18 of the suture thread 12 from the treatment unit 24. Subsequently, the treatment unit 24 of the forceps 14 is pulled out of the quasi-loop 30 and, as shown in FIG. 11, the free end portion 18 of the suture thread 12 is held once again by the treatment unit 24 on the rear side of the second quasi-loop 30. Thereafter, like the formation of the first half-knot 29, the thread holder 1 is rotated counterclockwise, as indicated by the arrow in FIG. 12, and a provisionally formed second half-knot is fallen from the thread guide member 9. The thread holder 1 and forceps 14 are pulled, as indicated by the arrows in FIG. 13, and the provisionally formed second half-knot is tightened. Thus, the second half-knot 31b is formed.

Figure 3:
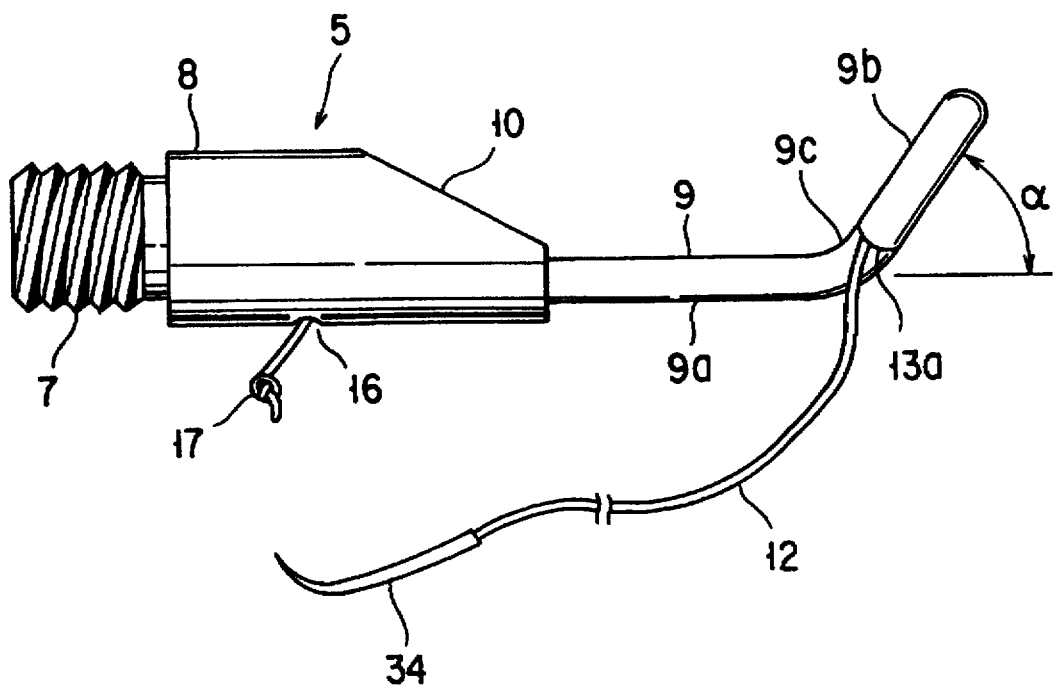
FIG. 3 is a side view of a distal end member body used along with a ligation thread with a needle.

The thus formed knot of the suture thread 12 is called a square knot having high ligative strength, which comprises the first half-knot 29 and second half-knot 31b formed in reverse directions, as shown in FIG. 16B. If the above procedure is repeated on an as-needed basis, a securer knot can be obtained. The above-described ligative procedure is applicable to suture of tissues. In the case of the suture, a suture needle 34 is attached to the free end portion 18 of the suture thread 12, as shown in FIG. 3.

In the present embodiment, the arcuated portion 9b of the thread guide member 9 is wound clockwise, as viewed from the front side, and the thread guide member 9 is approached from the left side of the tissue. Needless to say, however, the same operation and advantage can be obtained even if the direction of winding of the arcuated portion 9b of thread guide member 9 and the direction of approach to the tissue are different from those in the present embodiment. When the ligating apparatus of the present embodiment is used in an endoscopic surgical operation, it is desirable that the outside diameter of the arcuated portion 9b of the thread guide member 9 be less than that of the insertion portion 2.

As has been described above, the ligating apparatus of the present embodiment, as compared to the conventional ligating apparatus, has a simpler structure, is easier to handle, and makes it possible to form the secure square knot 32. In addition, in the ligating apparatus of the present embodiment, as shown in FIG. 2, the arcuated portion 9b of the thread guide member 9 of thread holder 1 is bent at an angle α with respect to the straight portion 9a. Thus, the treatment unit 24 of the forceps 14 can be easily passed through the quasi-loop formed by extending the suture thread 12 from the arcuated portion 9b of the thread guide member 9 toward the missing portion of the loop. Furthermore, the provisional half-knot formed on the arcuated portion 9b of the thread guide member 9 can be easily fallen from the arcuated portion 9b.

FIGS. 17 to 19 show a second embodiment of the invention. In this embodiment, as shown in FIG. 18, a sharp needle portion 41 is formed at a distal end portion of the arcuated portion 9b of thread guide member 9. Thus, as shown in FIG. 19, the distal end of the arcuated portion 9b can be smoothly stabbed into a tissue 42 of interest by virtue of the sharp needle portion 41. A thread release port 13a is formed at an outer peripheral portion of the arcuated portion 9b near the needle portion 41. Thus, the suture thread 12 extended from the thread release port 13a is not cut by the needle portion 41.

In addition, as shown in FIG. 17, the suture thread 12 is inserted into a first suture thread passage 13 of the thread guide member 9 from the thread release port 13a and guided out from a counterbore 16 in the outer peripheral surface of the distal end member body 8. The suture thread 12 is then guided to the handle portion 3 along the insertion portion 2. The handle portion 3 is provided with a thread engaging portion 43 for disengageably engaging the suture thread 12. The thread engaging portion 43 has an operating knob 44 provided on the handle portion 3. An insertion port 45, through which the suture thread 12 can pass, is formed in a front end portion of the operating knob 44. An abutment portion 46 extending obliquely downward from the front end of the insertion port 45 is provided on a lower surface of the operating knob 44. A slide-guide projection 47 is provided at a rear end portion of the operating knob 44. A recess-like guide groove 48 extending in parallel to the axis of the handle portion 3 is formed in the outer peripheral surface of the handle portion 3. The projection 47 of the operating knob 44 is inserted in the guide groove 48, and a coil spring 49 for urging the projection 47 to the rear side of the guide groove 48 is mounted in the guide groove 48. A distal-end edge portion of the handle portion 3 is provided with an abutment surface 50 upon which the abutment portion 46 of the operating knob 44 abuts.

When the suture thread 12 is engaged with the thread engaging portion 43 having the above structure, the operating knob 44 is pushed forward against the urging force of the coil spring 49 and the insertion port 45 of the operating knob 44 is located in front of the handle portion 3. In this state, the suture thread 12 is passed through the insertion port 45 and the operating force of the handle portion 3 is released. The operating knob 44 is moved backward by the urging force of the coil spring 49 and the abutment portion 46 of the operating knob 44 abuts on the abutment surface 50 of the handle portion 3. Thereby, the suture thread 12 is engaged between the abutment portion 46 of the operating knob 44 and the abutment surface 50 of the handle portion 3. Inversely, the engagement of the suture thread 12 can be released by sliding the operating knob 44 forward against the urging force of the coil spring 49. In the state in which the engagement of the suture thread 12 is released, the suture thread 12 is not separated from the abutment surface 50 of the handle portion 3. Thus, the suture thread 12 of necessary length can be pulled out of the thread release port 13a of the thread guide member 9 on an as-needed basis and then the suture thread 12 can be engaged once again. The ligating apparatus of the second embodiment has the same structure as the ligating apparatus of the first embodiment, except for the above-described characterizing structural feature.

The operation of the ligating apparatus of the second embodiment will now be described. At first, the suture thread 12 is pulled out of the thread release port 13a of the thread holder 1 by about 1 cm to 2 cm. In this state, the sharp needle portion 41 of the arcuated portion 9b is directly stabbed into the tissue 42 to be ligated, an injured part, as shown in FIG. 19. In the state in which the thread release port 13a of the arcuated portion 9b is completely penetrated through the tissue 42, the suture thread 12 near the thread release port 13a is held by the treatment unit 24 of the forceps 14 and the free end portion 18 of the suture thread 12 is pulled out of the tissue 42.

While the free end portion 18 of the suture thread 12 is being held by the treatment unit 24 of forceps 14, the arcuated portion 9b of the thread guide member 9 is removed from the tissue 42. If the length of the pulled-out suture thread 12 is short, the operating knob 44 on the handle portion 3 is slid forward, as mentioned above, to release the suture thread 12 and the length of the pulled-out suture thread 12 is adjusted to a desired value. Thereafter, a knot of the suture thread 12 is formed in all the same manner as in the first embodiment, thereby ligating the tissue 42. After the tissue 42 has been ligated, the suture thread 12 is cut with the knot left. Thereby, the suture thread 12 is restored to the initial set state in the thread holder 1. Accordingly, the suture/ligation of the intracorporeal body tissue 42 can be repeated any number of times with the thread holder 1 left in the body.

FIGS. 20A to 22 show a third embodiment of the invention. As is shown in FIG. 20A, a thread holder 61 of a ligating apparatus of this embodiment comprises an insertion portion 62 to be inserted into the body cavity, and a handle portion 63 coupled to a proximal end portion of the insertion portion 62. The handle portion 63 comprises a fixed handle 64 and a movable handle 66 coupled rotatably to the fixed handle 64 by means of a coupling pin 65. A distal end portion of the insertion portion 62 is provided with a thread holding member (thread guide member) 67. The thread holding member 67 comprises a fixed holding portion 68 and a movable holding portion 70 coupled rotatably to the fixed holding portion 68 by means of a coupling pin 69. The insertion portion 62 comprises a sheath 71 and an operating shaft 72 provided within the sheath 71. A proximal end portion of the operating shaft 72 is coupled to the movable handle 66, and a distal end portion of the operating shaft 72 is coupled to the movable holding portion 70 by means of an opening/closing mechanism constituted by, for example, a link mechanism, etc. Accordingly, if the movable handle 66 of the handle portion 63 is operated, the operating shaft 72 is axially moved forward and backward and the movable holding portion 70 is rotated about the pin 69 relative to the fixed holding portion 68 in interlock with the movement of the operating shaft 72. Thus, the thread holding member 67 is opened and closed. A plate spring 66a for urging the movable handle 66 away from the fixed handle 64 (i.e. in such a direction as to open the handle portion 63) is interposed between the fixed handle 64 and movable handle 66. Ratchets 73a and 73b are projected from the fixed handle 64 and movable handle 66, respectively. The ratchets 73a and 73b are meshed with each other to maintain the closed state of the thread holding member 67.

Distal end portions of the fixed holding portion 68 and movable holding portion 70 of the thread holding member 67 are provided with substantially C-shaped arcuated portions 74a and 74b (i.e. having partially missing loop shapes), respectively. The shapes and the rotating mechanism of both holding portions 68 and 70 are designed such that the outer shape of the thread holding member 67 is substantially equal to that of the thread guide member 9 of the first embodiment when the fixed holding portion 68 and movable holding portion 70 are completely put in contact with each other. When the thread holding member 67 is completely closed, a thread holding face 75 is formed by a contact face between the fixed holding portion 68 and movable holding portion 70. The thread holding face 75 is provided with mesh-like anti-slip grooves to prevent slip of the held suture thread 12. The forceps 14 of the ligating apparatus of this embodiment is the same as that of the first embodiment.

The operation of the ligating apparatus of this embodiment will now be described. At first, as shown in FIG. 21, a free end portion of the suture thread 12 with a distal end portion connected to a needle 34 is held between the distal end portions of the fixed holding portion 68 and movable holding portion 70 within the body cavity. This holding state is maintained by meshing the ratchets 73a and 73b. In this state, as shown in FIG. 22, the needle 34 is penetrated through the tissue 42 of interest by using the forceps 14. Alternatively, after the needle 34 has been penetrated through the tissue 42, the free end portion 18 of the suture thread 12 is held by the thread holder 67. This state is substantially equal to the state in the first embodiment in which the suture thread 12 is set in the thread guide member 9. Accordingly, if a quasi-loop 76 is formed by the thread holding member 67 and suture thread 12, as shown in FIG. 22, the subsequent work can be performed by the same procedure as in the first embodiment.

As has been described above, the thread holder 61 of this embodiment has the same advantage as the thread holder of the first embodiment and can hold the tissue 42 in the body. Therefore, the ligating apparatus of this embodiment is applicable to various uses. According to the ligating apparatus of this embodiment, as described above, the ligating work can be performed with use of the suture thread 12 with needle 34. Needless to say, however, when the tubular tissue 27 is ligated, as in the first embodiment, the suture thread 12 without needle 34 can be used.

Figure 23:
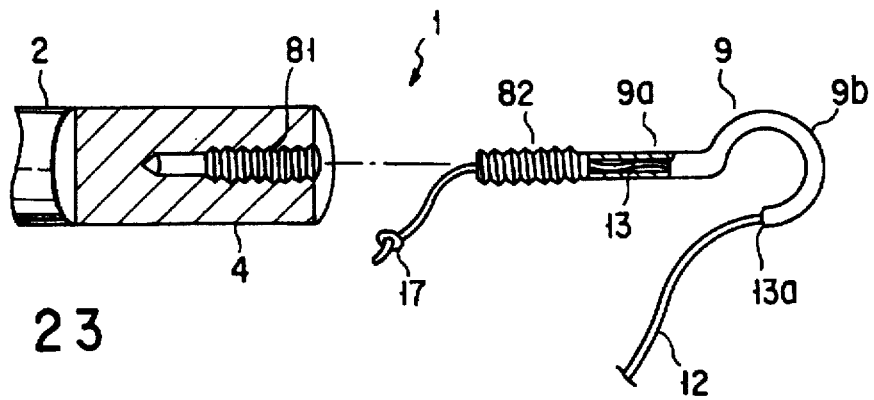
FIG. 23 is a partially cross-sectional perspective view showing the structure of a main part of a ligating apparatus according to a fourth embodiment of the invention.

FIG. 23 shows a fourth embodiment of the invention. The thread holder 1 of this embodiment differs from that of the first embodiment with respect to only the structure of the distal end portion of the insertion portion 2 thereof. Specifically, in this embodiment, a male thread portion 82 provided on a proximal end portion of a straight portion 9a of the thread guide member 9 is engaged with a threaded hole 81 formed in a distal end portion of a shaft portion 4 of the insertion portion 2. Thereby, a thread guide member 9 is fixed to the insertion portion 2. In addition, the suture thread 12 is fixed in the following manner. The suture thread 12 is inserted into a first suture thread passage 13 of the thread guide member 9, a knot 17 greater in size than the inside diameter of the first suture thread passage 13 is formed at an end portion of the suture thread 12 projecting from the first suture thread passage 13, the knot 17 is buried in the threaded hole 81 in the insertion portion 2, and the male thread portion 82 of the thread guide member 9 is engaged in the threaded hole 81. Thus, the suture thread 12 is fixed.

According to the structure of this embodiment, unlike the first embodiment, there is no need to separately provide the distal end member body 8 removably coupled to the shaft member 4 of the insertion portion 2. Therefore, the number of replacement parts is reduced and the cost is low.

Figure 24A:
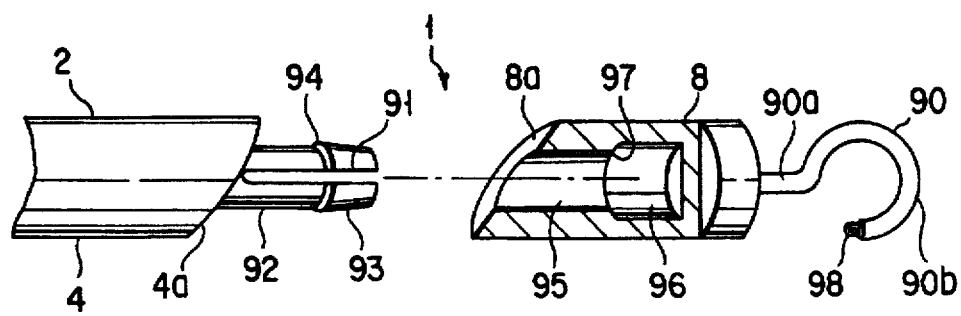
FIG. 24A is a partially cross-sectional perspective view showing the structure of a main part of a ligating apparatus according to a fifth embodiment of the invention.
Figure 24B:
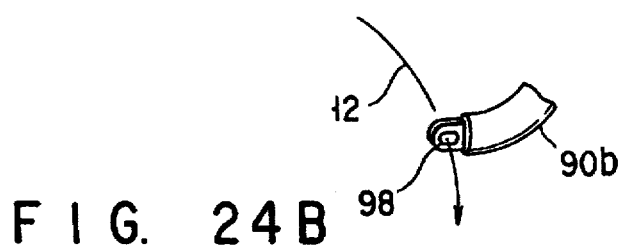
FIG. 24B is a perspective view showing a ligation thread insertion portion of the thread guide member.

FIGS. 24A and 24B show a fifth embodiment of the invention. In this fifth embodiment, the thread guide member 9 of the thread holder 1 in the first embodiment is replaced with a solid thread guide member 90, and the method of attaching/removing the distal end member body 8 and the method of fixing the suture thread 12 to the thread guide member 9 are modified. The fifth embodiment is identical with the first embodiment with respect to the other structural features.

In the fifth embodiment, a beveled surface 4a is formed at a distal end portion of the shaft portion 4 of the insertion portion 2. A resilient pipe 92, which extends coaxially with the shaft portion 4 and can deform inward by virtue of a notched groove 91, is fixed to the beveled surface 4a of the distal-end side shaft portion 4. A large-diameter portion 93 with an increased wall thickness is formed at the distal end of the pipe 92. The longitudinal length of the large-diameter portion 93 is about several mm. A stepped portion 94 is provided between the large-diameter portion 93 and the other part of the pipe 92.

A beveled surface 8a to be mated with the beveled surface 4a of the shaft portion 4 is formed at a proximal end of the distal end member body 8. An elongated hole 95, into which the pipe 92 of the shaft portion 4 is to be inserted, is formed in a proximal end portion of the distal end member body 8 along the axis thereof. A large-diameter hole portion 96 is defined at a bottom portion of the elongated hole 95. The large-diameter hole portion 96 is shaped such that the large-diameter portion 93 of the pipe 92 can be fitted in the hole portion 96. A stepped portion 97 is provided between the large-diameter hole portion 96 and the other portion of the elongated hole 95.

When the distal end member body 8 is attached to the shaft portion 4 of the insertion portion 2, the large-diameter portion 93 of the pipe 92 of the shaft portion 4 is inserted into the elongated hole 95 in the distal end member body 8 while being bent inwardly. Thus, the insertion portion 2 and distal end member body 8 are coaxially arranged. If the pipe 92 is further inserted into the elongated hole 95 and the large-diameter portion 93 of the pipe 92 is fitted in the large-diameter hole portion 96 in the distal end member body 8, the large-diameter portion 93 of the pipe 92 restores to its original shape and the stepped portion 94 of the pipe 92 abuts upon the stepped portion 97 of the elongated hole 95. Thus, the distal end member body 8 is axially fixed to the insertion portion 2. In the state in which the distal end member body 8 is attached to the shaft portion 4 of the insertion portion 2, the beveled surface 4a of the shaft portion 4 abuts upon the beveled surface 8a of the distal end member body 8. Thus, the rotation of the distal end member body 8 relative to the insertion portion 2 is prevented.

The solid thread guide member 90 comprises a straight portion 90a and a substantially C-shaped arcuated portion 90b (i.e. having a partially missing loop shape) provided at a distal end portion of the straight portion 90a. A proximal end portion of the straight portion 90a of the thread guide member 90 is fixed to the distal end member body 8. As is shown in FIG. 24B, an insertion hole 98 for insertion of the suture thread 12 is formed at a distal end portion of the arcuated portion 90b. The suture thread 12 is passed through the insertion hole 98 in the arcuated portion 90b and bound and fixed.

Figure 25:
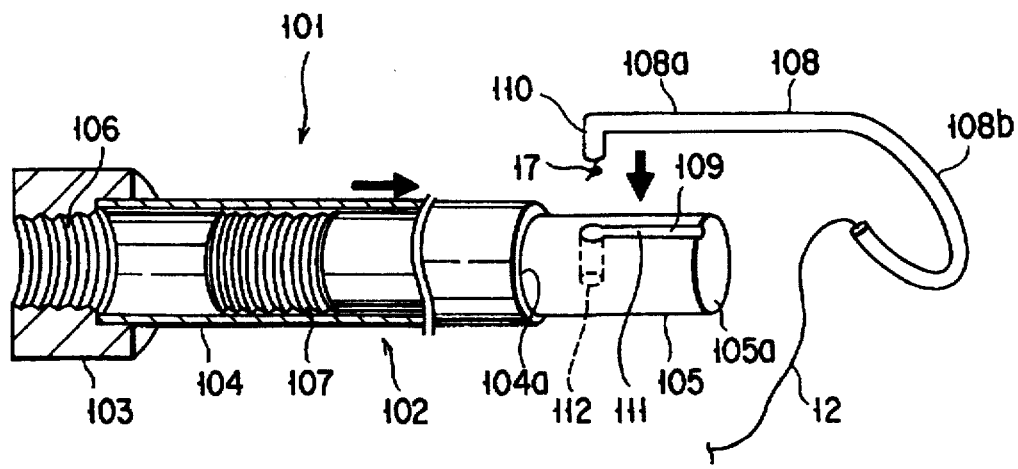
FIG. 25 is a partially cross-sectional perspective view showing the structure of a main part of a sixth embodiment of the invention.

FIG. 25 shows a sixth embodiment of the invention. A thread holder 101 of a ligating apparatus according to this embodiment comprises an insertion portion 102 to be inserted into the body cavity, and a handle portion 103 coupled to a proximal end portion of the insertion portion 102. A proximal end portion of a fixed pipe 104 is attached to a distal end portion of the handle portion 103. A shaft portion 105 of the insertion portion 102 can be inserted into the fixed pipe 104. A threaded hole 106, in which a male thread portion 107 formed on a proximal end portion of the shaft portion 105 is engaged, is axially formed in the distal end portion of the handle portion 103. The length of the fixed pipe 104 and the length of the shaft portion 105 of the insertion portion 102 are determined such that the male thread portion 107 of the shaft portion 105 finishes to be meshed with the threaded hole 106 of the handle portion 103 when the shaft portion 105 has been pulled into the fixed pipe 104 and their end faces 104a and 105a have become flush with each other.

An attachment groove 109 in which a thread guide member 108 is mounted is formed at the distal end portion of the shaft member 105 of the insertion portion 102. The thread guide member 108 is formed of a hard hollow tubular member. The thread guide member 108 comprises a straight portion 108a and a substantially C-shaped arcuated portion 108b (i.e. having a partially missing loop shape) provided at a distal end portion of the straight portion 108a. An L-shaped bent portion 110 is provided at a proximal end portion of the straight portion 108a.

The attachment groove 109 of the shaft portion 105 comprises an elongated groove 111 for receiving the straight portion 108a of the thread guide member 108, and a radial groove 112 extending perpendicularly from a terminal end of the elongated hole 111 and receiving the bent portion 110 of the thread guide member 108.

When the thread holder 101 is used, the suture thread 12 is passed through the thread guide member 108 and a knot 17 is formed at an end portion of the suture thread 12 projecting from a proximal end of the thread guide member 108. Thus, the suture thread 12 is accommodated and fixed in the thread guide member 108. Then, the bent portion 110 and straight portion 108a of the thread guide member 108 are put into the elongated hole 111 and radial hole 112 in the shaft portion 105 of the insertion portion 102. In this state, the male thread portion 107 of the shaft portion 105 is engaged in the threaded hole 106 in the handle portion 103. Thereby, the straight portion 108a of the thread guide member 108 is contained in the fixed pipe 104 and the thread guide member 108 is fixed to the insertion portion 102. The sixth embodiment is identical to the first embodiment with respect to the other structural features.

Figure 26:
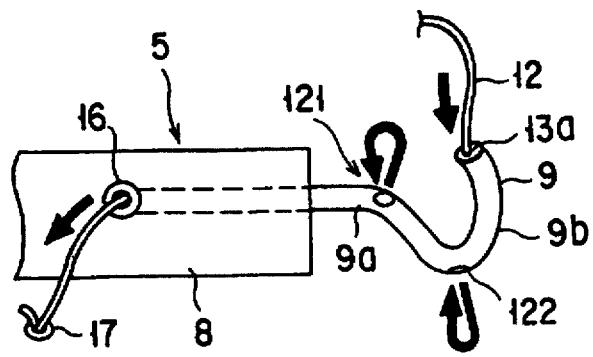
FIG. 26 is a perspective view showing the structure of a main part of a seventh embodiment of the invention.

FIG. 26 shows a seventh embodiment of the invention. In a thread holder 1 of a ligating apparatus according to this embodiment, thread insertion holes 121 and 122 are formed in an arcuated portion 9b of a thread guide member 9 at a beginning portion of the arc and an almost middle portion of the arc. The thread guide member 9 is irremovably fixed to a distal end member body 8 of a distal end member 5. The seventh embodiment is identical to the first embodiment with respect to the other structural features.

In this structure, the suture thread 12 is passed through the thread guide member 9 in the following manner. The suture thread 12 is inserted into the thread guide member 9 from a thread release port 13a and a free end portion of the suture thread 12 is once pulled out of the thread guide member 9 from the thread insertion hole 122 in the arcuated portion 9b. Then, the free end portion of the suture thread 12 is inserted once again into the arcuated portion 9b from the same thread insertion port 122. Further, the free end portion of the suture thread 12 is pulled out of the arcuated portion 9b from the other thread insertion port 121 and is inserted once again into the arcuated portion 9b from the thread insertion port 121.

Since a plurality of thread insertion holes 121 and 122 are formed in the arcuated portion 9b of the thread guide member 9, the suture thread 12 can be easily inserted into a curved or bent suture thread passage 13.

Figure 27:
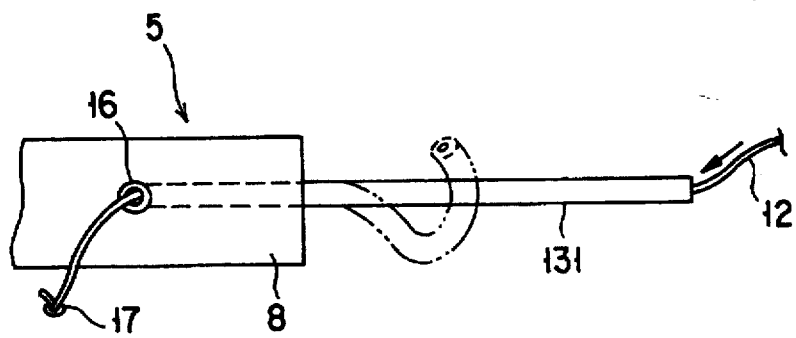
FIG. 27 is a perspective view showing the structure of a main part of an eighth embodiment of the invention.
Figure 28:
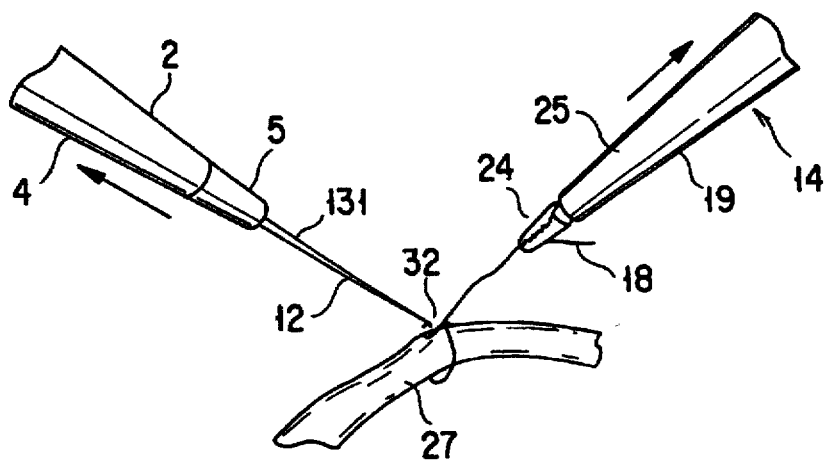
FIG. 28 is a perspective view showing a main part of the ligating apparatus shown in FIG. 27, which is being used.

FIGS. 27 and 28 show an eighth embodiment of the invention. In a ligating apparatus according to this embodiment, the thread guide member 9 of the first embodiment is replaced with a soft resilient tube having an original bent shape. Specifically, as shown in FIG. 27, a thread guide member 131 of this embodiment is formed of a soft resilient tube which can be straightened. A proximal end portion of the thread guide member 131 is irremovably fixed to a distal end member body 8. The eighth embodiment is identical to the first embodiment with respect to the other structural features.

According to the above structure, since the thread guide member 131 is resilient, the suture thread 12 can be inserted into the thread guide member 131 in the state in which the arcuated portion 9b of the thread guide member 131 is being straightened, as shown in FIG. 27. Thus, the suture thread 12 can be easily passed through a curved or bent suture thread passage 13. Furthermore, when the tubular tissue 27 such as a blood vessel is ligated by the suture thread 12, the thread holder 1 is pulled and the arcuated portion 9b of the thread guide member 131 can be straightened. Accordingly, a knot formed by passing the free end portion 18 of the suture thread 12 through the quasi-loop 28 can be tightened without rotating the thread holder 1. At the same time, the knot can be easily fallen from the arcuated portion 9b of the thread guide member 131.

Figure 29:
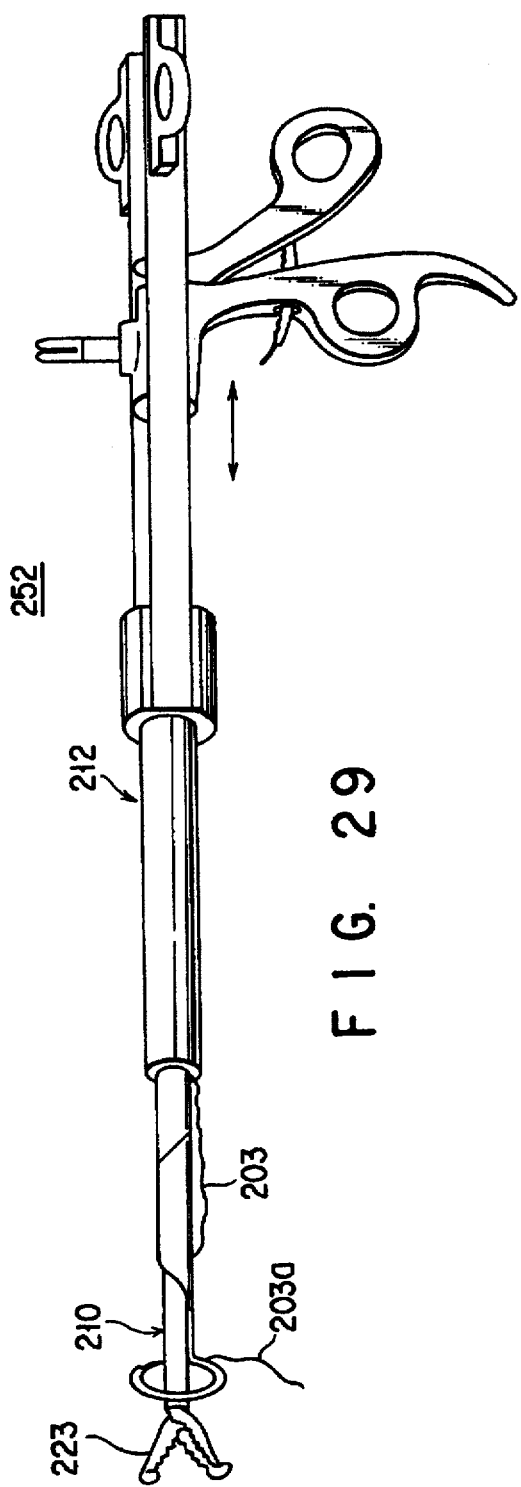
FIG. 29 shows the entire structure of a ligating apparatus according to a ninth embodiment of the invention.

FIGS. 29 to 56 show a ninth embodiment of, the invention. As is shown in. FIG. 29, a ligating apparatus 252 of this embodiment comprises a tubular thread hooking device (first ligating member) 212 in which a suture thread (or a ligation thread) 203 is set, and a forceps (second ligating member) 210 movably inserted into the thread hooking device 212 and having at a distal end a holding member 223 for holding the suture thread 203.

Figure 30:
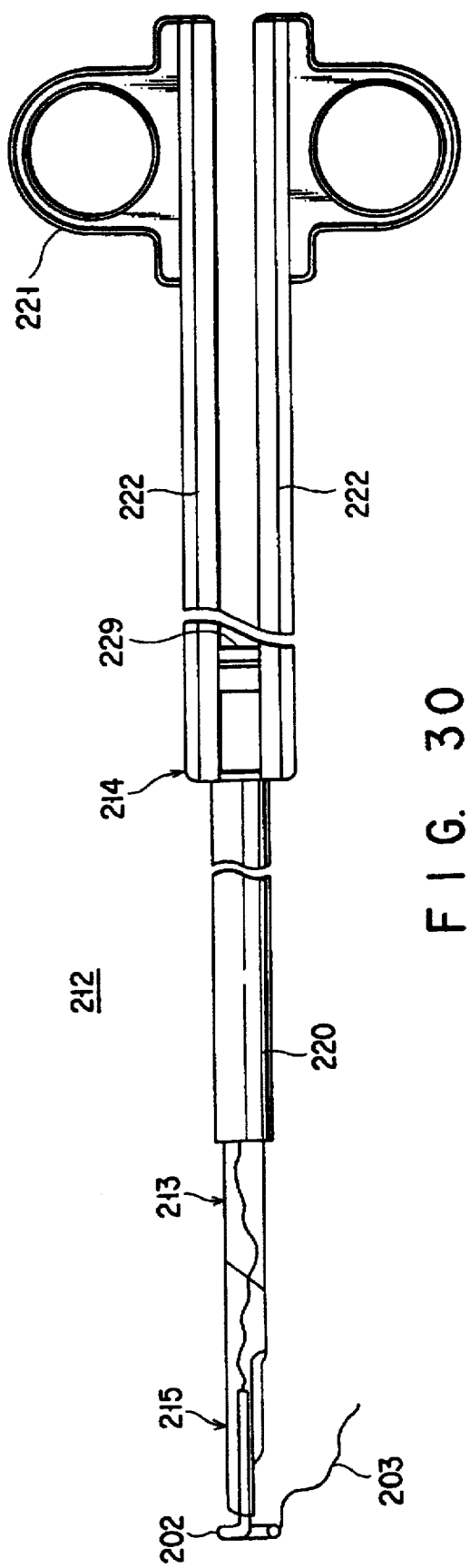
FIG. 30 shows the entire structure of a thread hooking device of the ligating apparatus shown in FIG. 29.

As is shown in FIGS. 30 and 31, the thread hooking device 212 comprises an outer pipe 214 having a handle portion 221 on a proximal side thereof; an inner pipe 213 having a proximal end portion removably inserted into the outer pipe 214 and being rotatable relative to the outer pipe 214; and a distal end member body 215 detachably mounted on a distal end portion of the inner pipe 213. When the distal end member body 215 is attached to the inner pipe 213, the distal end member body 215 is unrotatably fixed to the inner pipe 213. In other words, the distal end member body 215 in the attached state rotates as one body with the inner pipe 213.

As is shown in FIG. 31, the distal end member body 215 comprises a tubular knot forming member 201 having at a distal end portion an arcuated portion 202 forming an arcuated loop, and a support member 216 supporting at a distal end portion the knot forming member 201. One end portion of the suture thread 203 is passed through the knot forming member 201, and a free end portion 203a of the suture thread 203 is guided out of a terminal end 236 of the arcuated portion 202 of the knot forming member 201.

The inner pipe 213 includes resilient connection pipes 217a and 217b on both sides thereof. A cam groove 219 having a predetermined path is provided on the outer peripheral surface of the inner pipe 213. The cam groove 219 comprises straight grooves 219a and a helical groove 219b formed between the straight grooves 219a. As will be described later, the helical groove 219b is provided in such a position that the inner pipe 213 (i.e. the knot forming member 201 attached to the inner pipe 213) is rotated clockwise by a ⅔ rotation, preferably one rotation, just before a holding member 223 of the forceps 210 advanced to the distal-end side passes through the arcuated portion 202 of the knot forming member 201. A distal end portion of the cam groove 219 is a closed terminal end 245a, and a proximal end portion of the cam groove 219 is an open end portion 245b. An annular thread fixing member 218 for fixing the suture thread 203 is fitted on the outer peripheral surface of the inner pipe 213 between the closed end portion 245a of the cam groove 219 and the connection pipe 217a.

The outer pipe 214 comprises an insertion portion 220 and a handle portion 221 coupled to a proximal end portion of the insertion portion 220 via two parallel members 222. A guide path 274 for guiding a proximal end portion of the forceps 210 in the longitudinal direction is formed between the two parallel members 222.

Figures 32A, 32B:
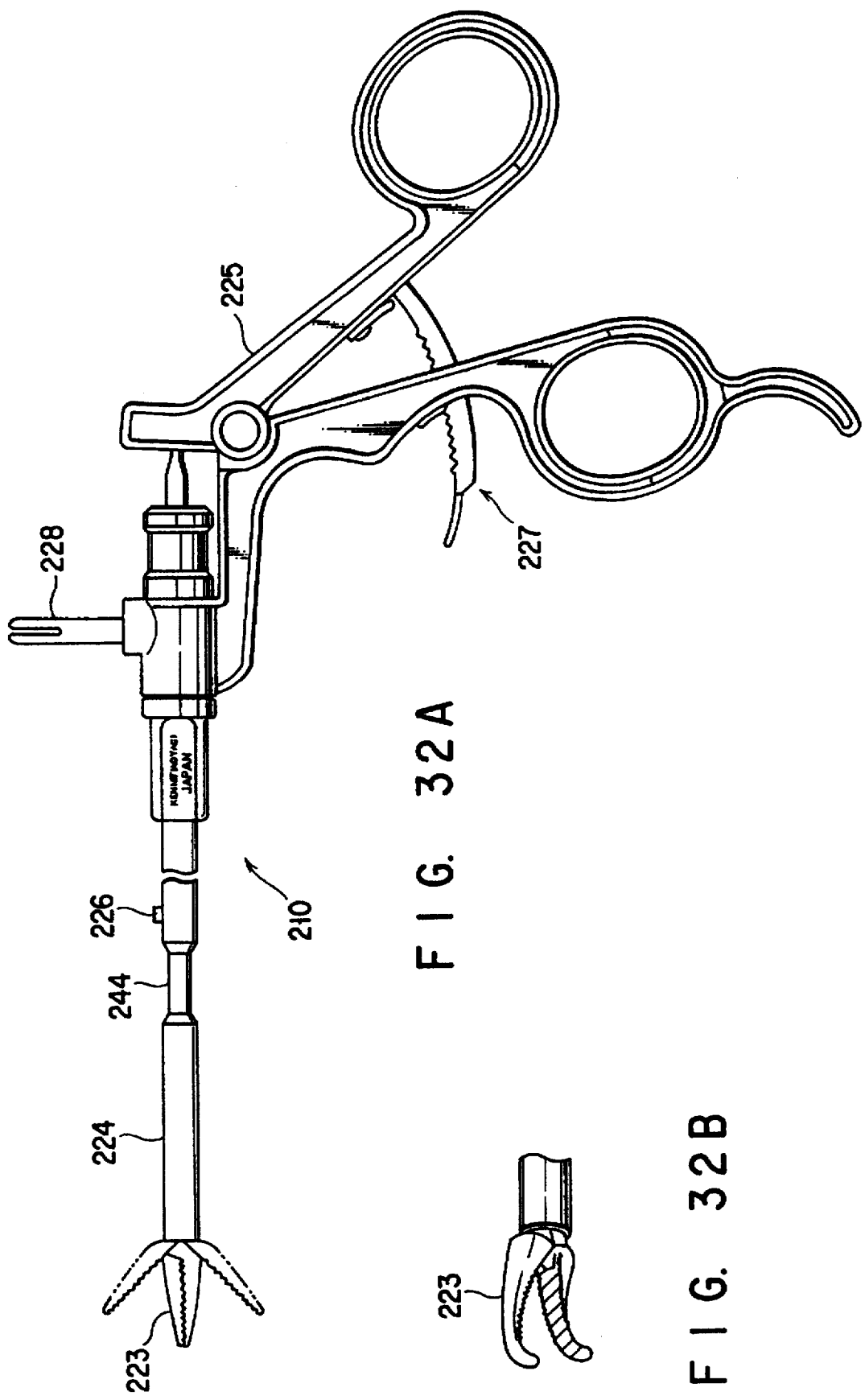
FIG. 32A shows the entire structure of the forceps of the ligating apparatus shown in FIG. 29.
FIG. 32B shows a holding portion of the forceps shown in FIG. 32A.

As is shown in FIGS. 32A and 32B, the forceps 210 is one generally used in an endoscopic surgical operation. The forceps 210 generally comprises a holding member 223 for holding the suture thread 203, an insertion portion 224, and a handle portion 225. The forceps 210 is constructed so as to permit free assembly and disassembly. In the assembled state, the insertion portion 224 and holding member 223 are not rotatable relative to the handle 225. As is shown in FIG. 32B, the holding member 223 has a tapered, leftwardly bent shape suitable for exfoliating a blood vessel, etc. As is shown in FIG. 32A, a pin 226 to be engaged with the cam groove 219 of the inner pipe 213 is projected on the outer surface of the insertion portion 224. In addition, the handle portion 225 is provided with a handle lock mechanism 227 constituted by a ratchet, and a power supply pin 228. In this structure, the holding member 223 is opened and closed by the opening/closing operation of the handle portion 225. The closed state of the holding member 223 is maintained by the ratchet 227. A high-frequency current is supplied to the holding member 223 through the power supply pin 228. The forceps 210 is electrically insulated, except for conductive parts including the power supply pin 228. A small-diameter portion 244 is provided midway on the insertion portion 224 of the forceps 210 between the pin 226 and holding member 223.

Figure 33:
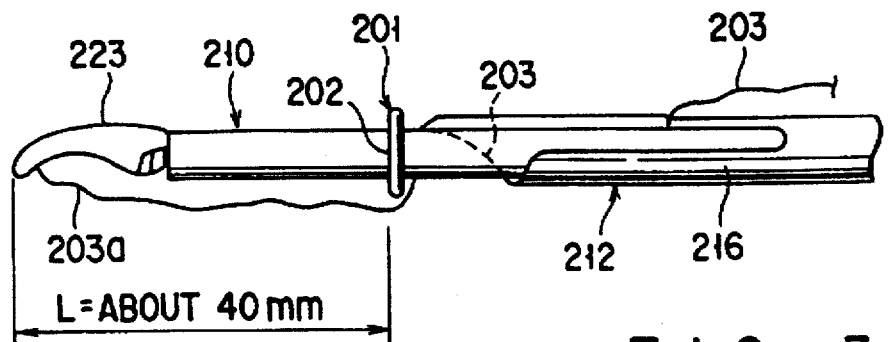
FIG. 33 shows the state in which the forceps is projected from the arcuated portion of the thread hooking device.

The forceps 210 having the above structure is inserted into the inner pipe 213 from a forceps insertion hole 229 (see FIG. 30) provided at an end portion of the outer pipe 214 of the thread hooking member 212. The forceps 210 in the inserted state can project forward by, e.g. about 40 mm from knot forming member 201, as shown in FIG. 33. The length L of this projection is determined such that the knot forming member 201 does not interfere when the forceps 210 alone is used in an exfoliating operation. In addition, the length L is approximately equal to the length of the suture thread 203.

As mentioned above, the inner pipe 213 is provided with the cam groove 219. Thus, after the pin 226 of the forceps 210 is inserted into the cam groove 219 from the open end portion 245*b* provided on the forceps insertion hole (229) side, the forceps 210 and inner pipe 213 are moved as one body because of the engagement between the pin 226 and groove 219. Specifically, while the pin 226 of the forceps 210 is engaged with the straight groove 219*a*, the forceps 210 simply moves back and forth in the inner pipe 213. When the pin 226 of the forceps 210 is engaged with the helical groove 219*b*, the inner pipe 213 is rotated in accordance with the back-and-forth movement of the forceps 210. In the present embodiment, the inner pipe 213 is provided with the cam groove 219, and the forceps 210 is provided with the pin 226. However, the same operation can be achieved even if the pin is provided on the inner surface of the inner pipe 213 and the groove is formed in the outer peripheral surface of the insertion portion 224 of the forceps 210.

The respective parts of the ligating apparatus 22 will now be described in greater detail.

Figure 34:
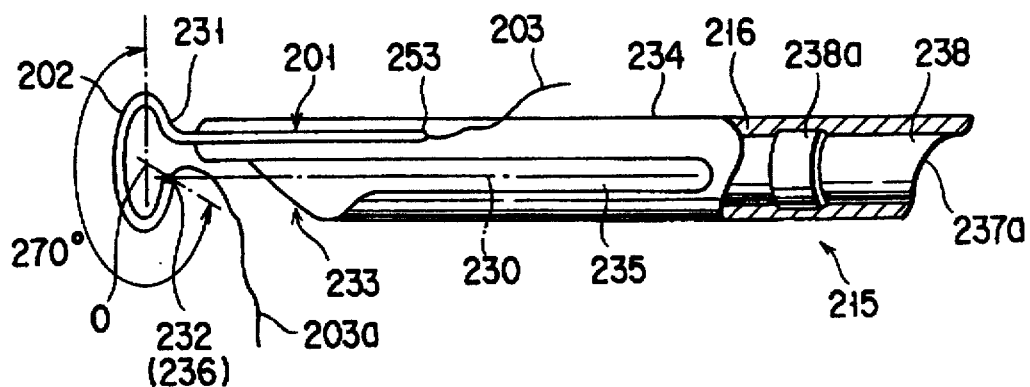
FIG. 34 shows in detail the distal end member body of the thread hooking device shown in FIG. 30.

As is shown in FIG. 34, the knot forming member 201 of the distal end member body 215 is formed of a hollow member of a hard material. The inside diameter of the knot forming member 201 is greater than the thickness of the suture thread 203 so that the suture thread 203 can be passed through the knot forming member 201. The knot forming member 201 extends in the axial direction of the support member 216 from the distal end of the support member 216 and constitutes an arcuated portion 202 extending clockwise about a center O from an arc beginning portion 231 to a thread release portion 232 on the axis of the support member 216. As is clear from FIG. 34, the thread release portion 232 coincides with the end portion 236 of the arcuated portion 202. The knot forming member 201 may be formed of a resilient soft tube having an original bent shape.

The inside diameter and central angle of the arcuated portion 202 are determined so that the forceps 210 can be passed through a quasi-loop 204 (see FIG. 37B) formed by an arc and a chord connecting the thread release portion 232 and arc beginning portion 231. For example, in this embodiment, the inside diameter of the arcuated portion 202 is slightly greater than the outside diameter of the forceps 210 and the central angle of the arcuated portion 202 is 270°. In this context, the expression "an arc and a chord connecting the thread release portion 232 and arc beginning portion 231" is used because the "loop" shape of the knot forming member 201 is not necessarily an arcuated shape and may be a polygonal shape (it should be noted, however, that the knot forming member 201 must be a single loop with a missing portion).

The suture thread 203 is guided through the knot forming member 201 from the thread release portion 232 and led to the outside from an outer peripheral surface 234 of the support member 216 through a thread exit 253. The support member 216 has a counterclockwise helical portion 233 as an end portion thereof. A longitudinally extending notched groove 235 with a central angle of about 90° and a length of 40 mm is formed in the outer peripheral surface 234 of the support member 216. The length of the notched groove 235 is substantially equal to the above-mentioned length L of the projected distal end portion of the forceps. The knot forming member 201 is provided such that the end portion 236 of the arcuated portion 202 is located on a central axis 230 of the notched groove 235. An end face 237*a* of the inner pipe 213 of the support member 216 is beveled, and an elongated hole 238 to be engaged with the connection pipe 217*a* provided at the distal end of the inner pipe 213 is formed in the end face 237*a*.

Figures 35A, 35B:
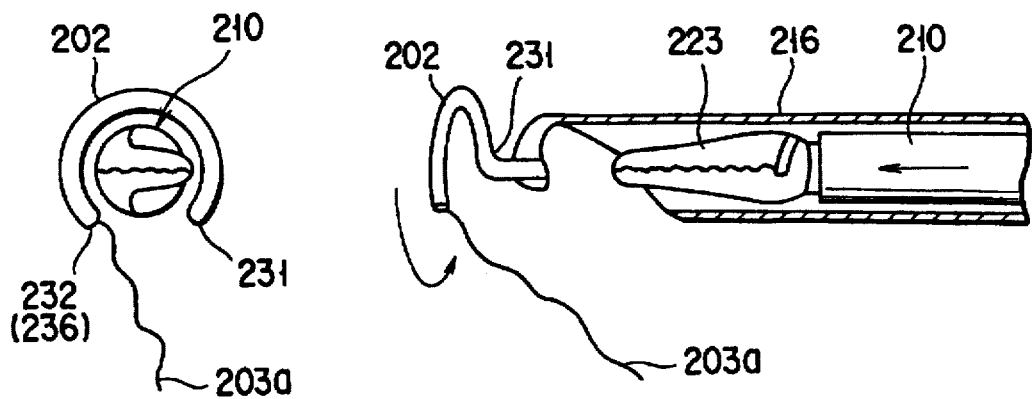
FIG. 35A is a front view showing the state in which the forceps has not yet been passed through the arcuated portion of the thread hooking device.
FIG. 35B is a cross-sectional side view showing the state in FIG. 35A.
Figure 36A:
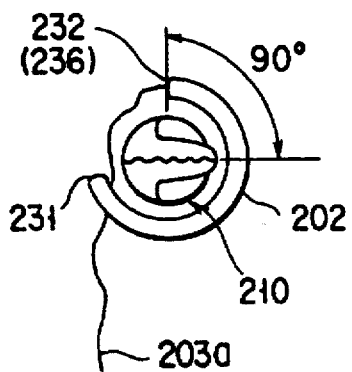
FIG. 36A is a front view showing the state in the forceps is being passed through the arcuated portion of the thread hooking device.
Figure 36B:
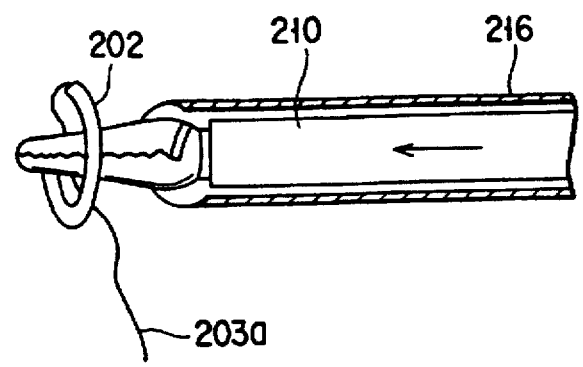
FIG. 36B is a cross-sectional side view showing the state in FIG. 36A.
Figure 37A:
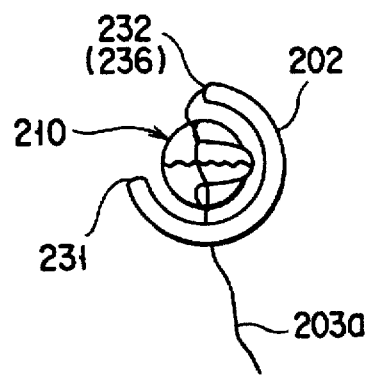
FIG. 37A is a front view showing the state in which the distal end portion of the forceps is about to be passed through the quasi-loop.
Figure 37B:
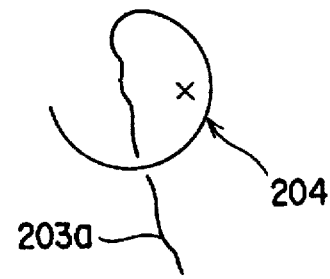
FIG. 37B shows a quasi-loop formed by the arcuated portion and the suture thread.

As is shown in FIGS. 35A and 35B and FIGS. 36A and 36B, the forceps 210 is set such that the direction of bending of the distal end portion of the holding member 223 of the forceps 210 is about 90° to the distal end (terminal end 236) of the arcuated portion 202 when the forceps 210 passes through the arcuated portion 202. Accordingly, even if the quasi-loop 204 does not have enough size, as shown in FIGS. 35A and 35B, the suture thread 203 forming the quasi-loop 204 can be pushed outward by the distal end (indicated by "X" mark in FIG. 37B) of the holding member 223. Therefore, the distal end of the forceps 210 can be exactly passed through the quasi-loop 204. Specifically, in this structure, the knot forming member 201 is rotated in accordance with the back-and-forth movement of the forceps 210. In this case, when the holding member 223 of the forceps 210 is passed through the arcuated portion 202, the knot forming member 201 is rotated such that the quasi-loop 204 is formed of the arcuated portion 202 and ligation thread 203 and such that the holding member 223 can pass through the formed quasi-loop 204. In addition, in order to achieve this operation, the shape of the knot forming member 201 and the shape of the cam groove 219 of the inner pipe 213 are determined.

Figure 38:
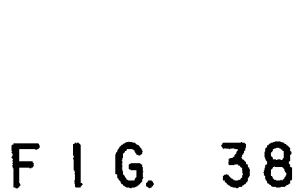
FIG. 38 is an enlarged view of a distal end portion of an inner pipe of the thread hooking device shown in FIG. 30.
Figure 39:
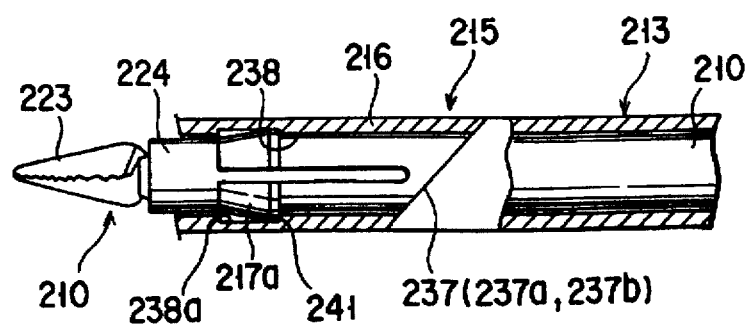
FIG. 39 is a distal-end side cross-sectional view in the state in which the distal end member body is connected to the inner pipe.

As is shown in FIG. 38, the end face 237*b* of the inner pipe 213 is beveled in a direction opposite to the bevel direction of the end face 237*b* of the support member 216. The resilient connection pipe 217*a* with radially extending four slits 239*a* is axially projected from the end face 237*b*. The inside diameter of the connection pipe 217*a* is substantially equal to the outside diameter of the insertion portion 224 of the forceps 210. The connection pipe 217*a* has a large-diameter distal end portion with a length of several mm. A stepped portion 241 is provided on the outer surface of this large-diameter distal end portion. The inner pipe 213 and distal end member body 215 are coaxially arranged by inserting the connection pipe 217*a* into the elongated hole 238 in the support member 216 while the connection pipe 217*a* is bent radially inward (in the direction of the arrow in FIG. 38). If the connection pipe 217*a* restores to its original shape and the distal end portion of the connection pipe 217*a* is engaged with a large-diameter engagement groove 238a (see FIG. 34) in the elongated hole 238, the stepped portion 241 of the connection pipe 217a functions as a removable prevention means and the inner pipe 213 and distal end member body 215 are axially fixed. Furthermore, in this fixed state, the beveled faces 237a and 237b of the support member 216 and inner pipe 213 abut upon each other without gap and therefore the rotation of the distal end member body 215 relative to the inner pipe 213 is also prevented. When the forceps 210 is inserted into the inner pipe 213 and reaches the connection pipe 217a, the forceps 210 cannot deform the connection pipe 217a because the outside diameter of the insertion portion 224 of the forceps 210 is substantially equal to the inside diameter of the connection pipe 217a. Therefore, the distal end member body 215 is not removed from the inner pipe 213.

Figure 40:
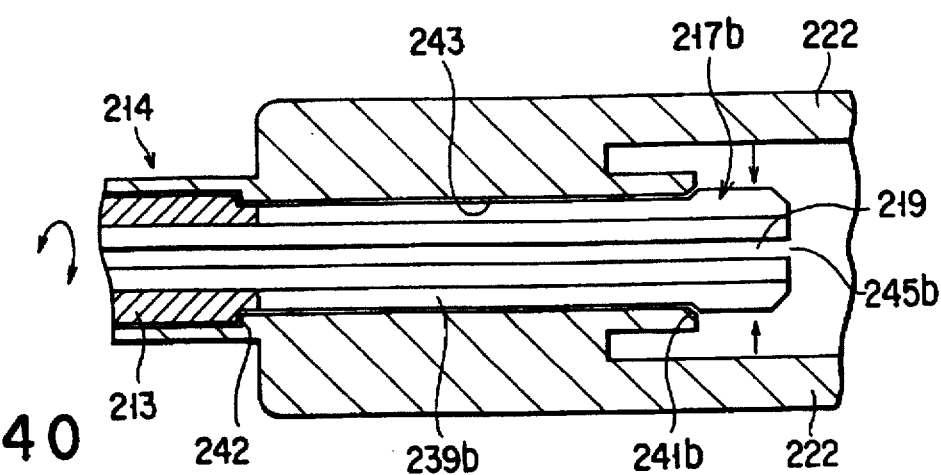
FIG. 40 is a proximal-end side cross-sectional view in the state in which outer and inner pipes are connected.

As is shown in FIG. 40, an elongated groove 239b is formed in the connection pipe 217b provided at a handle (221)-side end portion of the inner pipe 213. The outside diameter of the connection pipe 217b is less than that of the inner pipe 213. The connection pipe 217b has a step-like abutment portion 242. Like the connection pipe 217a on the distal end member body (215) side, a stepped portion 241b is formed at a distal end portion of the connection pipe 217b. In this structure, when the inner pipe 213 is inserted into the outer pipe 214 and the connection pipe 217b is engaged in a fixing hole 243 in the outer pipe 214, the inner pipe 213 is axially fixed by the abutment portion 242 of the connection pipe 217b and stepped portion 241b. However, the rotation of the inner pipe 213 is permitted by the engagement between the pin 226 on the forceps 210 and the cam groove 219 in the inner pipe 213. In this case, the forceps 210 inserted into the inner pipe 213 prevents the inner pipe 213 from being removed from the outer pipe 214, like the fixation of the connection pipe 217a.

The annular thread fixing member 218 (see FIG. 31) fitted on the outer periphery of the inner pipe 213 will now be described in detail with reference to FIGS. 41 and 42.

Figure 41:
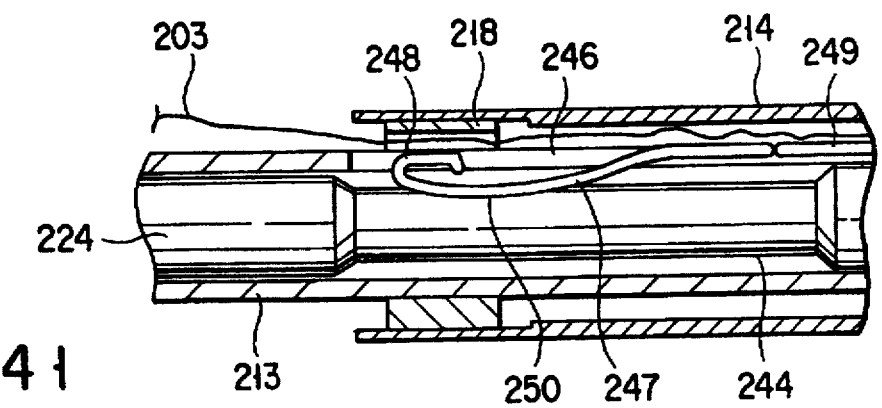
FIG. 41 is a cross-sectional view of a thread fixing portion in a thread fixing release state of the thread hooking device shown in FIG. 30.
Figure 42:
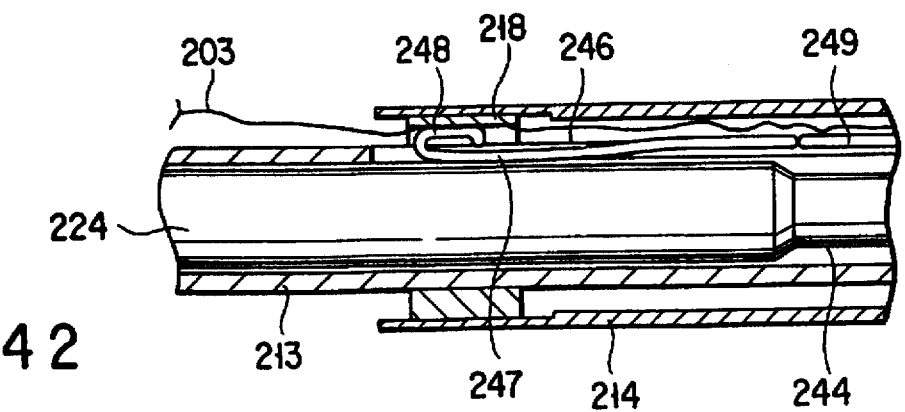
FIG. 42 is a cross-sectional view of a thread fixing portion in a thread fixing state of the thread hooking device shown in FIG. 30.

As is shown in FIGS. 41 and 42, the thread fixing member 218 cooperates with the plate spring 247 to fix the suture thread 203. Specifically, an axial slit 246 is formed in the outer peripheral surface of the inner pipe 213. A plate spring 247 having a width slightly less than the width of the slit 246 is fixed along the slit 246. A proximal end portion of the plate spring 247 is fixed to a spring fixing portion 249, and a distal end portion thereof is bent to form a flat portion 248 extending substantially along the axis of the inner pipe 213.

That portion of the plate spring 247, which is located between the flat portion 248 and spring fixing portion 249, has a resilient curved shape projecting radially inward of the inner pipe 213. In the natural state, a top point 250 of this curved portion projects radially inward of the inner pipe 213. In addition, the annular thread fixing member 218 fitted on the outer periphery of the inner pipe 213 is located outside the flat portion 248 of the plate spring 247. In this structure, if the plate spring 247 is forcibly pushed radially outward of the inner pipe 213, the suture thread 203 located between the flat portion 248 and a thread fixing member 218 is clamped and fixed therebetween. The pushing of the plate spring 247 is effected by the insertion portion 224 of the forceps 210. Specifically, when the forceps 210 is passed through the inner pipe 213, the outer surface of the insertion portion 224 of the forceps 210 pushes up the plate spring 247 and the suture thread 203 is clamped and fixed between the flat portion 248 and ring-shaped portion 251 (see FIG. 42). However, the plate spring 247 falls into the small-diameter portion 244 of the forceps 210 when the length of projection of the forceps 210 from the knot forming member 201 reaches a maximum value (i.e. the maximum projection value L determined in terms of mechanical structure). Thus, in the state shown in FIG. 41, the fixation of the suture thread 203 is released and the suture thread 203 can be freely pulled out.

The outside diameter of the thread fixing member 218 is slightly less than the inside diameter of the outer pipe 214. Thus, the thread fixing member 218 can serve as guide means for smooth rotation of the inner pipe 213 and outer pipe 214 when the inner pipe 213 and outer pipe 214 are assembled.

A method of using the ligating apparatus 252 will now be described.

At first, the concept of the method of forming a knot with use of the ligating apparatus 252 of this embodiment will now be described with reference to FIGS. 43A to 46B.

Figure 43A:
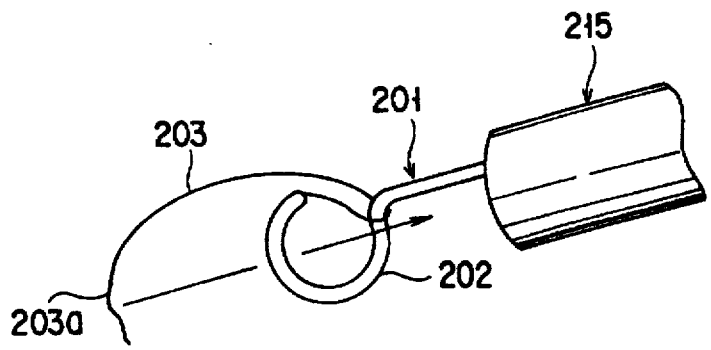
FIG. 43A and FIG. 43B show a first step of forming a first half-knot.
Figure 43B:
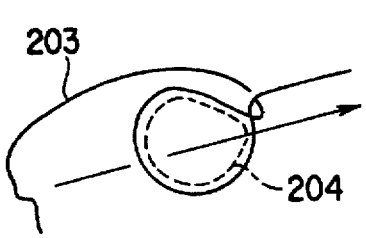
Figure 44A:
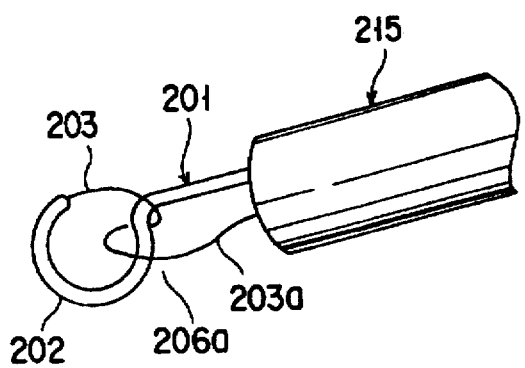
FIG. 44A and FIG. 44B show a second step of forming the first half-knot.
Figure 44B:
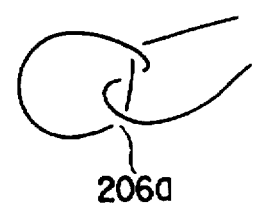
Figure 45A:
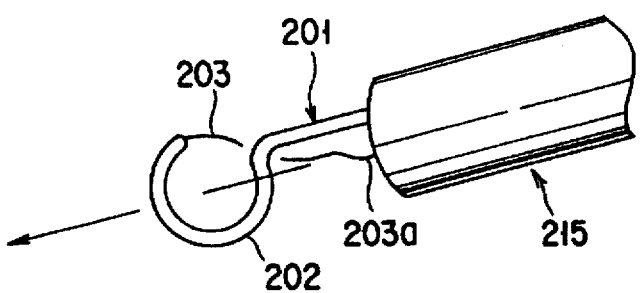
FIG. 45A and FIG. 45B show a first step of forming a second half-knot.
Figure 45B:
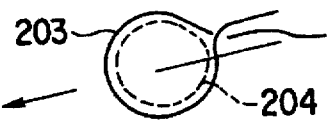
Figure 46A:
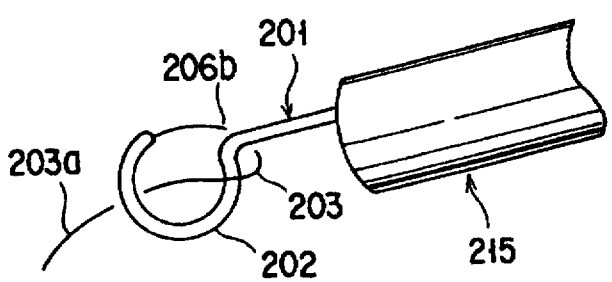
FIG. 46A and FIG. 46B show a second step of forming the second half-knot.
Figure 46B:

As is shown in FIGS. 43A and 43B, one quasi-loop 204 is formed by the arcuated portion 202 of the knot forming member 201 and the suture thread 203 extended in an arc. In this case, the suture thread 203 is looped on the front side of the knot forming member 201. From this state, the free end portion 203a of the suture thread 203 is passed through the quasi-loop 204 from the rear side towards the front side. Thus, a first half-knot 206a is provisionally formed, as shown in FIGS. 44A and 44B. The provisional first half-knot 206a is fallen from the knot forming member 201 and is tightened. Thus, the first half-knot 29 is formed, as shown in FIG. 16B.

Then, a second half-knot is formed in a direction reverse to that of the first half-knot 29. Thus, the secure square knot 32 (see FIG. 16B) is formed. In order to form the square knot 32, the free end portion 203a of the suture thread 203 must be passed through the quasi-loop 204 in the reverse direction, as shown in FIGS. 45A to 46B. Specifically, the suture thread 203 is looped on the rear side of the knot forming member 201 and the free end portion 203a of the suture thread 203 is passed, from the front side towards the rear side, through the quasi-loop 204 formed by the arcuated portion 202 and suture thread 203 extended in an arc. Thus, a provisional half-knot 206b is formed and the second half-knot 31b is formed (see FIG. 16B).

Through the above procedure, the square knot 32 is formed. The insertion of the suture thread 203 through the quasi-loop 204 is effected by the forceps 210 which can move back and forth through the inner pipe 213 and distal end member body 215. The knot forming member 201 fixed to the distal end member body 215 is rotated relative to the forceps 210. Thereby, the quasi-loop 204 is easily formed and the provisional half-knot (206a, 206b) is fallen from the knot forming member 201.

The actual ligation of a blood vessel with use of the ligating apparatus 252 of this embodiment will now be described with reference to FIGS. 47 to 56.

Before using the ligating apparatus 252, the distal end member body 215 in which the suture thread 203 is set is prepared. A new distal end member body 215 is attached to the inner pipe 213 for every use. Of course, the suture thread 203 alone may be set to the distal end member body 215 for every use.

The length of the suture thread 203 is set at about 20 cm to 80 cm in order to perform ligation at several locations. The suture thread 253 on the thread exit (253) side of the knot forming member 201 is passed between the thread fixing member 218 and the flat portion 248 of the plate spring 247 and wound around the inner pipe 213. In this state, the suture thread 203 is inserted into the outer pipe 214. Since the suture thread 203 is contained between the inner pipe 213 and outer pipe 214, the suture thread 203 is not influenced even when the ligating apparatus 252 is moved or rotated. In this state, the forceps 210 is inserted into the inner pipe 213 from the forceps insertion hole 229 and the suture thread 203 is fixed, as mentioned above. Thus, the preparation for the use of the ligating apparatus 252 is completed.

Figure 47:
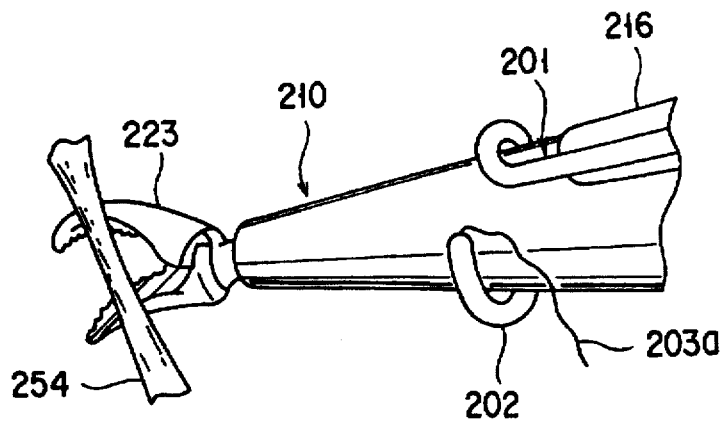
FIG. 47 shows the state in which a tubular tissue is exfoliated by a forceps.
Figure 48:
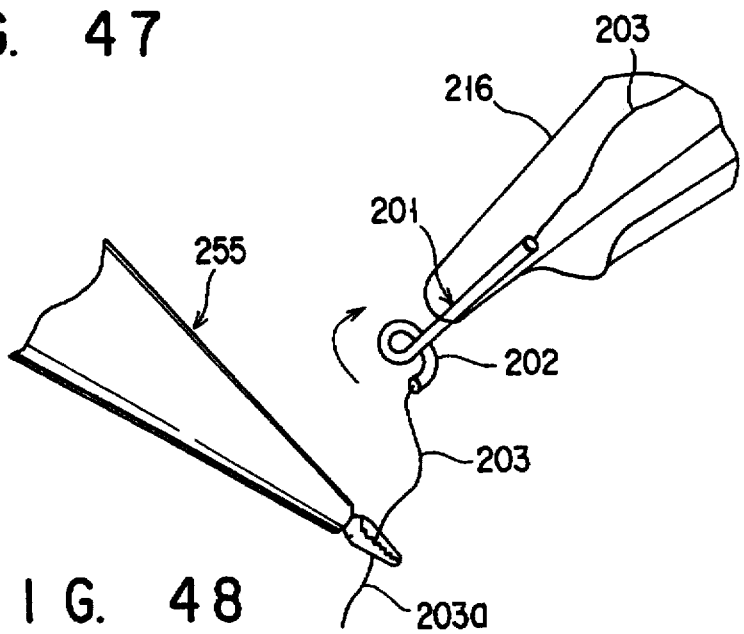
FIG. 48 shows the state in which the free-end portion of the ligation thread is held by another forceps.
Figure 49:
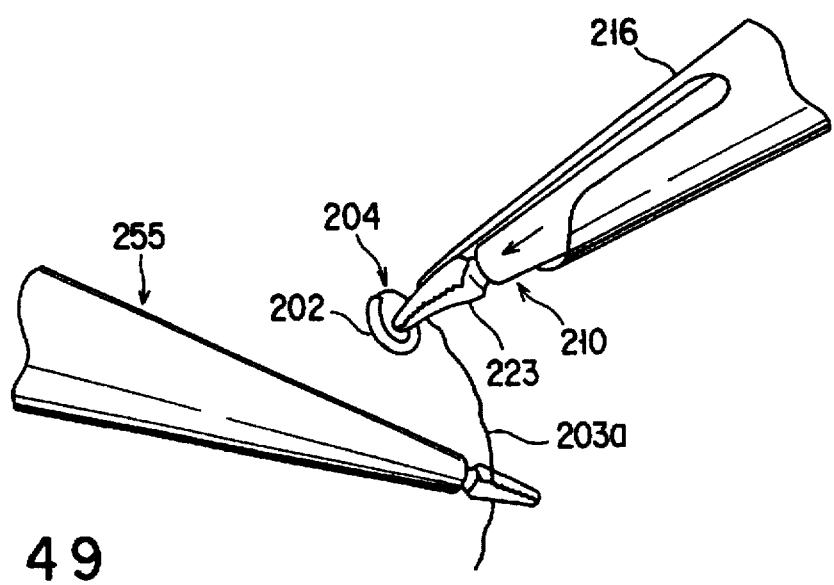
FIG. 49 shows the state in which a quasi-loop is formed, following the state shown in FIG. 48.
Figure 50:
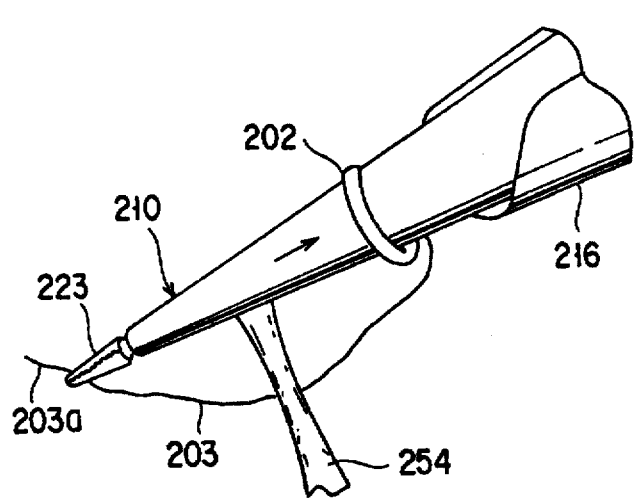
FIG. 50 shows the state in which the ligation thread is passed through the tissue and the free-end portion of the ligation thread is held by the forceps.
Figure 51:
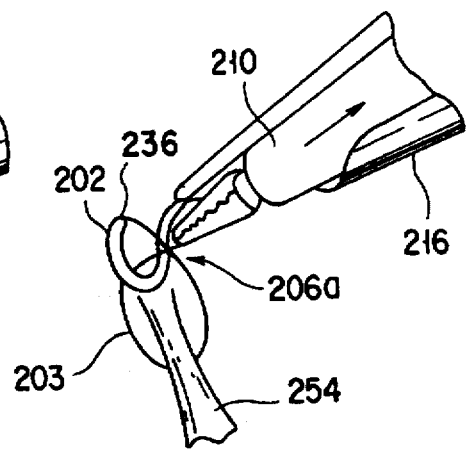
FIG. 51 shows the state in which the free end portion of the ligation thread held by the forceps is passed through the quasi-loop, thereby to form a first half-knot of a knot.
Figure 52:
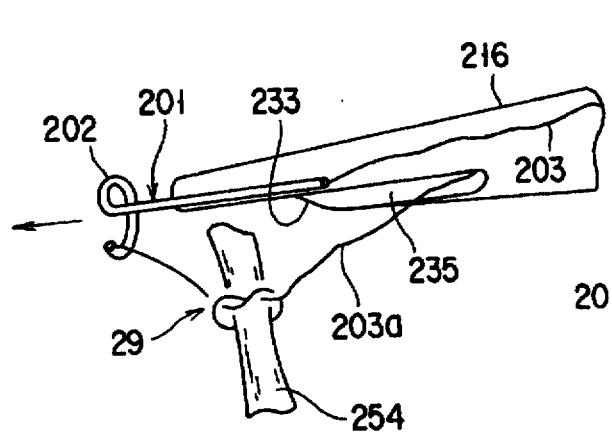
FIG. 52 shows the state in which the first half-knot is fallen from a knot forming member and the formation of the first half-knot is completed.

As is shown in FIG. 47, a tubular tissue 254 such as a blood vessel is exfoliated and exposed by means of the forceps 210. At this time, a high-frequency current is supplied to the forceps 210 on an as-needed basis. The forceps 210 is once pulled to the front side of the knot forming member 201, and the free end portion 203a of the suture thread 203 is held by another forceps 255 (see FIG. 48). The forceps 210 is advanced once again, thereby rotating the knot forming member 201 and forming the quasi-loop 204 (see FIG. 49). At this time, the suture thread 203 is brought to the front side of the knot forming member 201. The forceps 210 is further advanced and, in this state, the free end portion 203a of the suture thread 203 is held by the holding member 223 of the forceps 210. If the suture thread 203 is short, the suture thread 203 is pulled out by the other forceps 255 to a desired length (this operation may be performed before the ligating apparatus 252 is inserted into the body).

Subsequently, the suture thread 203 is passed behind the tissue 254 and the free end portion 203a of the suture thread 203 is held by the forceps 210 once again. This holding state is maintained by means of the ratchet 227 and the forceps 210 is pulled into the inner pipe 213 (see FIG. 50). At this time, the half-knot 206a is provisionally formed on the arcuated portion 202. Since the knot forming member 201 is rotated, the provisional half-knot 206a can be fallen from the knot forming member 201 through the space at the terminal end 236 of the arcuated portion 202 (see FIG. 51). One end portion of the suture thread 203 is guided to the helical end face 233 of the support member 216 and led to the notched groove 235. Since the suture thread 203 is fixed by the thread fixing member 218, the provisional half-knot 206a is tightened by pulling the thread 203 and the first half-knot 29 is formed (see FIG. 52).

Figure 53:
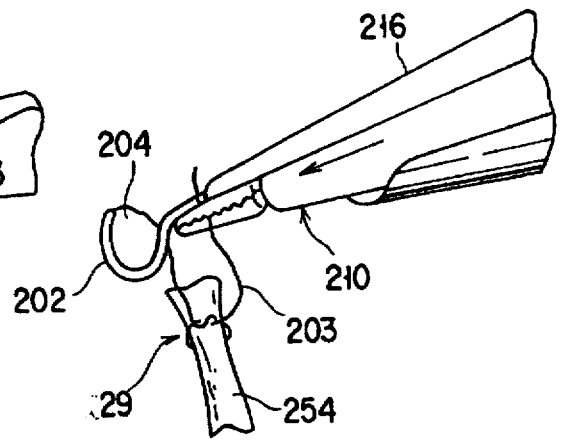
FIG. 53 shows the state in which the free-end portion of the ligation thread, while being held by the forceps, is passed through the quasi-loop, following the state shown in FIG. 52.
Figure 54:
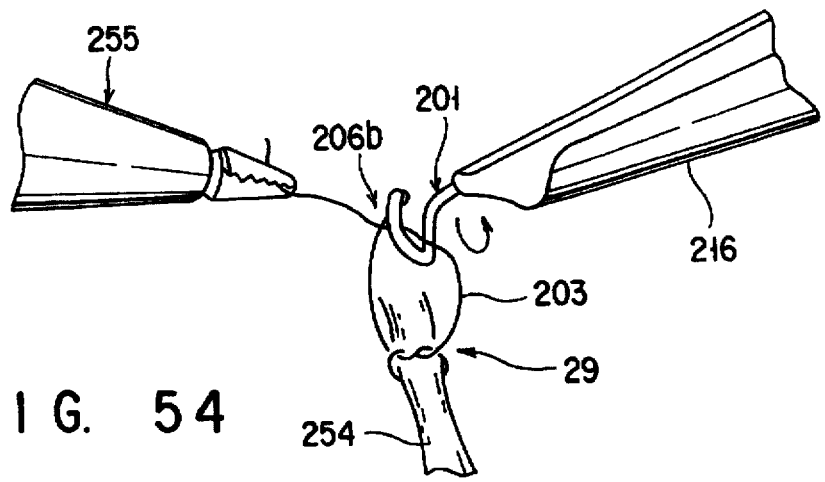
FIG. 54 shows the state in which a second half-knot is formed.
Figure 55:
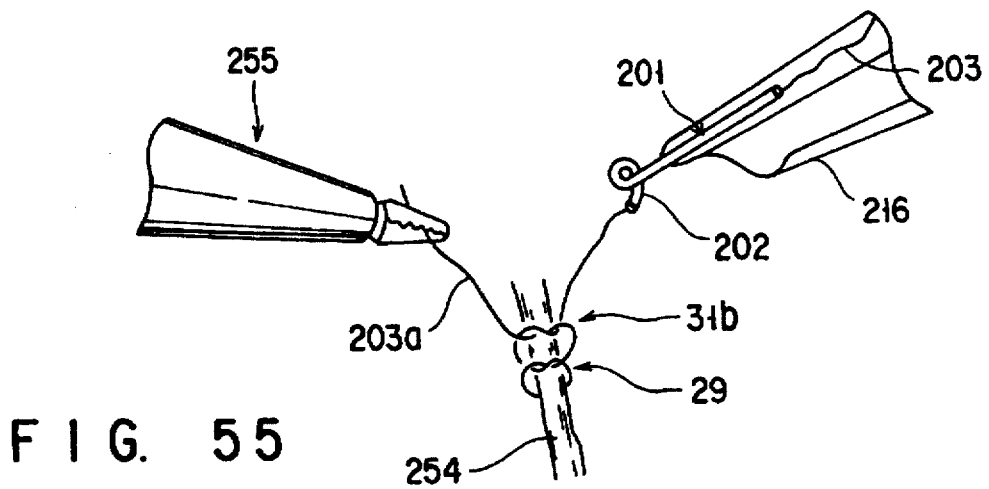
FIG. 55 shows the state in which the second half-knot is fallen from the knot forming member and the formation of the second half-knot is completed.
Figure 56:
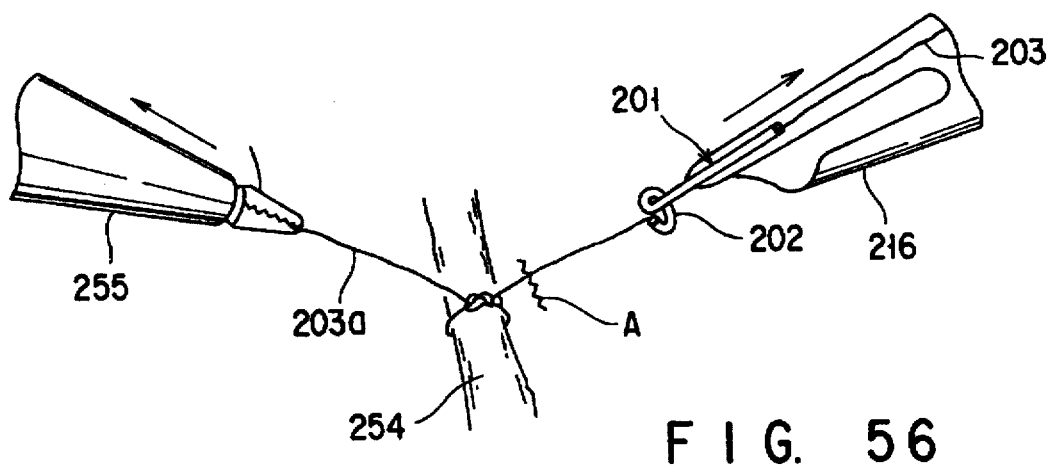
FIG. 56 shows the state in which the first half-knot and second half-knot are tightened to form a square knot.

The forceps 210 is advanced once again from the above state, and the forceps 210 holding the suture thread 203 is passed through the quasi-loop 204b from the front side of the quasi-loop 204b (see FIG. 53). (At this time, attention should be paid so that the suture thread 203 forming the quasi-loop 204b located behind the knot forming member 201). Then, the suture thread 203 is passed over to the other forceps 255 (see FIG. 54). Then, the forceps 210 is pulled to rotate the knot forming member 201 and fall the provisional half-knot 206b (see FIG. 55). The second half-knot 31b is tightened by the other forceps 255 and ligating apparatus 252 (see FIG. 56). Thus, the square knot 32 is formed. If necessary, the above procedure is repeated to form a third partial knot, a fourth partial knot, etc.

After the ligation at one location is completed, if the suture thread 203 is cut except for the portion used for the ligation (portion A in FIG. 56), the ligating apparatus 252 is restored to the initial state. Thus, the ligation can be repeated with the ligating apparatus 252 left in the body.

As has been described above, according to the ligating apparatus 252 of the present embodiment, the square knot 32 which is not easily loosened can be obtained by a simple work. In addition, since the ligating apparatus 252 has the thread holding means, both the exfoliation work and ligation work can be performed by the single ligating apparatus 252.

Furthermore, since the knot forming member 201 has a partially missing loop shape (i.e. an arcuated shape), the provisional knot 206 formed on the arcuated portion 202 can be easily fallen from the missing portion of the loop. Therefore, the ligating work can be performed efficiently.

Figure 57:
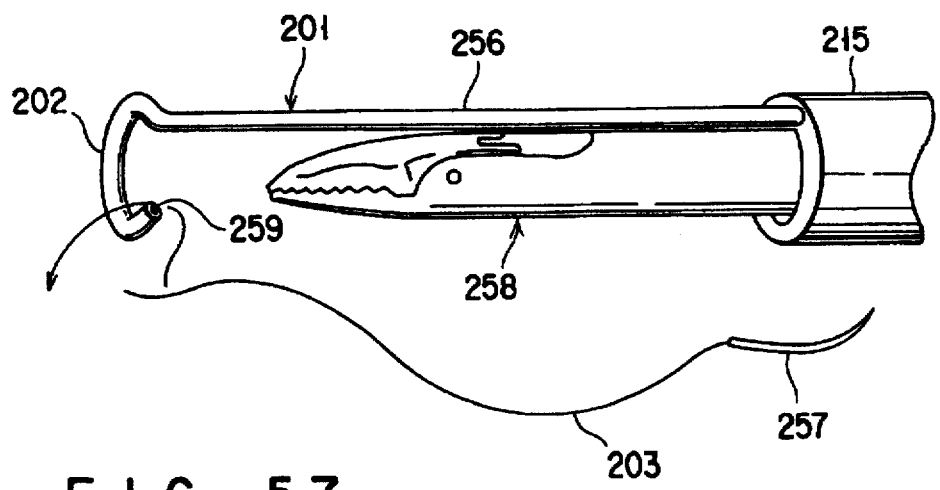
FIG. 57 shows a distal end portion of a ligating apparatus according to a tenth embodiment of the present invention.

FIG. 57 shows a tenth embodiment of the invention which is the same as the ninth embodiment, except for the points described below.

The knot forming member 201 of this embodiment is formed of a solid rod-like member comprising an arcuated portion 202 and a straight portion 256. A hole 259 for passing the suture thread 203 is formed in the terminal end portion of the arcuated portion 202 of the knot forming member 201. The suture thread 203 is passed through the hole 259 and is bound. A distal end portion of the suture thread 203 is provided with a suture needle 257. The length of the suture thread 203 is substantially equal to that of the straight portion 256 of the knot forming member 201 and is sufficient for performing the ligation according to the procedure in the ninth embodiment. The end portion of the distal end member body 215 is not provided with the notched groove 235 or helical end face 233, unlike the ninth embodiment. A needle holder 258 serving as forceps is axially movably inserted into the inner pipe 213. Thus, a ligating operation, too, can be performed.

When the apparatus of this embodiment is used, the distal end member body 215 with a needle and a thread may be prepared in advance and replaced each time the needle has been used. Alternatively, the suture thread 203 may be bound to the thread insertion hole 259 each time the needle is used. The material of the knot forming member 201 may be a superelastic alloy or a shape memory alloy.

According to the above structure, the same operation and advantage as in the ninth embodiment can be achieved, and the ligating work, too, can be performed.

Figure 58A:
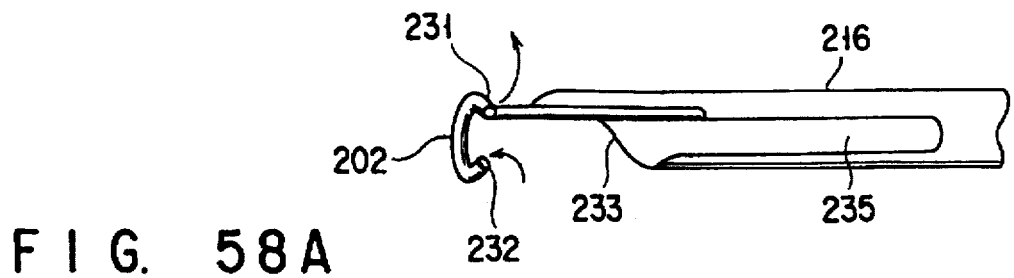
FIG. 58A and FIG. 58B show a distal end portion of a ligating apparatus according to an eleventh embodiment of the invention.
Figure 58B:
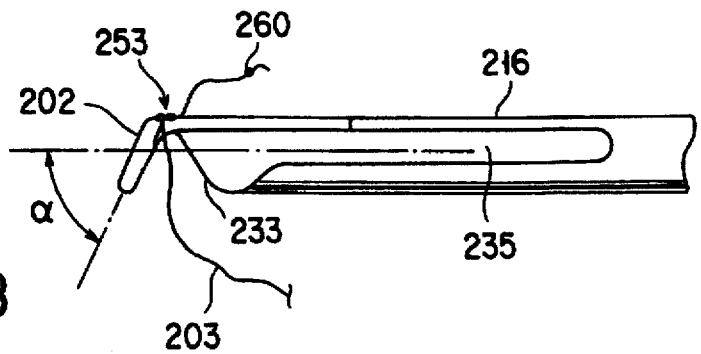

FIGS. 58A and 58B show an eleventh embodiment of the invention which is the same as the ninth embodiment, except for the points described below.

In the knot forming member 201 of this embodiment, a plane including an arcuated portion 202 is located at an angle α to the axis of the support member 216. The arcuated portion 202 is situated such that a central portion thereof is located at a forwardest position. The angle α is set at such a degree that the positional relationship between the suture thread 203 and knot forming member 201 can be exactly and easily determined when the quasi-loop 204a, 204b is formed. The general range of angle α is 60°<α<120°.

The thread exit 253 is provided near the arc beginning portion 231. The suture thread 203 is set to the knot forming member 201 such that the suture thread 203 is inserted into the arcuated portion 202 from the thread release portion 232 and pulled out of the thread exit 253, and then a knot 260 greater in size than the thread exit 253 is formed on the pulled-out suture thread 203. Thereby, the suture thread 203 cannot be removed from the knot forming member 201.

According to the above structure, the same operation and advantage as in the ninth embodiment can be obtained and a desirable relationship between the suture thread 203 and knot forming member 201 can be easily determined on forming knot.

Figure 59:
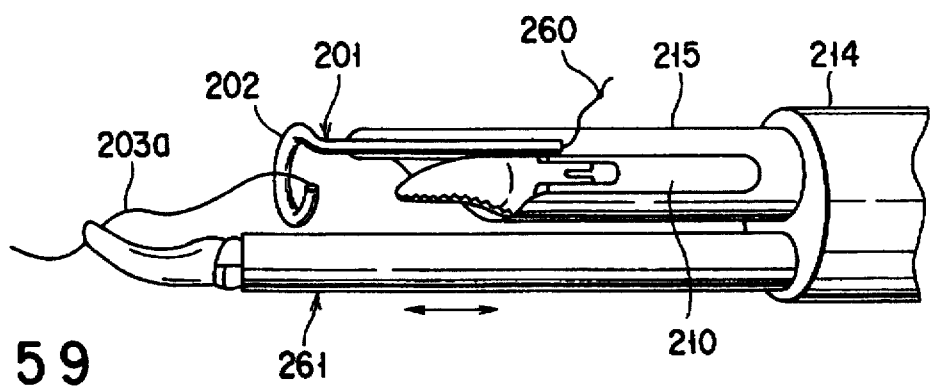
FIG. 59 shows a distal end portion of a ligating apparatus according to a twelfth embodiment of the present invention.
Figure 60:
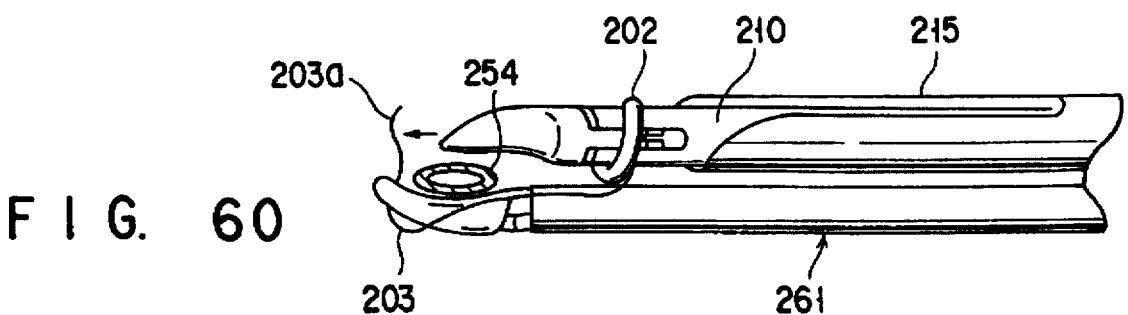
FIG. 60 shows the state in which the ligation thread is passed behind the tubular tissue by using the ligating apparatus shown in FIG. 59.

FIGS. 59 and 60 show a twelfth embodiment of the invention which is the same as the ninth embodiment, except for the points described below.

In the present embodiment, a second forceps 261 is axially movably passed within the outer pipe 214 in parallel to a first forceps 210. As is shown in FIGS. 59 and 60, the second forceps 261 extends outside the arcuated portion 202 of the knot forming member 201. A holding member of the second forceps 261 is bent towards the first forceps 210 so that the suture thread 203 can be passed between the first and second forceps 210 and 261.

FIG. 60 shows the state in which the suture thread 203 is passed over the tubular tissue 254. As is shown in FIG. 60, the terminal end portion 203a of the suture thread 203 is held by the second forceps 261 with the quasi-loop 204 being formed, and the terminal end portion 203a is passed behind the tubular tissue 254. Then, the first forceps 210 is advanced and the free end portion 203a of the suture thread 203 is received by the first forceps 210.

The subsequent procedure is the same as in the ninth embodiment. Specifically, after the provisional half-knot 206b is formed, the free end portion 203a of the suture thread 203 is passed over to the second forceps 261 and the second half-knot 31b is tightened. Thus, the square knot 32 is formed.

According to the above structure, the same operation and advantage as in the ninth embodiment can be achieved, and the ligation can be performed without the aid by the other forceps 255.

Figure 61:
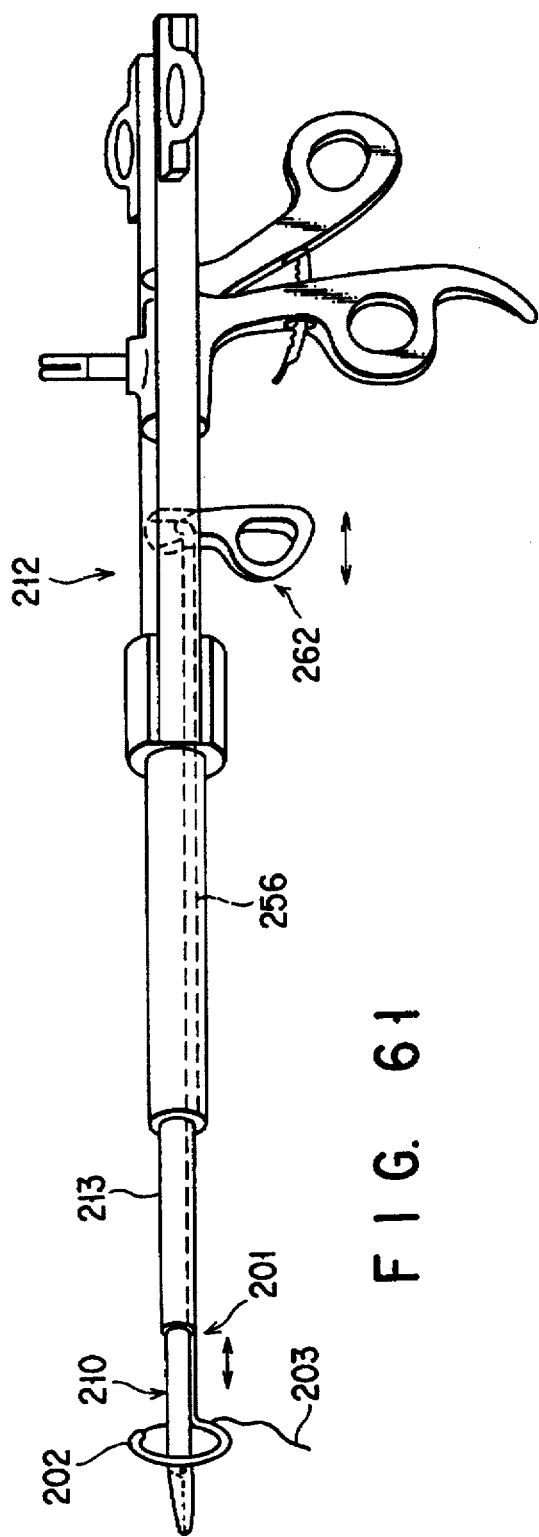
FIG. 61 shows the entire structure of a ligating apparatus according to a 13th embodiment of the invention.
Figure 62:
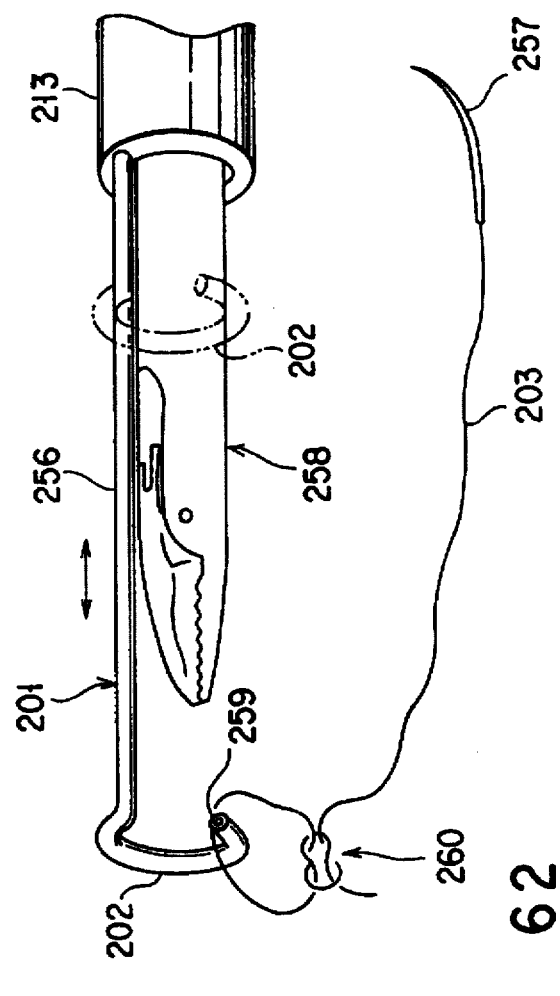
FIG. 62 shows an operating state of the ligating apparatus shown in FIG. 61.

FIGS. 61 and 62 show a 13th embodiment of the invention which is the same as the ninth embodiment, except for the points described below.

FIG. 61 shows the entire structure of the ligating apparatus according to this embodiment. As is shown in FIG. 61, in the ligating apparatus of this embodiment, the knot forming member 201 is directly built in the inner pipe 213. The straight portion 256 of the knot forming member 201 is connected to a proximal-side second handle 262. If the second handle 262 is axially moved, the knot forming member 201 moves axially within the inner pipe 213 (see FIG. 62). Thus, the first half-knot 29 can be tightened by pushing out the second handle 262. Like the tenth embodiment, the suture thread 203 is effected by binding one end portion of the suture thread 203 in the thread insertion hole 259 formed at the terminal end portion 236 of the arcuated portion 202. The needle holder 258 functioning as forceps is passed axially movably through the inner pipe 213.

FIGS. 63A and 63B show a 14th embodiment of the invention which is the same as the ninth embodiment, except for the points described below.

The knot forming member 201 of this embodiment is fixed to the inner pipe 213. Since the arcuated portion 202 has a sharp end portion 263, the arcuated portion 202 can be smoothly stabbed into the body tissue 265. The location of the thread release portion 232 differs from that of the terminal end portion 236 of the arcuated portion 202 so that the suture thread 203 may not be cut by the sharp end portion 263.

When the apparatus of this embodiment is used, the sharp end portion 263 is directly stabbed into the tissue 265 of interest and the thread release portion 232 is completely penetrated through the tissue 265 (see FIG. 63B). In this state, the suture thread 203 near the thread release portion 232 is held by the forceps 255 and the free end portion 203a of the suture thread 203 is pulled out of the tissue 265. While the free end portion 203a of the suture thread 203 is being held by the forceps 255, the arcuated portion 202 is removed from the tissue 265. Subsequently, the ligation is performed by the same procedure as in the ninth embodiment.

FIG. 64 shows a 15th embodiment of the invention which is the same as the ninth embodiment, except for the points described below.

The knot forming member 201 is fixed to the inner pipe 213. An axially movable thread fixing pipe 266 is provided between the inner pipe 213 and outer pipe 214. An abutment portion 268 is fixed to the inner pipe 213 so as to be opposed to an end face of the thread fixing pipe 266. The suture thread 203 is clamped and fixed between the thread fixing pipe 266 and abutment portion 268. Mesh-like grooves 267 for preventing slip of the suture thread 203 are formed in thread fixing surfaces of the thread fixing pipe 266 and abutment portion 268. The thread fixing pipe 266 is moved by proximal-side operating means.

FIG. 65 shows a 16th embodiment of the invention which is the same as the ninth embodiment, except for the points described below.

In this embodiment, the knot forming member 201 is irremovable. A distal end portion of the inner pipe 213 is provided with a swingable member body 271 which is swingable on a pin 270. The knot forming member 201 is fixed to a distal end portion of the swingable member body 271. Accordingly, the angle defined between the plane including the arcuated portion 202 and the axis of the inner pipe 213 varies in accordance with the swinging motion of the swingable member body 271. The swinging operation of the swingable member body 271 is performed by an operating rod 269 extending from the proximal side. According to this embodiment, the positional relationship between the knot forming member 201 and suture thread 203 can be exactly determined at the time of forming the quasi-loop 204.

In the meantime, the following two steps are very difficult in performing suture or ligation in the body cavity by means of a needle and a thread.

Figure 71A:
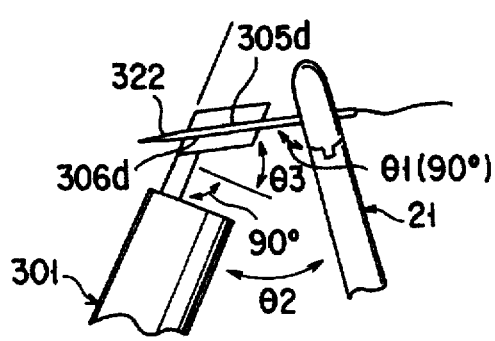
FIG. 71A and FIG. 71B illustrate an operation in which a curved needle is held by the forceps apparatus of FIG. 66.
Figure 71B:
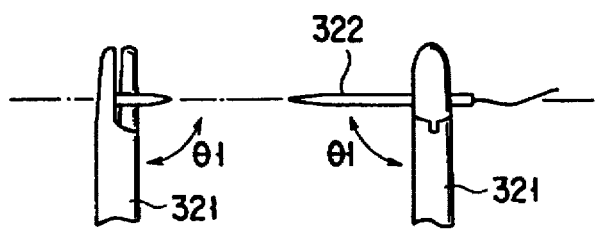

The first step is to make a needle holder hold the needle at an optimal angle. In general, a curved needle or a needle with a curved tip portion is used in endoscopic surgical operations. In order to efficiently stab the needle into the tissue, it is desirable to direct the needle at right angles to the tissue. For this purpose, as shown in FIGS. 71A and 71B, it is important to set the angle $\theta_1$ defined between the axis of a needle holder 321 and the axis of a needle 322 at 90°. It is difficult, however, to make the needle holder 321 hold the needle 322 under the condition in which the operation of the forceps is limited, and a great deal of skill and time is needed. The right part of FIG. 71B shows the state in which the needle 322 is held by the needle holder 321 with the angle $\theta_1$ being 90°. If the curved tip portion of the needle 322 is turned, as shown in the left part of FIG. 71B, in the state shown in the right part of FIG. 71B, the needle 322 moves relative to the needle holder 321 and the angle $\theta_1$ cannot be kept at 90°. In order to finely move the needle 322, the holding power of the needle holder 321 must be finely controlled. Furthermore, as shown in FIG. 71A, the angle $\theta_2$ defined between the needle holder 321 and the forceps 301 is determined by the location of an insertion hole made in the paries of the body in order to insert the forceps 301 (in normal cases the angle $\theta_2$ is 30° to 60°). Consequently, the needle 322 must be passed between the two devices 301 and 302 having the limited relative angle.

Figure 82:
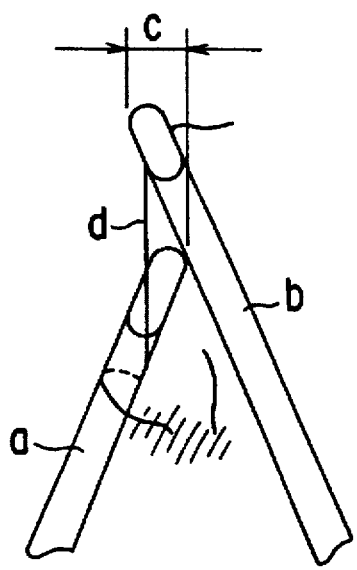
FIG. 82 illustrates a general method of forming a knot by means of the forceps apparatus.

The second step is to form the knot. In general, the knot forming operation includes a work of winding the thread around one of the forceps, as described above. This work is done between the two forceps opposed to each other with an acute angle of 30° to 60°. If the knot forming operation is performed under this condition, while avoiding mutual abutment of the two forceps, an overlap distance c of the distal end portions of both forceps a and b decreases, as shown in FIG. 82, and the work of winding a thread d is very difficult. When the free end portion of the thread d is held by the forceps a with the wound thread d, the wound thread d may be removed.

Further embodiments of the invention in which the means for solving this problem is added to the above-described structural elements will now be described.

Figure 66:
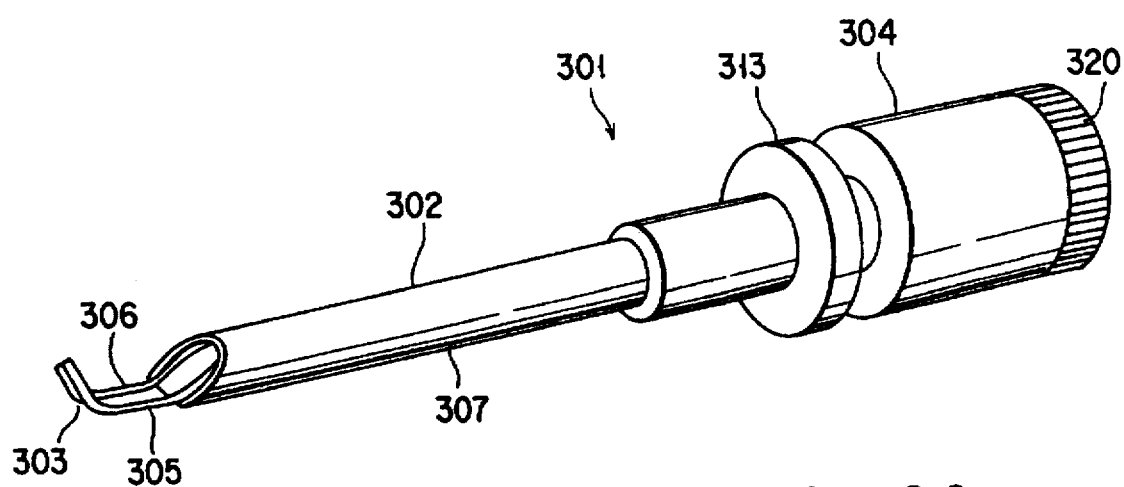
FIG. 66 is a perspective view of a forceps apparatus according to a 17th embodiment of the invention.
Figure 68A:
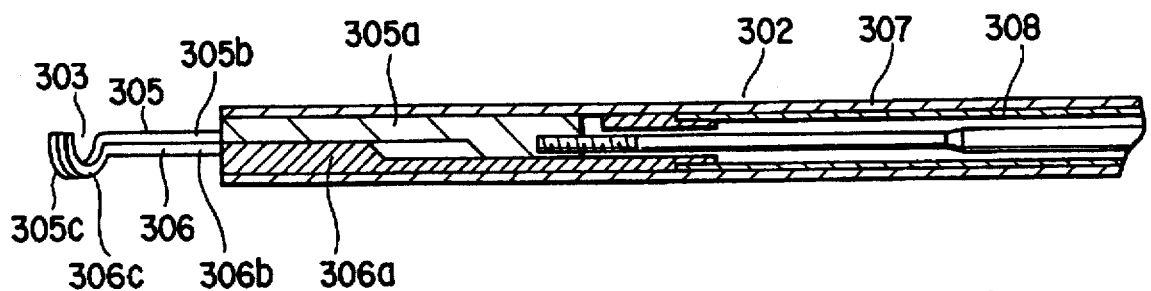
FIG. 68A is a cross-sectional view taken along line 68A—68A in FIG. 67.
Figure 68B:
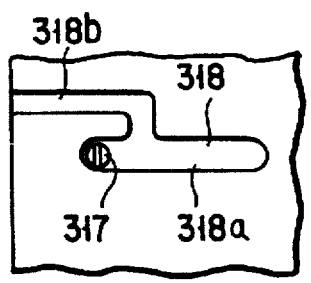
FIG. 68B is a plan view, taken in a direction of arrow 68B in FIG. 67.
Figure 67:
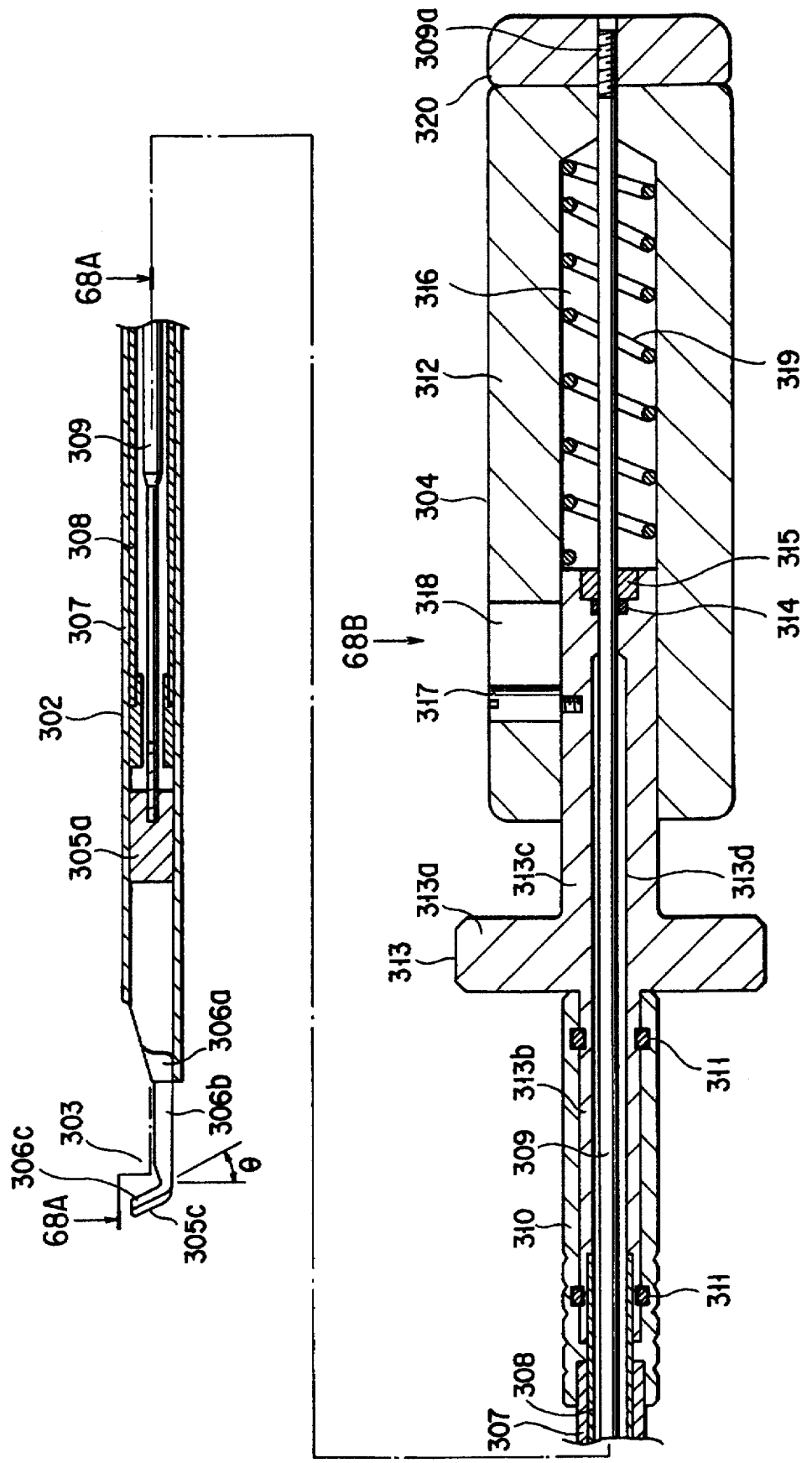
FIG. 67 is a cross-sectional view of the entire forceps apparatus shown in FIG. 66.
Figure 69:
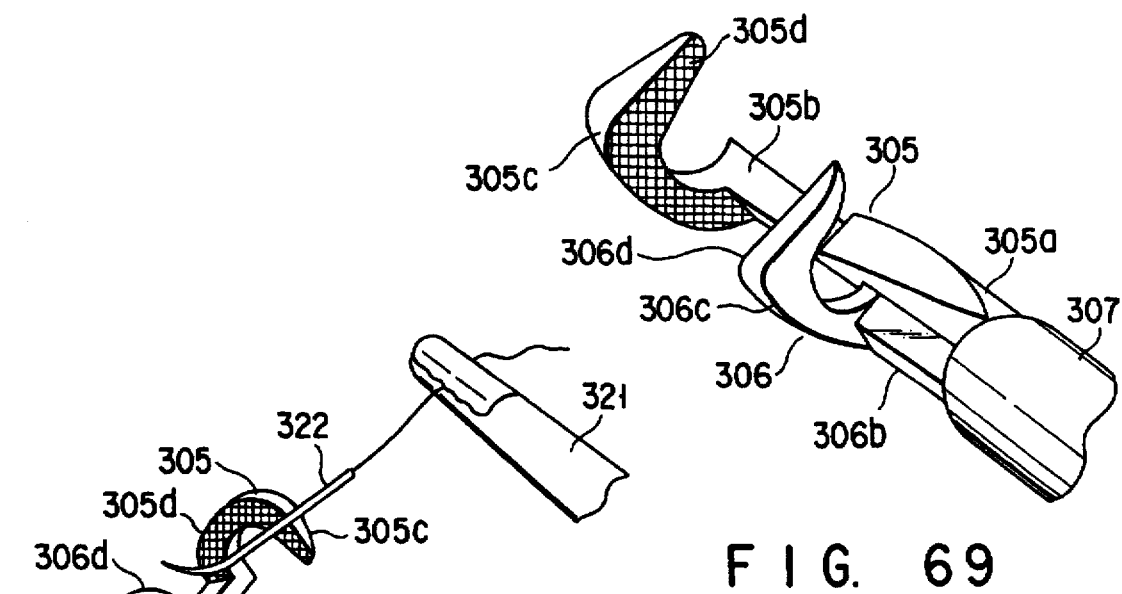
FIG. 69 is a perspective view of a distal end portion of the forceps apparatus shown in FIG. 66.

FIGS. 66 to 75D show a 17th embodiment of the invention. FIG. 66 shows a forceps device 301 as first ligating device. The forceps device 301 comprises an insertion portion 302, a distal end member 303 provided on the distal end side of the insertion portion 302, and an operating member 304 provided on the proximal end side of the insertion portion 302. The distal end member 303 comprises a first distal end portion 305 and a second distal end portion 306, as shown in FIGS. 67 to 69.

The first and second distal end portions 305 and 306 are made of a metallic material and have substantially semicylindrical base portions 305a and 306a. Arm portions 305b and 306b extend from the base portions 305a and 306a. Curved portions 305c and 306c are provided at distal end portions of the arm portions 305b and 306b at an angle θ to the axis of the insertion portion 302.

Figure 70A:
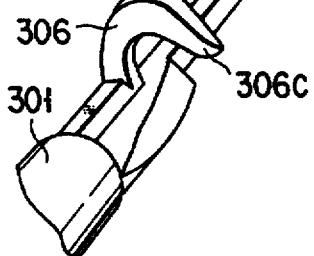
FIG. 70A and FIG. 70B illustrate an operation in which a curved needle is held by the forceps apparatus of FIG. 66.
Figure 70B:
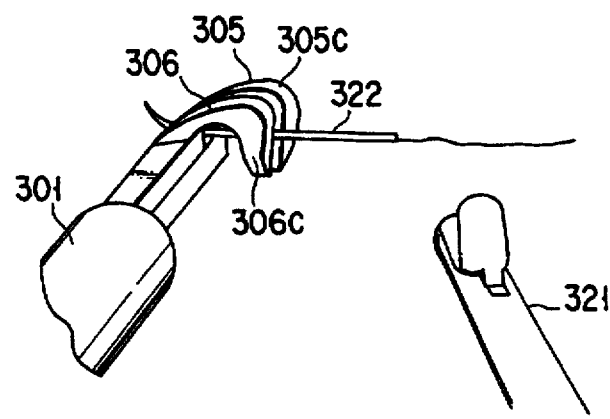

As is shown in FIG. 67, the angle θ (=$\theta_3$ (see FIG. 71A)) defined between the plane perpendicular to the axis of the forceps device 301 and the curved portion 305c, 306c is set to be substantially equal to the angle between the two forceps inserted under laparoscopy. Specifically, as shown in FIGS. 70A and 70B, this angle θ is generally set at 30° to 60°.

The curved portion 305c, 306c has a tapered straight portion near a distal end thereof. The curved portion 305c, 306c has a holding flat surface 305d, 306d. The holding flat surfaces 305d and 306d are provided with teeth for preventing slip of a held needed or thread. The first and second distal end portions 305 and 306 are axially slidable relative each other, thereby opening/closing the holding flat surfaces 305d and 306d.

The insertion portion 302 comprises an outer sheath 307, an inner pipe 308 provided inside the outer sheath 307, and an operating shaft 309 axially movable within the inner pipe 308. The second distal end portion 306 is fixed to a distal end portion of the inner pipe 308, and the first distal end portion 305 is fixed to a distal end portion of the operating shaft 309. A sleeve 310 is attached to a proximal end portion of the outer sheath 307, and two O-rings 311 are attached in the sleeve 310.

The operating member 304 comprises a cylindrical body 312 constituting a grip, and a slide member 313. The slide member 313 has a flange portion 313a and first and second sleeve portions 313b and 313c provided on both sides (front and rear) of the flange portion 313a. The slide member 313 has a through-hole 313d over the entire length thereof. The operating shaft 309 can be passed through the through-hole 313d. A rear end portion of the inner pipe 308 is fixed to the first sleeve portion 313b. A sleeve 310 is provided on the outer periphery of the first sleeve portion 313b. An O-ring 314 is attached to a terminal end of the second sleeve portion 313c by means of an O-ring holder 315. The O-ring 314 maintains hermetical sealing between the second sleeve portion 313c and the operating shaft 309.

An axial guide hole 316 is formed in the body 312 of the operating member 304. The second sleeve portion 313c is slidably inserted into the guide hole 316. A laterally projecting screw shaft 317 is fixed near a middle portion of the second sleeve portion 313c. The screw shaft 317 is engaged with a cam groove 318 formed in a peripheral wall portion of the body 312. As is shown in FIG. 68B, the cam groove 318 includes a guide groove portion 318a extending along the axis of the body 312, and a disassembly groove portion 318b branched midway from the guide groove portion 318a.

When the slide member 313 is attached to the body 312, the screw shaft 317 is introduced into the guide groove portion 318a from the disassembly groove portion 318b and the screw shaft 317 is engaged in the cam groove 318. When the slide member 313 is removed from the body 312, the slide member 313 is rotated and the screw shaft 317 is led out of the disassembly groove portion 318b from the guide groove portion 318a.

A spring 319 for urging the slide member 313 away from the body 312 is housed within the guide hole 316 in the body 312. The operating shaft 309 has a screw portion 309a at a proximal end portion thereof. The operating shaft 309 is fixed to the body 312 by tightening a nut 320 on the screw portion 309a.

The operation of the forceps device 301 having the above structure will now be described.

In the normal state, the first distal end portion 305 is fixed to the body 312 via the operating shaft 309, and the second distal end portion 306 is fixed to the slide member 313 via the inner pipe 308. Thus, the holding flat surfaces 305d and 306d of the two curved portions 305c and 306c are made to abut upon each other by the urging force of the spring 319. In other words, the holding member of the forceps device 301 is closed. From this state, the operator's finger is hooked on the flange portion 313a and the slide member 313 is pulled into the body 312 against the urging force of the spring 319. Accordingly, the inner pipe 308 is retreated and the second distal end portion 306 connected to the inner pipe 308 retreats in the axial direction of the insertion portion 302. Thereby, the holding flat surfaces 305d and 306d are separated axially from each other. In other words, the holding member of the forceps device 301 is opened. If the sleeve 310 is moved relative to the slide member 313 towards the distal-end side, the outer sheath 307 slides. Thus, the first and second distal end portions 305 and 306 are covered and protected by the outer sheath 307.

With reference to FIGS. 70A to 71B, a description will now be given of the procedure for making the needle holder 321 or second ligating member hold the needle 322 with the thread in a proper direction.

The forceps device 301 and the needle holder 321 holding the thread attached to the needle 322 are introduced into the body cavity such as the abdominal cavity via a trakal. The operating member 304 of the forceps device 301 is grasped by the hand and the flange portion 313a is pulled to the proximal side by the index finger or the thumb. Thus, the curved portions 305c and 306c of the forceps device 301 are be separated away from each other, and the curved portion of the needle 322 is put on the holding flat surface 305d (see FIG. 70A). If the flange portion 313a is released in this state, the holding flat surface 306d is moved towards the holding flat surface 305d by the urging force of the spring 319 and the curved portion of the needle 322 is clamped between the holding flat surfaces 305d and 306d (FIG. 70B). If the curved portion of the needle 322 is clamped between the two flat surfaces 305d and 306d in this manner, the distal end portion of the needle 322 is directed upwards. In this state, if the proximal end portion of the needle 322 is held by the needle holder 321 in this state, the needle 322 is held by the needle holder 321 in a proper direction.

FIG. 71A shows the state, as viewed from above, in which the needle 322 is passed from the forceps device 301 to the needle holder 321. The angle $\theta_3$ between the plane perpendicular to the axis of the forceps device 301 and the holding flat surface 305d, 306d is substantially equal to the angle $\theta_2$ between the forceps device 301 and needle holder 321. Thus, the axis of the needle 322 crosses the axis of the needle holder 321 at right angles. At this time, the needle 322 is held by the needle holder 322, as shown in FIG. 71B, since the distal end portion of the needle 322 is curved upwards. In this state, the needle 322 is stabbed into the tissue and the ligating work is performed with the thread. The procedure for this will now be described with reference to FIGS. 72A to 73C.

Figure 72A:
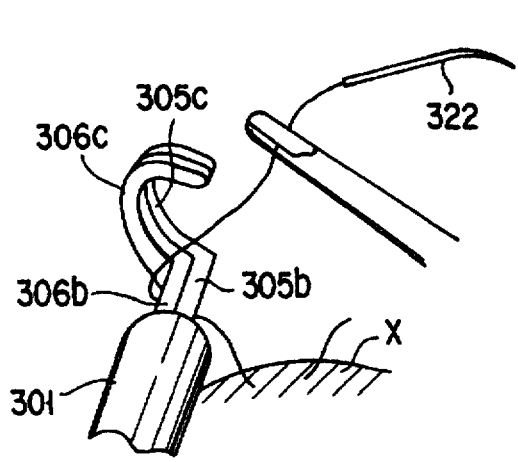
FIG. 72A and FIG. 72B illustrate an operation in which a knot is formed by using the forceps apparatus shown in FIG. 66.
Figure 72B:
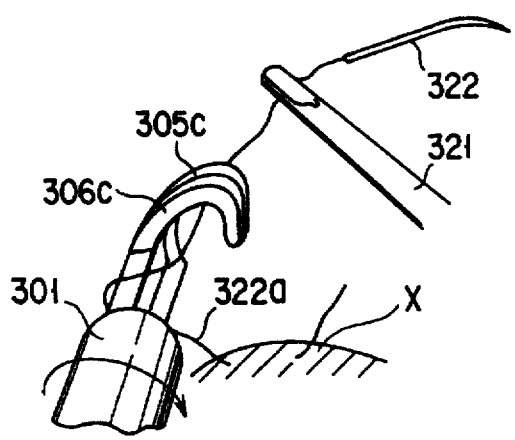
Figure 73A:
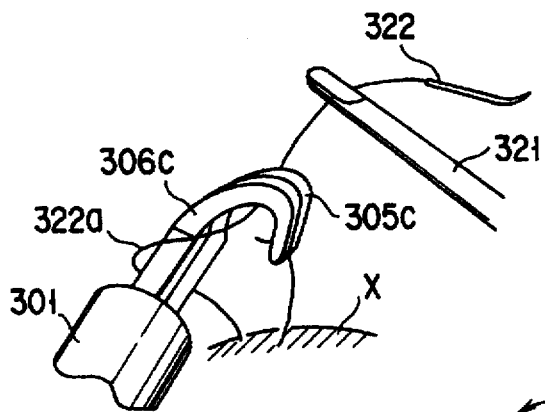
FIG. 73A to FIG. 73C illustrate an operation in which a knot is formed by using the forceps apparatus shown in FIG. 66.
Figure 73B:
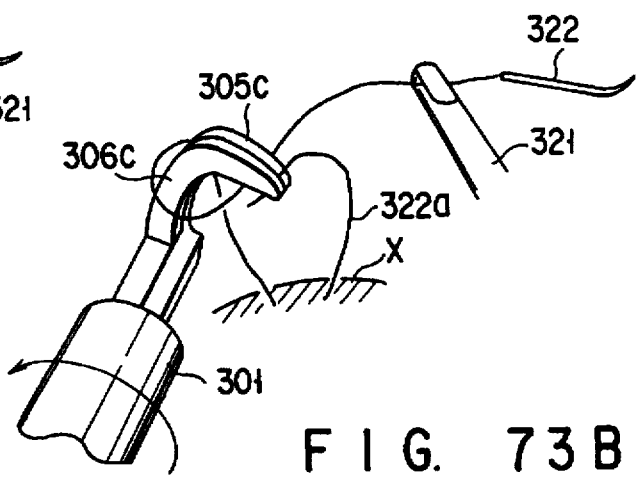
Figure 73C:
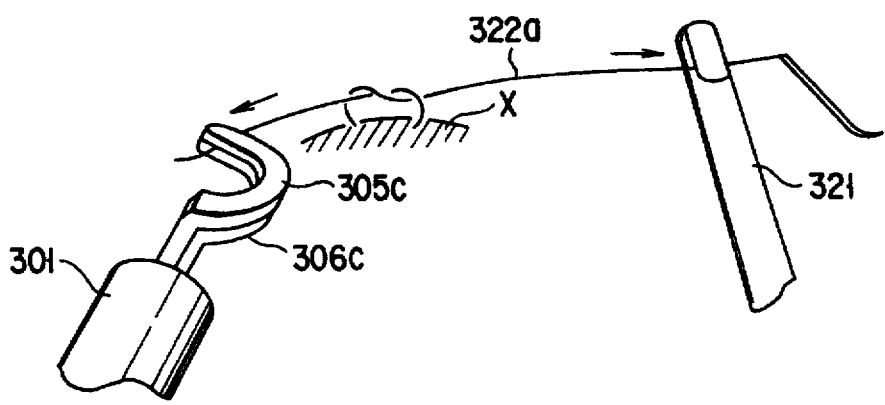
Figure 74A:
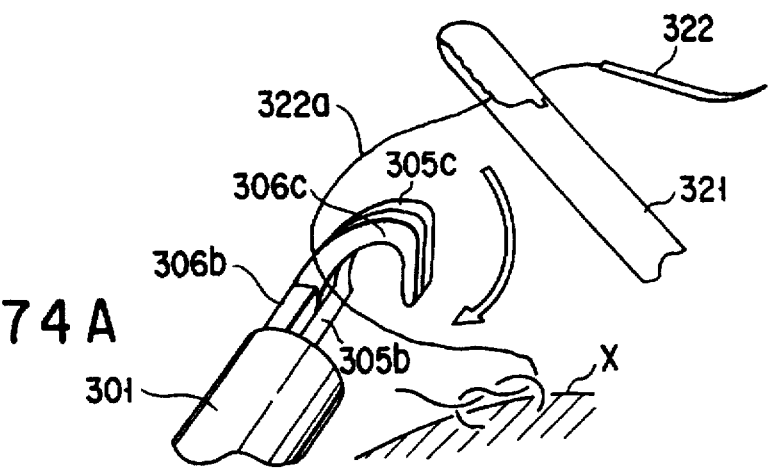
FIG. 74A to FIG. 74D illustrate an operation in which a knot is formed by using the forceps apparatus shown in FIG. 66.
Figure 74B:
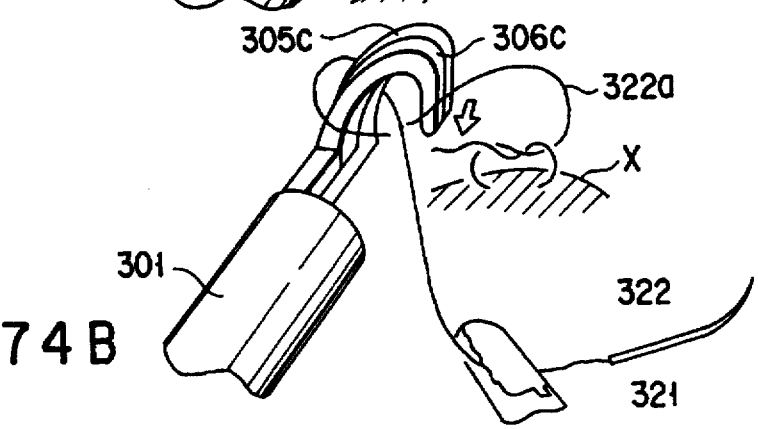
Figure 74C:
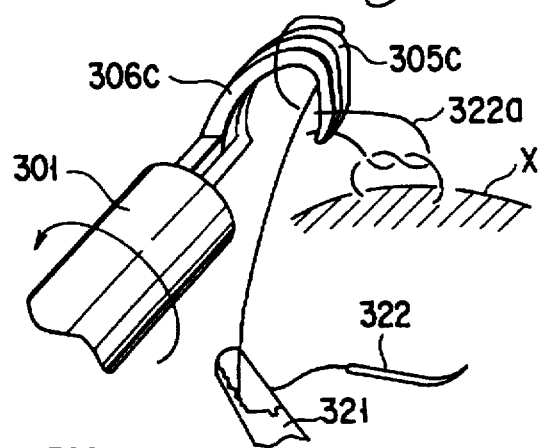
Figure 74D:
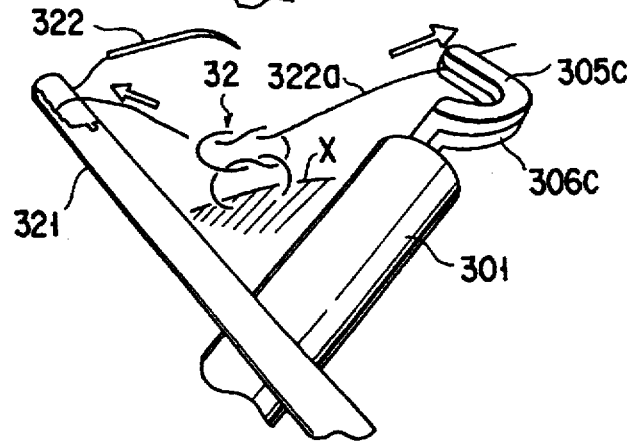

After the needle 322 is stabbed into the tissue X, a thread 322a attached to the needle 322 is held by the needle holder 321 and the thread 322a is pulled out of the tissue X to such a degree that the free end portion of the thread 322a is slightly projected from the tissue X. Then, the thread 322a located on the needle (322) side is put on the arm portions 305b and 306b of the forceps device 301 (FIG. 72A). Subsequently, the forceps device 301 is rotated and the thread 322a is brought to the inside of the curved portions 305c and 306c (FIG. 72B). Thereby, a loop of the thread 322a is formed around the first and second distal end portions 305 and 306. The free end portion of the thread 322a is held at the distal end portions of the curved portions 305c and 306c (FIG. 73A), the loop is pulled out of the curved portions 305c and 306c while the forceps device 301 is being rotated (FIG. 73B), and a first half-knot is formed by pulling the thread 322a by the forceps device 301 and needle holder 321 (FIG. 73C). When a second half-knot is formed, the free end portion of the thread 322a is released from the forceps device 301 and the thread 322a is wound around the curved portions 305c and 306c or arm portions 305b and 306b in a direction reverse to the direction of the first half-knot. Then, the free end portion of the thread 322a is held once again by the forceps device 301 (FIGS. 74A to 74C). The loop of the thread 322a is pulled out of the curved portions 305c and 306c and the forceps device 301 is moved to the right and the needle holder 321 is moved to the left. Thus, a square knot 32 is formed (FIG. 74D). If the thread winding operation, as illustrated in FIGS. 72A and 72B, is performed twice, a surgical knot can be formed.

Figure 75A:
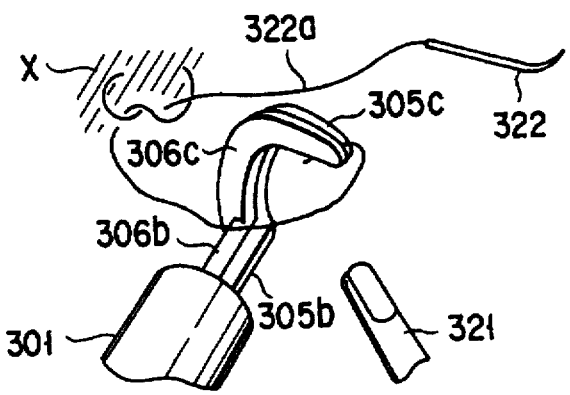
FIG. 75A to FIG. 75D illustrate another method of forming a second half-knot.
Figure 75B:
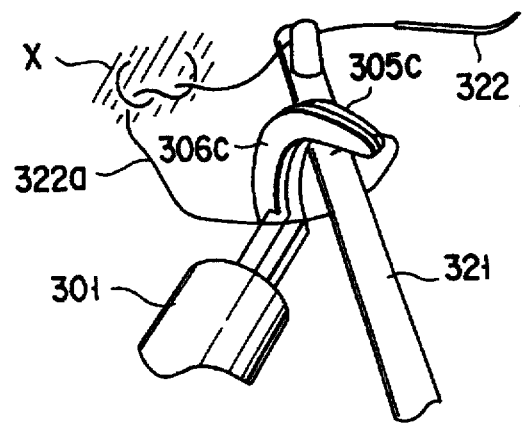
Figure 75C:
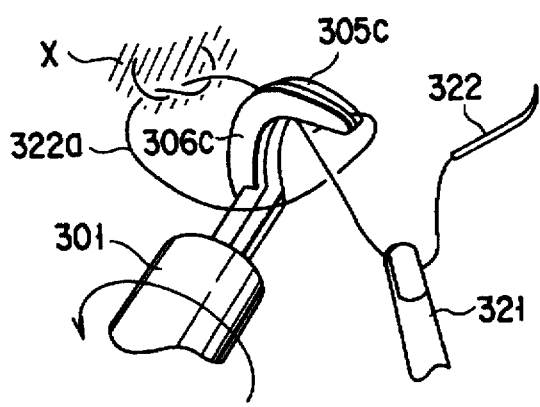
Figure 75D:
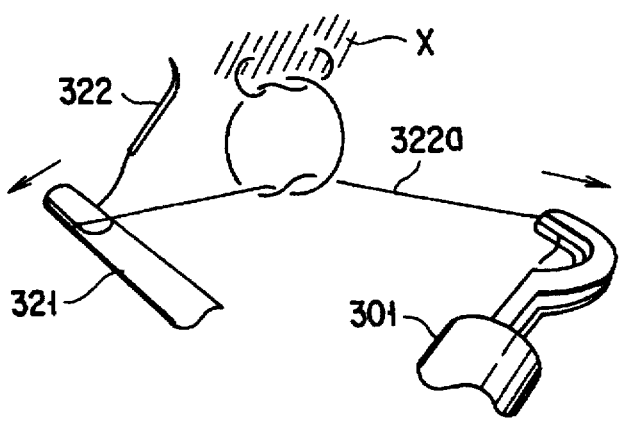

FIGS. 75A to 75D illustrate another method of forming the second half-knot. In this method, the free end portion of the thread 322a projecting from the tissue is elongated. After the first half-knot is formed, the thread 322a is released from the needle holder 321 and, as shown in FIG. 75A, the free-end side thread 322a held by the forceps device 301 is hung down on the arm portion 306b. Then, the needle holder 321 is passed through the loop formed by the curved portions 305c and 306c and the thread 322a and the thread 322a on the needle (322) side is held by the needle holder 321 (FIG. 75B). In this state, the needle holder 321 is pulled out of the loop and, while the forceps device 301 is being rotated counterclockwise, the forceps device 301 is moved to the right and the needle holder 321 is moved to the left. Thus, the square knot 32 is formed (FIGS. 75C and 75D).

As has been described above, according to the present embodiment, both two difficult steps of holding the needle and forming the knot in the intracorporeal suture can be easily performed. Besides, since the curved portions 305c and 306c have the tapered straight portions, the thread can be easily picked by the distal end portions of the curved portions 305c and 306c. Furthermore, the loop of the thread wound around the curved portions 305c and 306c can be easily removed only by the rotational operation.

In the present embodiment, if the outer sheath 307 is pulled out to the distal-end side of the insertion portion 302 and the nut 320 is loosened, the first distal end portion 305 and the operating shaft 309 can be removed. Moreover, the slide member 313 and operating member body 312 can be disassembled by disengaging the screw shaft 317 from the disassembly groove portion 318b of the cam groove 318. Therefore, the forceps device 301 can be easily assembled and disassembled and easily washed.

FIGS. 76 and 77 show an 18th embodiment of the invention. The structural elements common to those in the 17th embodiment are denoted by like reference numerals and a description thereof is omitted.

As is shown in FIG. 76, a forceps device 323 functioning as first ligating member according to this embodiment comprises a distal end member 303, an insertion portion 302 and an operating member 304. The distal end member 303 comprises a first distal end portion 305, and a second distal end portion 306 rotatably connected to the first distal end portion 305 by means of a pin 324. The shapes of curved portions 305c and 306c are the same as those in the 17th embodiment.

An operating shaft 326 is fixed to the second distal end portion 306 via a pin 325. The operating shaft 326 extends within the insertion portion 302 to the proximal-end side. The first distal end portion 305 is fixed to a distal end portion of the insertion portion 302. A rubber cap 327 is fitted on a proximal-end opening of the insertion portion 302. Thus, the operating shaft 326 projects out of the proximal end of the insertion portion 302, with hermetical sealing of the operating shaft 326 maintained.

The operating member 304 provided on the proximal side of the insertion portion 302 comprises a first handle 328 fixed to the insertion portion 302 and a second handle 329 coupled rotatably to the first handle 328. A rear end portion (i.e. proximal end portion) of the operating shaft 326 is connected to an upper end portion of the second handle 329. A ratchet 330 is provided between the first and second handles 328 and 329.

The operation of the forceps device with the above structure will now be described.

If the second handle 329 is moved away from the first handle 328, the second distal end portion 306 is rotated on the pin 324 towards the first distal end portion 305 and the holding member comprising the first and second distal end portions 305 and 306 is closed. This closed state is maintained by the ratchet 330. If the second handle 329 is moved towards the first handle 328, the second distal end portion 306 is rotated on the pin 324 away from the first distal end portion 305 and the holding member comprising the first and second distal end portions 305 and 306 is opened. Thus, the tissue, etc. can be held. The other operations are the same as those in the 17th embodiment. In the present 18th embodiment, the distal end member 303, insertion portion 302 and operating member 304 can be constructed to be dividable.

In general, when a forceps device of the above-described type is opened and closed under observation by an endoscope, one of the distal end portions may be hidden behind the other, depending on the direction of the forceps device, and the opening/closing state of the forceps device may not clearly be recognized. In particular, as regards the forceps device of the type in which only one of two distal end portions is openable, the openable distal end portion is closer to the other stationary distal end portion. Because of the characteristics of the endoscope with which an object closer to the viewer is seen to be greater in size, the stationary distal end portion is not easily recognized.

If the curved portion 306c of the second distal end portion 306 is made smaller than the curved portion 305c of the first distal end portion 305, it is possible to prevent the curved portion 305c of the stationary first distal end portion 305 from being hidden by the curved portion 306c of the movable second distal end portion 306. Therefore, the needle and thread can be easily held and the operability of the forceps device can be enhanced.

FIG. 79 shows a 19th embodiment of the invention. According to a forceps device 301 of this embodiment, curved portions 305c and 306c of first and second distal end portions 305 and 306 have oval shapes. The other structural features and operations are the same as those of the 17th and 18th embodiments In general, if the forceps device 301 is thinned, the size of a hole made in the paries in order to introduce the forceps device 301 decreases and the degree of invasion reduces. On the other hand, it becomes difficult to hold a needle and form a knot. However, if the curved portions 305c and 306c are formed to have oval shapes, as in the present embodiment, the holding of the needle and the formation of the knot can be efficiently performed even if the forceps device 301 is thinned.

FIG. 80 shows a forceps device 331 capable of exactly holding a curved needle 322. The forceps device 331 has rectangular-parallelepipedic first and second distal end portions 332 and 333. Needle holding surfaces 334 of the distal end portions 332 and 333 situated at an angle to the axis of an insertion portion 335, like the 17th embodiment.

FIG. 81 shows a forceps device 336. In this device, in order to exactly hold the curved needle 322, needle holding surfaces 339 of disk-like first and second distal end portions 337 and 338 are situated at an angle to the axis of an insertion portion 340, like the 17th embodiment.

Figure 83:
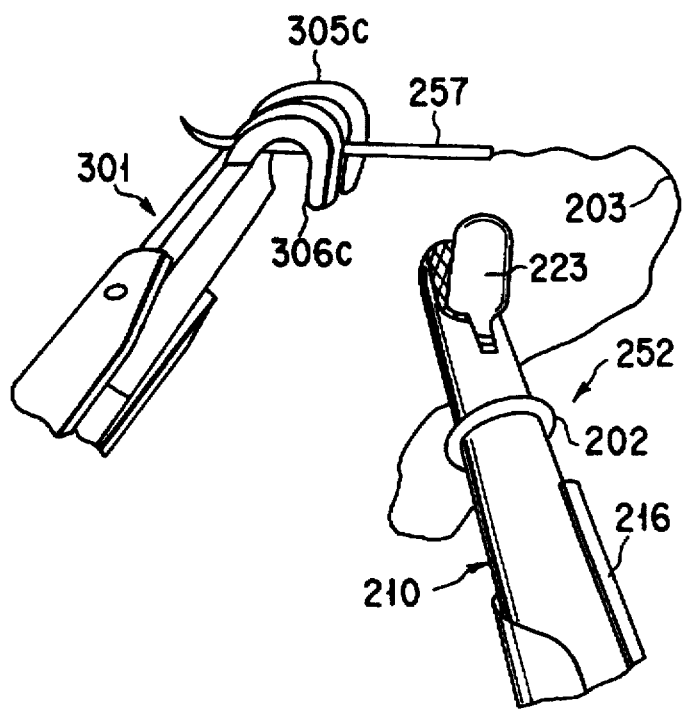
FIG. 83 is a perspective view of a ligating apparatus according to a 20th embodiment of the invention.

FIG. 83 shows a 20th embodiment of the invention in which the forceps device 301 (see FIG. 66) of the 17th embodiment is combined with the ligating device 252 (FIG. 29) of the ninth embodiment.

When the tissue is ligated by using the forceps device 301 and ligating device 252, the curved portion of the needle 257 provided at the end portion of the thread 203 extending from the thread release portion 232 of the ligating device 252 is held by the forceps device 301, thereby setting the needle 257 in a proper direction. Then, the proximal end portion of the needle 257 is held by the forceps 210 of the ligating device 252. By this operation, the needle 257 can be stabbed into the tissue at a proper position and angle and the ligating work can be quickly performed.

Figure 84:
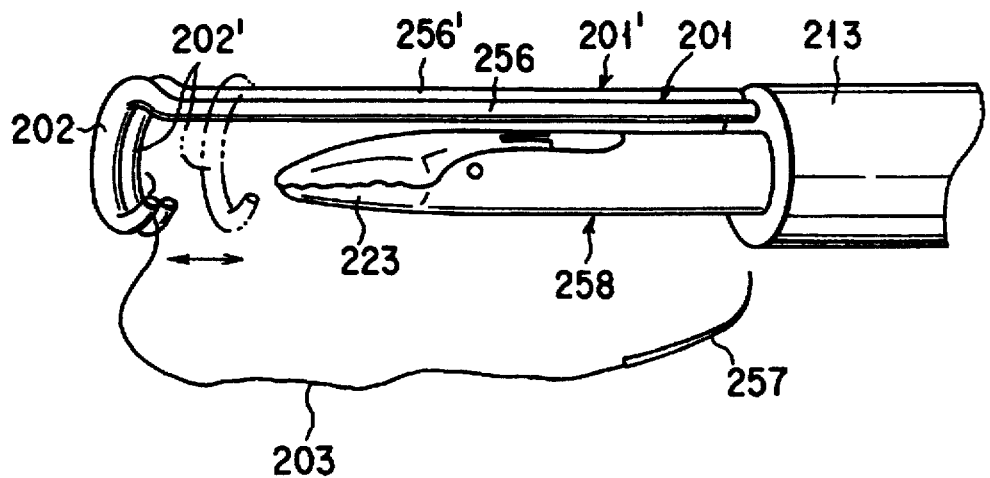
FIG. 84 is a perspective view of a ligating apparatus according to a 21st embodiment of the invention.

FIG. 84 shows a 21st embodiment of the invention. This embodiment is a modification of the 13th embodiment. As is shown in FIG. 84, in this ligating apparatus of this embodiment, two knot forming members 201 and 201' are directed coupled to the inner pipe 213. The knot forming member 201 has a straight portion 256 connected to the distal end of the inner pipe 213. The other knot forming member 201' has a straight portion 256' connected to the distal-end side second handle 262 (see FIG. 61). The inner pipe 213 can be axially moved by the operation of the second handle 262. When the knot forming member 201' is pushed forward to a maximum degree by the operation of the handle 262, the arcuated portion 202' of the knot forming member 201' abut upon the arcuated portion 202 of the knot forming member 201. A needle holder 258 functioning as forceps is movably passed through the inner pipe 213.

The arcuated portions 202 and 202' of this ligating apparatus have the same shape. In the state in which the arcuated portions 202 and 202' abut upon each other, the ligating apparatus of this embodiment functions like that of the 13th embodiment. In the state in which the arcuated portions 202 and 202' are separated from each other, it functions like the apparatus of the third embodiment.

As shown in FIG. 84, the free end portion of the thread 203 can be held by the arcuated portions 202 and 202'. This state is equivalent to the state of the tenth embodiment as shown in FIG. 57. If the operation in the ninth embodiment is performed in this state, the ligating work can be carried out. Lattice-like thin grooves (projections and recesses) are formed on the holding members of the arcuated portions 202 and 202', thereby to prevent slip of the held thread 203.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A ligating apparatus comprising:
    a first ligating member having an insertion portion to be inserted into a living body, and a holding member with a substantially C-shaped, unclosed loop portion having a constant gap section therein, said loop portion being capable of holding at least one of a ligation thread for forming a knot and a needle; and
    a second ligating member having a manipulating device capable of holding at least one of the needle and an end portion of the ligation thread, and capable of being passed through said loop portion,
    whereby when said loop portion holds the ligation thread and said manipulating device holds the end portion of the ligation thread, said second ligating member is cooperable with said first ligating member to form a knot in the ligation thread by passing the manipulating device through a knot forming loop defined by the ligation thread and said loop portion.

2. The ligating apparatus according to claim 1, wherein said holding member is detachably attached to said insertion portion.

3. The ligating apparatus according to claim 1, wherein said insertion portion comprises a tubular member, and said second ligating member is axially movably and rotatably passable through said insertion portion.

4. The ligating apparatus according to claim 3, wherein said holding member includes a longitudinal guide groove for guiding the ligation thread through said insertion portion.

5. The ligating apparatus according to claim 3, further comprising rotation means for rotating said loop portion interlockingly with an axial movement of said second ligating member.

6. The ligating apparatus according to claim 5, wherein said rotation means includes means for rotating said loop portion such that said manipulating device can pass through the knot forming loop defined by the ligation thread and said loop portion.

7. The ligating apparatus according to claim 5, wherein said rotation means comprises an engaging pin provided on one of said second ligating member and said insertion portion, and a guide groove in which said engaging pin is engaged, said guide groove being provided on the other one of said second ligating member and said insertion portion.

8. The ligating apparatus according to claim 3, further comprising a third ligating member having holding means for holding the ligation thread, said third ligating member being insertable through said insertion portion so as to pass the ligation thread between said third ligating member and said second ligating member.

9. The ligating apparatus according to claim 1, wherein said insertion portion includes thread fixing means for removably fixing an end portion of the ligation thread opposite to the end portion held by said manipulating device.

10. The ligating apparatus according to claim 9, wherein said thread fixing means includes means for engaging and disengaging the ligation thread with said insertion portion at the time of an axial movement of said second ligating member.

11. The ligating apparatus according to claim 9, wherein said thread fixing means includes means for releasing the ligation thread from said insertion portion when said manipulating device is projected to a predetermined distance from said loop portion.

12. The ligating apparatus according to claim 1, wherein said loop portion comprises a first loop portion having a first holding surface, and a second loop portion having a second holding surface which is opposed to said first holding surface and which is capable of holding one of the ligation thread and the needle between said second holding surface and said first holding surface, and further comprising a moving mechanism for moving said first loop portion and said second loop portion relative to each other in a direction such that said first holding surface comes into contact with said second holding surface.

13. The ligating apparatus according to claim 1, wherein said loop portion is movable along an axis of said insertion portion.

14. The ligating apparatus according to claim 1, wherein said loop portion projects forward from an end face of said holding member, and wherein a distance between said loop portion and said end face of said holding member is substantially equal to a length of the ligation thread extending from an end portion of said loop portion.

15. The ligating apparatus according to claim 1, wherein said loop portion comprises a tubular member having both ends opened and an inner hole with an inside diameter greater than an outside diameter of the ligation thread, whereby the ligation thread may be passed through and held in said inner hole of said loop portion.

16. The ligating apparatus according to claim 15, wherein a plurality of holes are formed midway along said loop portion, each of said holes communicating with said inner hole of said loop portion and each of said holes having an inside diameter greater than an outside diameter of the ligation thread.

17. The ligating apparatus according to claim 1, wherein a plane defined by said loop portion is situated at an angle to a longitudinal axis of said insertion portion.

18. The ligating apparatus according to claim 3, wherein a plane defined by said loop portion is situated at an angle to a longitudinal axis of said insertion portion.

19. The ligating apparatus according to claim 18, further comprising angle varying means for varying an angle between the plane defined by said loop portion and the longitudinal axis of said insertion portion.

20. The ligating apparatus according to claim 1, wherein said loop portion comprises a distal end portion having a thread fixing portion to which an end portion of the ligation thread opposite to the end portion held by said manipulating device can be fixed.

21. The ligating apparatus according to claim 1, wherein said ligation thread comprises a needle at a distal end portion thereof.

22. The ligating apparatus according to claim 1, wherein said loop portion comprises a sharp distal end portion.

23. The ligating apparatus according to claim 1, wherein said manipulating device comprises a needle holder.

24. A ligating method comprising the steps of:

forming a first knot forming loop defined by an unclosed loop portion of a first ligating member and a ligation thread held by said loop portion and extending on a first side of said loop portion, said loop portion being substantially C-shaped and having a constant gap section therein;

passing a manipulating device of a second ligating member through the first knot forming loop from said first side of said loop portion;

holding a free end portion of the ligation thread defining the first knot forming loop on a second side of said loop portion opposite to said first side with said manipulating device passed through the first knot forming loop;

passing said manipulating device holding the free end portion of the ligation thread through the first knot forming loop from said second side to said first side of said loop portion, thereby passing the free end portion of the ligation thread through the first knot forming loop to provisionally form a first half-knot;

rotating said loop portion after the free end portion of the ligation thread has been passed through the first knot forming loop, thereby falling the provisionally formed first half-knot from said loop portion through said gap section thereof;

moving in opposite directions said manipulating device holding the free end portion of the ligation thread and said first ligating member holding the ligation thread, thereby tightening the provisionally formed first half-knot fallen from said loop portion to form a tightened first half-knot;

extending the ligation thread to said second side of said loop portion while rotating said loop portion after the first half-knot has been formed, thereby forming a second knot forming loop defined by said loop portion and the ligation thread extending on said second side of said loop portion;

passing said manipulating device through the second knot forming loop from said first side to said second side of said loop portion, thereby passing the free end portion of the ligation thread held by said manipulating device through the second knot forming loop to provisionally form a second half-knot;

passing the free end portion of the ligation thread over to a holding forceps, positioned on said second side of said loop portion, from said manipulating device passed through the second knot forming loop;

rotating said loop portion after the free end portion of the ligation thread is held by said holding forceps, thereby falling the provisionally formed second half-knot from said loop portion through said gap section thereof; and moving in opposite directions said holding forceps holding the free end portion of the ligation thread and said first ligating member holding the ligation thread, thereby tightening the provisionally formed second half-knot fallen from said loop portion to form a tightened second half-knot.

* * * * *

UNITED STATES PATENT AND TRADEMARK OFFICE
CERTIFICATE OF CORRECTION

PATENT NO. : 5,702,407

DATED : December 30, 1997

INVENTOR(S) : KAJI, Kunihide

It is certified that error appears in the above-identified patent and that said Letters Patent is hereby corrected as shown below:

Title page, Item [56] References Cited, under "U.S. PATENT DOCUMENTS" insert:

```
--5,496,331   3/1996    Xu et al.          606/139
  4,641,652   2/1987    Hutterer et al.    128/334
  5,462,562   10/1995   Elkus              606/148
  5,447,512   9/1995    Wilson et al.      606/139
  5,431,669   7/1995    Thompson et al.    606/143
  5,324,298   6/1994    Phillips et al.    606/148
  5,562,685   10/1996   Mollenauer et al.  606/144--.
```

Signed and Sealed this

Second Day of March, 1999

Attest:

Attesting Officer

Q. TODD DICKINSON

Acting Commissioner of Patents and Trademarks